US00RE46630E

(19) United States
(12) Reissued Patent
Oost et al.

(10) Patent Number: US RE46,630 E
(45) Date of Reissued Patent: Dec. 12, 2017

(54) SUBSTITUTED 4-PYRIDONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Thorsten Oost, Biberach an der Riss (DE); Dennnis Fiegen, Biberach an der Riss (DE); Christian Gnamm, Biberach an der Riss (DE); Sandra Handschuh, Biberach an der Riss (DE); Stefan Peters, Biberach an der Riss (DE); Gerald Juergen Roth, Biberach an der Riss (DE)

(73) Assignee: Boehringer Ingelhelheim International GmbH, Ingelheim am Rhein (DE)

(21) Appl. No.: 14/858,408

(22) Filed: Sep. 18, 2015

Related U.S. Patent Documents

Reissue of:
(64) Patent No.: 9,102,624
Issued: Aug. 11, 2015
Appl. No.: 13/971,369
Filed: Aug. 20, 2013

(30) Foreign Application Priority Data

Aug. 23, 2012 (EP) ..... 12181539

(51) Int. Cl.

| | |
|---|---|
| ***A61K 31/54*** | (2006.01) |
| ***A61K 38/00*** | (2006.01) |
| ***A61P 11/06*** | (2006.01) |
| ***A61P 17/00*** | (2006.01) |
| ***A61P 29/00*** | (2006.01) |
| ***C07D 213/80*** | (2006.01) |
| ***C07D 213/82*** | (2006.01) |
| ***C07D 401/12*** | (2006.01) |
| ***C07D 401/14*** | (2006.01) |
| ***C07D 405/12*** | (2006.01) |
| ***C07D 405/14*** | (2006.01) |
| ***C07D 409/12*** | (2006.01) |
| ***C07D 493/08*** | (2006.01) |
| ***C07D 413/12*** | (2006.01) |

(52) U.S. Cl.
CPC ..... *C07D 213/80* (2013.01); *C07D 213/82* (2013.01); *C07D 401/12* (2013.01); *C07D 401/14* (2013.01); *C07D 405/12* (2013.01); *C07D 405/14* (2013.01); *C07D 409/12* (2013.01); *C07D 413/12* (2013.01); *C07D 493/08* (2013.01)

(58) Field of Classification Search
CPC .. C07D 405/12; C07D 213/82; C07D 401/12; C07D 401/14; C07D 493/08; C07D 409/12; C07D 413/12
See application file for complete search history.

(56) References Cited

U.S. PATENT DOCUMENTS

| | | | | |
|---|---|---|---|---|
| 4,844,732 | A * | 7/1989 | Goto et al. | 504/255 |
| 2006/0035938 | A1 | 2/2006 | Bladh et al. | |
| 2012/0149735 | A1 | 6/2012 | Millet et al. | |

FOREIGN PATENT DOCUMENTS

| | | | |
|---|---|---|---|
| EP | 1562902 | A1 | 8/2005 |
| EP | 2261211 | A1 | 12/2010 |
| WO | 03013528 | A1 | 2/2003 |
| WO | 2006098683 | A1 | 9/2006 |
| WO | 2009094417 | A1 | 7/2009 |

OTHER PUBLICATIONS

International Search Report, Form PCT/ISA/210, and Written Opinion, Form PCT/ISA/237, For Corresponding Application PCT/EP2013/067426, dated Oct. 2, 2013.

* cited by examiner

*Primary Examiner* — Gary Kunz
(74) *Attorney, Agent, or Firm* — Marc Began; Philip I. Datlow

(57) ABSTRACT

This invention relates to substituted 4-pyridones of formula 1

1 and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other auto-immune and allergic disorders, allograft rejection, and oncological diseases.

18 Claims, No Drawings

SUBSTITUTED 4-PYRIDONES AND THEIR USE AS INHIBITORS OF NEUTROPHIL ELASTASE ACTIVITY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

This invention relates to substituted 4-pyridones and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other auto-immune and allergic disorders, allograft rejection, and oncological diseases.

BACKGROUND INFORMATION

The following references describe neutrophil elastase inhibitors with a 2-pyridone central core: WO04043924, WO05026123, WO05026124, WO06098683, WO06098684, WO07129962, WO10094964, WO11039528.

The following references describe neutrophil elastase inhibitors with a 2-pyrazinone central core: WO07129963, WO09061271, WO09058076, WO11110852.

For a review on various inhibitors of neutrophil elastase see: P. Sjö (Future Med. Chem. 2012, 4, 651-660).

BRIEF SUMMARY OF THE INVENTION

Neutrophil elastase is a 29 kDa serine protease. It is expressed in bone marrow precursor cells, stored in the granula of peripheral blood granulocytes at high concentrations and it is released upon cellular activation. To the substrates of NE belong major elements of the extracellular matrix: elastin, fibronectin, laminin, collagen and proteoglycans. Neutrophil elastase activity leads to ECM degradation, increases migration and chemotaxis of monocytes and vascular smooth muscle cells and directly effects components of the coagulation and fibrinolytic pathways (PAI-1 and TFPI. Increased activity of neutrophil elastase is associated with chronic inflammatory and fibrotic diseases of several organs. Inhibitors of neutrophil elastase will therefore have an important role for the treatment of different diseases like COPD, fibrosis, cancer and others.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al., J. Pharm. Exp. Ther. 339, 313-320 (2011).

Some compounds according to the present invention, including the physiologically acceptable salts, exhibit favourable in vivo potency, as determined, for example, by the half maximal effective dose ($ED_{50}$), in a model of human neutrophil elastase-induced lung injury in mice, for instance as described in Tremblay et al., Chest 121, 582-588 (2002) or T. Stevens et al. (J. Pharm. Exp. Ther. 2011, 339, 313-320).

Some compounds according to the present invention, including the physiologically acceptable salts, exhibit favourable in vivo potency, as determined, for example, by the half maximal effective dose ($ED_{50}$), in a model of LPS/FMLP-induced lung injury in hamster, for instance as described in Mitsuhashi et al. (Br. J. Pharmacol. 1999, 126, 1147-1152).

Some compounds according to the present invention, including the physiologically acceptable salts, exhibit favourable metabolic stability in an in vitro microsomal assay for metabolic stability as described in E. Kerns & L. Di, Drug-like properties: concepts, structure design and methods: from ADME to toxicity optimization, Elsevier, $1^{st}$ ed, 2008, chapter 29 and references therein.

Some compounds according to the present invention, including the physiologically acceptable salts, exhibit favourable metabolic stability in an in vitro hepatocytes assay for metabolic stability as described in E. Kerns & L. Di, Drug-like properties: concepts, structure design and methods: from ADME to toxicity optimization, Elsevier, $1^{st}$ ed, 2008, chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}$=Dose/AUC ($F_{oral}$: oral bioavailability, AUC: area under the curve), a reduced in vivo clearance is expected lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di, Drug-like properties: concepts, structure design and methods: from ADME to toxicity optimization, Elsevier, $1^{st}$ ed, 2008, chapter 26 and references therein. For an oral drug, improved permeability is expected to translate into a higher fraction of the drug absorbed in the intestinal tract, thus, resulting in higher dose-normalized systemic exposure (AUC).

Some compounds according to the present invention, including the physiologically acceptable salts, exhibit favourable aqueous solubility in a kinetic or thermodynamic solubility method as described in E. Kerns & L. Di, Drug-like properties: concepts, structure design and methods: from ADME to toxicity optimization, Elsevier, $1^{st}$ ed, 2008, chapter 25 and references therein. For an oral drug, improved aqueous solubility is expected to translate into a higher fraction of the drug absorbed in the intestinal tract resulting in higher dose-normalized systemic exposure (AUC).

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or longer duration of action of the drug when the same dose is applied.

Some compounds according to the present invention, including the physiologically acceptable salts, exhibit favourable metabolic stability, favourable permeability and favourable aqueous solubility. Accordingly, some compounds of the present invention are expected to exhibit favourable pharmacokinetic (PK) properties, in particular favourable systemic exposure (area under the curve, AUC).

Some compounds according to the present invention, including the physiologically acceptable salts, exhibit favourable pharmacokinetic (PK) properties. The PK properties can be determined in pre-clinical animal species, for example mouse, rat, dog, guinea pig, mini pig, cynomolgus monkey, rhesus monkey. The PK properties of a compound can be described, for example, by the following parameters: Mean residence time (MRT), elimination half-live ($t_{1/2}$), volume-of-distribution ($V_D$), area under the curve (AUC), clearance (CL), bioavailability after oral administration ($F_{oral}$).

DETAILED DESCRIPTION OF THE INVENTION

Compounds of formula 1

1

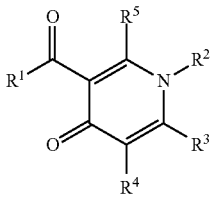

wherein $R^1$ is $H_2N$—, $R^{1.1}HN$—, $R^{1.2}HN$—, $R^{1.2}HN$—, $H(O(CH_2)_2)_2$—HN—; $H(O(CH_2)_2)_3$—HN—; $H(O(CH_2)_2)_4$—HN—, $C_{1-4}$-alkyl-O—; preferably $R^{1.1}HN$—, $R^{1.2}HN$—;

$R^{1.1}$ is $C_{3-6}$-cycloalkyl or a four-, five- or six-membered, non-aromatic heteroring, wherein one, two or three, preferably one or two elements are replaced by an element selected independent from each other from the group consisting of N, O, S, (O)S and $(O)_2S$; wherein each element of one of the above mentioned rings is optionally substituted with a residue selected from the group consisting of HO—, O═, $C_{1-4}$-cycloalkyl-, $C_{1-4}$-haloalkyl-, halogen, NC—;

and if the rings contains nitrogen, it is optionally substituted with $C_{1-4}$-alkyl-, $C_{3-6}$cycloalkyl-, $C_{1-4}$-haloalkyl-, $C_{1-4}$-alkyl-(O)C—, $C_{1-4}$-haloalkyl-(O)C—, $C_{3-6}$-cycloalkyl-(O)C—, $C_{1-4}$-alkyl-O(O)C—, $C_{1-4}$-alkyl-HN(O)C—, $(C_{1-4}$-alkyl$)_2$N(O)C—, $C_{1-4}$-alkyl-$(O)_2S$—;

$R^{1.2}$ is a branched or unbranched $C_{1-6}$-alkyl-, $C_{2-6}$-alkenyl or $C_{2-6}$-alkynyl, optionally substituted independently from each other with one, two or three residues selected from the group consisting of O═, HO—, halogen, NC—, $C_{1-4}$-alkyl-O—, $H_2N$—, ($C_{1-4}$-alkyl)-HN—, $(C_{1-4}$-alkyl$)_2$N—, $C_{1-4}$-alkyl-O(O)C—, HO(O)C—, $H_2N$—(O)C—, ($C_{1-4}$-alkyl)-HN—(O)C—, $(C_{1-4}$-alkyl$)_2$N(O)C—, ($C_{1-4}$-alkyl)-(O)C—HN—, ($C_{1-4}$-alkyl)-(O)C—($C_{1-4}$-alkyl)N—, ($C_{1-4}$-alkyl)-O(O)C—HN—, ($C_{1-4}$-alkyl)-O(O)C—($C_{1-4}$-alkyl)N—, $H_2N$—(O)C—NH—, ($C_{1-4}$-alkyl)-NH—(O)C—NH—, $(C_{1-4}$-alkyl$)_2$N—(O)C—HN—, $H_2N$—(O)C—($C_{1-4}$-alkyl)N—, ($C_{1-4}$-alkyl)-HN—(O)C—($C_{1-4}$-alkyl)N—, $(C_{1-4}$-alkyl$)_2$N—(O)C—($C_{1-4}$-alkyl)N—, $C_{1-4}$-alkyl-(O)S—, $C_{1-4}$-alkyl-$(O)_2S$—, $C_{1-4}$-alkyl-(HN)(O)S—, $C_{1-4}$-alkyl-($C_{1-4}$-alkyl-N)(O)S—, $C_{1-4}$-alkyl-(NC—N)(O)S—, $C_{1-4}$-alkyl-$(O)_2S$—HN—, $C_{1-4}$-alkyl-$(O)_2S$—($C_{1-4}$-alkyl)N—;

Azetidinyl-(O)C—, Pyrrolidinyl-(O)C—, Piperidinyl-(O)C—, Morpholinyl-(O)C—;

Azetidinyl-(O)C—HN—, Pyrrolidinyl-(O)C—HN—, Piperidinyl-(O)C—HN—, Morpholinyl-(O)C—HN—; Azetidinyl-(O)C—($C_{1-4}$-alkyl)N—, Pyrrolidinyl-(O)C—($C_{1-4}$-alkyl)N—, Piperidinyl-(O)C—($C_{1-4}$-alkyl)N—, Morpholinyl-(O)C—($C_{1-4}$-alkyl)N—;

a ring selected from $C_{1-6}$-cycloalkyl-, phenyl, a five- or six-membered, aromatic or non-aromatic heteroring, wherein one, two or three elements of the ring are replaced by an element selected independent from each other from the group consisting of N, $(O^-)$—$N^+$, O, S, (O)S and $(O)_2S$; or a ring system of two fused aromatic or non-aromatic heterorings, wherein one or two elements of the rings are replaced by an element selected independent from each other from the group consisting of N, O, S, (O)S and $(O)_2S$; wherein each element of one of the above mentioned rings and fused rings is optionally substituted with a residue selected from the group consisting of O═, $C_{1-4}$-alkyl-O(O)C—, $C_{3-6}$-cycloalkyl-, HO—, $C_{1-4}$-alkyl-O—, NC—, halogen, $C_{1-4}$-alkyl-S—, $C_{1-4}$-alkyl-$(O)_2S$—, $Me_2N$—$CH_2$—(O)C—; preferably methyl, HO—, MeO—, NC—, $H_3CS$—, $H_3C(O)S$—, $H_3C(O)_2S$—;

wherein tertiary amines in principal can also be quaternary together with $(H_3C)^+Y^-$ and Y is an anion; preferably a pharmaceutically acceptable anion; preferably $Cl^-$ $R^2$ is $R^{2.1}R^{2.2}R^{2.3}C$—;

R2.1 is phenyl or a five- or six-membered, aromatic heteroring, wherein one, two or three elements are replaced by an element selected independent from each other from the group consisting of N, O and S; wherein each element of one of the above mentioned rings is optionally substituted with a residue selected from the group consisting of O═, $C_{1-4}$-alkyl-, $C_{3-6}$-cycloalkyl-, $C_{1-4}$-haloalkyl-, halogen, NC—, $C_{1-4}$-alkyl-O—, $C_{1-4}$-alkyl-$(O)_2S$—, $C_{3-6}$-cycloalkyl-$(O)_2S$—, $C_{1-4}$-alkyl-O—HN—S—, $C_{1-4}$-alkyl-HN—S—, $C_{1-4}$-alkyl-O—($C_{1-4}$-alkyl)N—S—, $C_{1-4}$-alkyl-O—HN(O)S—, ($C_{1-4}$-alkyl-($C_{1-4}$-alkyl-N)(O)S—, $C_{1-4}$-alkyl-(NC—N)(O)S—;

$R^{2.2}$ is H or $C_{1-4}$-alkyl-;

$R^{2.3}$ is H or $C_{1-4}$-alkyl-;

or $R^{2.2}$ and $R^{2.3}$ are forming together a $C_{2-5}$-alkylene;

or $R^{2.1}$ is phenyl, optionally substituted with NC—, and $R^{2.2}$ is $C_{2-3}$-alkylene forming together with the ortho position of the phenyl ring a fused ring system, wherein optionally one element is replaced by an element selected independent from each other from the group consisting of O and $(O)_2S$; e.g. $R^2$ is a group of one of the following formulas

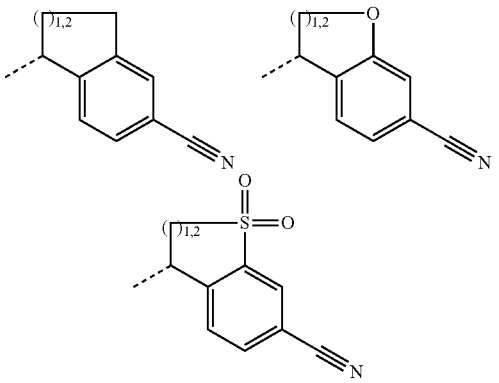

$R^3$ is H or $C_{1-4}$-alkyl-;

$R^4$ is phenyl or a five- or six-membered, aromatic heteroring, wherein one or two elements are replaced by an element selected independent from each other from the group consisting of N, O and S; wherein each element of one of the above mentioned rings is optionally substituted with a residue selected from the group consisting of O═, $C_{1-4}$-haloalkyl-, halogen;

$R^5$ is selected from the group consisting of H, $C_{1-4}$-alkyl-, $C_{1-4}$-alkyl-O—, $C_{1-4}$-haloalkyl- or halogen;

or a salt thereof.

Preferred Embodiments

Preferred are the above compounds of formula 1, wherein $R^1$ is $H_2N$ , $R^{1.1}HN$—, $R^{1.2}HN$—, $H(O(CH_2)_2)_3$—HN—;

$R^{1.1}$ is $C_{3-6}$-cycloalkyl- or a four-, five- or six-membered, non-aromatic heteroring, wherein one or two elements are replaced by an element selected independent from each other from the group consisting of N, O, S, (O)S and $(O)_2S$; wherein each element of one of the above mentioned rings is optionally substituted with a residue selected from the group consisting of HO—, NC—, O═, $C_{1-4}$-cycloalkyl-;

$R^{1.2}$ is a branched or unbranched $C_{1-4}$-alkyl-, optionally substituted independently from each other with one, two or three, preferably one or two residues selected from the group consisting of HO—, NC—, F, $C_{1-4}$-alkyl-O—, $(C_{1-4}\text{-alkyl})_2$-N—, $C_{1-4}$-alkyl-O(O)C—, HO(O)C—, $(C_{1-4}\text{-alkyl})_2$-N(O) C—, $C_{1-4}$-alkyl-(O)S—, $C_{1-4}$-alkyl-$(O)_2S$—;

a ring selected from $C_{1-6}$-cycloalkyl-, phenyl, a five- or six-membered, aromatic or non-aromatic heteroring, wherein one, two or three elements are replaced by an element selected independent from each other from the group consisting of N, $(O^-)$—$N^+$ and O; wherein each element of one of the above mentioned rings is optionally substituted with a residue selected from the group consisting of O═, $C_{1-4}$-alkyl-, $C_{1-4}$-haloalkyl-, $C_{3-6}$-cycloalkyl-, HO—, $C_{1-4}$-alkyl-O—, NC—, $C_{1-4}$-alkyl-S—, $C_{1-4}$-alkyl-(O)S—, $C_{1-4}$-alkyl-$(O)_2S$—, $Me_2N$—$CH_2$—(O)C—;

$R^2$ is $R^{2.1}R^{2.2}R^{2.3}C$—;

$R^{2.1}$ is phenyl or a five- or six-membered, aromatic heteroring, wherein one or two elements are replaced by an element selected independent from each other from the group consisting of N, O and S; wherein one or two elements of one of the above mentioned rings are optionally substituted with a residue selected from the group consisting of halogen, NC—, $C_{1-4}$-alkyl-, $C_{1-4}$-haloalkyl-, $C_{1-4}$-alkyl-O—, $C_{1-4}$-alkyl-$(O)_2S$—, $C_{3-6}$-cycloalkyl-$(O)_2S$—;

$R^{2.2}$ is H or $C_{1-4}$-alkyl-; preferably H;

$R^{2.3}$ is H or $C_{1-4}$-alkyl-; preferably H or methyl;

or $R^{2.2}$ and $R^{2.3}$ are forming together a $C_{2-5}$-alkylene;

$R^3$ is $C_{1-4}$-alkyl-;

$R^4$ is phenyl or a six-membered, aromatic heteroring, wherein one or two elements are replaced by N; wherein one or two elements of one of the above mentioned rings are optionally substituted with a residue selected from the group consisting of $C_{1-4}$-alkyl-, $C_{1-4}$-haloalkyl-, halogen;

$R^5$ is H;

or a salt thereof.

Preferred are the above compounds of formula 1, wherein $R^1$ is $R^{1.1}HN$—, $R^{1.2}HN$—;

$R^{1.1}$ is $C_{3-6}$-cycloalkyl or a four-membered, non-aromatic heteroring, wherein one element is replaced by an O; wherein each element of one of the above mentioned rings is optionally substituted with NC—;

$R^{1.2}$ is a branched or unbranched $C_{1-4}$-alkyl-, preferably methyl or ethyl; each optionally substituted with a ring selected from phenyl or a five- or six-membered, aromatic or non-aromatic heteroring, wherein one, two or three elements are replaced by an element selected independent from each other from the group consisting of N, $(O^-)$—$N^+$ and O; wherein each element of one of the above mentioned rings is optionally substituted with a residue selected from the group consisting of O═, $C_{1-4}$-alkyl-, $C_{1-4}$-haloalkyl-, $C_{3-6}$-cycloalkyl-, HO—, $C_{1-4}$-alkyl-O—, NC—, $C_{1-4}$-alkyl-S—, $C_{1-4}$-alkyl-(O)S—, $C_{1-4}$-alkyl-$(O)_2S$—, $Me_2N$—$CH_2$—(O)C—; preferably $C_{1-4}$-alkyl-$(O)_2S$—; preferably $H_3C$—$(O)_2S$—;

$R^2$ is $R^{2.1}R^{2.2}R^{2.3}C$—;

$R^{2.1}$ is phenyl, a five- or six-membered, aromatic heteroring, wherein one or two elements, preferably one element, are replaced by an element selected independent from each other from the group consisting of N, O and S, preferably phenyl or pyridinyl; wherein one or two elements of one of the above mentioned rings are substituted with a residue selected from the group consisting of halogen, NC—, $C_{1-4}$-alkyl-, $C_{1-4}$-haloalkyl-, $C_{1-4}$-alkyl-O—, $C_{1-4}$-alkyl-$(O)_2S$—, $C_{3-6}$-cycloalkyl-$(O)_2S$—; preferably F, NC—, MeO—, $H_3C$—$(O)_2S$—;

$R^{2.2}$ is H or $C_{1-4}$-alkyl-; preferably H;

$R^{2.3}$ is H or $C_{1-4}$-alkyl-; preferably H or methyl;

$R^3$ is $C_{1-4}$-alkyl-; preferably methyl;

$R^4$ is phenyl or pyridinyl, substituted with $C_{1-4}$-haloalkyl-; preferably $FH_2C$—, $F_2HC$— or or $F_3C$—; preferably $FH_2C$—, $F_2HC$— or $F_3C$— in meta position;

$R^5$ is H;

or a salt thereof.

Preferred are the above compounds of formula 1, wherein $R^1$ is $R^{1.1}$ HN—, $R^{1.2}HN$—;

$R^{1.1}$ is $C_{3-6}$-cycloalkyl or a four-membered, non-aromatic heteroring, wherein one element is replaced by an O; wherein each element of one of the above mentioned rings is optionally substituted with NC—;

$R^{1.2}$ is a branched or unbranched $C_{1-4}$-alkyl-, preferably methyl, substituted with a phenyl ring which is substituted with $C_{1-4}$-alkyl-(O)S—;

$R^2$ is $R^{2.1}R^{2.2}R^{2.3}C$—;

$R^{2.1}$ is phenyl or pyridinyl substituted with NC—;

$R^{2.2}$ is H;

$R^{2.3}$ is H or $C_{1-4}$-alkyl-; preferably H or methyl;

$R^3$ is $C_{1-4}$-alkyl-; preferably methyl;

$R^4$ is phenyl, substituted with $C_{1-4}$-haloalkyl-; preferably $FH_2C$—, $F_2HC$— or $F_3C$—; preferably $FH_2C$—, $F_2HC$— or $F_3C$— in meta position;

$R^5$ is H;

or a salt thereof.

Preferred are the above compounds of formula 1, wherein $R^1$ is $R^{1.1}HN$—, $R^{1.2}HN$—;

$R^{1.1}$ is $C_{3-6}$-cycloalkyl or a four-membered, non-aromatic heteroring, wherein one element is replaced by an O; wherein each element of one of the above mentioned rings is optionally substituted with NC—;

$R^{1.2}$ is a branched or unbranched $C_{1-4}$-alkyl-, preferably methyl, substituted with a phenyl ring which is substituted with $C_{1-4}$-alkyl-$(O)_2S$—;

$R^2$ is $R^{2.1}R^{2.2}R^{2.3}C$—;

$R^{2.1}$ is phenyl or a five- or six-membered, aromatic heteroring, wherein one or two elements are replaced by an element selected independent from each other from the group consisting of N, O and S, preferably phenyl or pyridinyl; wherein one or two elements of one of the above mentioned rings are substituted with a residue selected from the group consisting of halogen, NC—, $C_{1-4}$-alkyl-, $C_{1-4}$-haloalkyl-, $C_{1-4}$-alkyl-O—, $C_{1-4}$-alkyl-$(O)_2S$—; preferably F, NC—, MeO—;

$R^{2.2}$ is H;

$R^{2.3}$ is H or $C_{1-4}$-alkyl-; preferably H or methyl;

$R^3$ is $C_{1-4}$-alkyl-; preferably methyl;

$R^4$ is phenyl, substituted with $C_{1-4}$-haloalkyl-; preferably $FH_2C$—, $F_2HC$— or $F_3C$—; preferably $FH_2C$—, $F_2HC$— or $F_3C$— in meta position;

$R^5$ is H;

or a salt thereof.

Preferred are the above compounds of formula 1, wherein $R^1$ is $R^{1.1}HN$—, $R^{1.2}HN$—;

$R^{1.1}$ is $C_{3-6}$-cycloalkyl or a four-membered, non-aromatic heteroring, wherein one element is replaced by an O; wherein each element of one of the above mentioned rings is optionally substituted with NC—;

$R^{1.2}$ is a branched or unbranched $C_{1-4}$-alkyl-, preferably methyl or ethyl each optionally substituted with one NC— or one, two or three F;

$R^2$ is $R^{2.1}R^{2.2}R^{2.3}C$—;

R2.1 is phenyl or pyridinyl substituted with a residue selected from the group consisting of NC—, $C_{1-4}$-alkyl-$(O)_2S$—; preferably NC—, $H_3C$—$(O)_2S$—;

$R^{2.2}$ is H;

$R^{2.3}$ is H or $C_{1-4}$-alkyl-; preferably H or methyl;

$R^3$ is $C_{1-4}$-alkyl-; preferably methyl;

$R^4$ is phenyl or pyridinyl, substituted with $C_{1-4}$-haloalkyl-; preferably $FH_2C$—, $F_2HC$— or $F_3C$—;

$R^5$ is H;

or a salt thereof.

Preferred are the above compounds of formula 1, wherein $R^1$ is $R^{1.1}HN$—, $R^{1.2}HN$—;

$R^{1.1}$ is $C_{3-6}$-cycloalkyl or a four-membered, non-aromatic heteroring, wherein one element is replaced by an O; wherein each element of one of the above mentioned rings is optionally substituted with NC—;

$R^{1.2}$ is a branched or unbranched $C_{1-4}$-alkyl-, preferably methyl, substituted with a five- or six-membered, aromatic or non-aromatic heteroring, wherein one, two or three elements are replaced by an element selected independent from each other from the group consisting of N, $(O^-)$—$N^+$ and O; which is substituted with O═ or $C_{1-4}$-alkyl-$(O)_2S$—;

$R^2$ is $R^{2.1}R^{2.2}R^{2.3}C$—;

$R^{2.1}$ is phenyl or a five- or six-membered, aromatic heteroring, wherein one or two elements are replaced by an element selected independent from each other from the group consisting of N, O and S, preferably phenyl or pyridinyl; wherein one or two elements of one of the above mentioned rings are substituted with a residue selected from the group consisting of halogen, NC—, $C_{1-4}$-alkyl-, $C_{1-4}$-haloalkyl-, $C_{1-4}$-alkyl-O—, $C_{1-4}$-alkyl-$(O)_2S$—; preferably F, NC—, MeO—;

$R^{2.2}$ is H or $C_{1-4}$-alkyl-; preferably H;

$R^{2.3}$ is H or $C_{1-4}$-alkyl-; preferably H or methyl;

$R^3$ is $C_{1-4}$-alkyl-; preferably methyl;

$R^4$ is phenyl, substituted with $C_{1-4}$-haloalkyl-; preferably $F_3C$—; preferably $F_3C$— in meta position;

$R^5$ is H;

or a salt thereof.

Preferred are the above compounds of formula 1, wherein $R^1$ is $R^{1.1}HN$—, $R^{1.2}HN$—;

$R^{1.1}$ is cyclopropyl or oxetanyl; wherein each element of one of the above mentioned rings is optionally substituted with NC—;

$R^{1.2}$ is a branched or unbranched $C_{1-4}$-alkyl-, preferably methyl, substituted with a phenyl ring which is substituted with $C_{1-4}$-alkyl-$(O)_2S$—;

$R^2$ is $R^{2.1}R^{2.2}R^{2.3}C$—;

$R^{2.1}$ is phenyl or a five- or six-membered, aromatic heteroring, wherein one or two elements are replaced by an element selected independent from each other from the group consisting of N, O and S, preferably phenyl or pyridinyl; wherein one or two elements of one of the above mentioned rings are substituted with a residue selected from the group consisting of halogen, NC—, $C_{1-4}$-alkyl-, $C_{1-4}$-haloalkyl-, $C_{1-4}$-alkyl-O—, $C_{1-4}$alkyl-$(O)_2S$—; preferably F, NC—, MeO—;

$R^{2.2}$ is H or $C_{1-4}$-alkyl-; preferably H;

$R^{2.3}$ is H or $C_{1-4}$-alkyl-; preferably H or methyl;

$R^3$ is $C_{1-4}$-alkyl-; preferably methyl;

$R^4$ is pyridinyl, substituted with $C_{1-4}$-haloalkyl-; preferably $F_3C$—; preferably $F_3C$— in meta position;

$R^5$ is H;

or a salt thereof.

Preferred are the above compounds of formula 1, wherein $R^1$ is $R^{1.1}HN$—, $R^{1.2}HN$—;

$R^{1.1}$ is cyclopropyl or oxetanyl; wherein each element of one of the above mentioned rings is optionally substituted with NC—;

$R^{1.2}$ is a branched or unbranched $C_{1-4}$-alkyl-, preferably methyl, substituted with a phenyl ring which is substituted with $C_{1-4}$-alkyl-$(O)_2S$—;

$R^2$ is $R^{2.1}R^{2.2}R^{2.3}C$—;

$R^{2.1}$ is phenyl substituted with NC—;

$R^{2.2}$ is H;

$R^{2.3}$ is H or $C_{1-4}$-alkyl-; preferably H or methyl;

$R^3$ is $C_{1-4}$-alkyl-; preferably methyl;

$R^4$ is phenyl or a six-membered, aromatic heteroring, wherein one or two elements are replaced by N; preferably phenyl or pyridinyl; wherein one or two elements of one of the above mentioned rings are substituted with a residue selected from the group consisting of $C_{1-4}$-alkyl-, $C_{1-4}$-haloalkyl-, halogen; preferably methyl, Cl—, $HF_2C$—, $F_3C$—;

$R^5$ is H;

or a salt thereof.

Preferred are the above compounds of formula 1, wherein $R^1$, $R^2$, $R^3$ and $R^5$ as described above and $R^4$ is phenyl or a six-membered, aromatic heteroring, wherein one or two elements are replaced by N; preferably phenyl or pyridinyl;

wherein one or two elements of one of the above mentioned rings are optionally substituted with a residue selected from the group consisting of $C_{1-4}$-alkyl-, $C_{1-4}$-haloalkyl-, halogen; preferably methyl, Cl—, $HF_2C$—, $F_3C$—; preferably $F_3C$—; preferably $F_3C$— in meta position; or a salt thereof.

Preferred are the above compounds of formula 1, wherein $R^1$, $R^3$, $R^4$ and $R^5$ as described above and $R^2$ is $R^{2.1}R^{2.2}R^{2.3}C$—;

$R^{2.1}$ is phenyl or pyridinyl substituted with NC—;

$R^{2.2}$ is H;

$R^{2.3}$ is H or methyl; preferably methyl;

or a salt thereof.

Also preferred are the above compounds of formula 1, wherein $R^1$ is $H_2N$—, $R^{1.1}HN$—, $R^{1.2}HN$—, $H(O(CH_2)_2)_3$—HN—;

$R^{1.1}$ is cyclopropyl, cyclohexyl, oxetanyl, tetrahydrofuranyl, tetrahydropyranyl, pyrrolidin-2-onyl, piperidin-2-onyl, tetrahydrothiophen-1,1-dioxidyl, each optionally substituted with methyl, NC— or HO—, preferably NC— or methyl;

$R^{1.2}$ is a branched or unbranched $C_{1-4}$-alkyl-, optionally substituted independently from each other with one or two residues selected from the group consisting of HO—, NC—, F, MeO—, EtO—, MeO(O)C—, $Me_2N$(O)C—, Me(O)S—, $Me(O)_2S$—; preferably NC—, F;

oxetanyl, tetrahydropyranyl, tetrahydrofuranyl, dioxanyl, morpholinyl, imidazolidin-2-onyl, pyrrolidin-2-onyl, pyridin-2-onyl;

azetidinyl, pyrrolidinyl, piperidinyl, optionally substituted with methyl, $Me_2N$—$CH_2$—(O)C—;

phenyl, thiophenyl, pyridinyl, pyridazinyl, pyrid-2-onyl pyridin-1-oxidyl, each optionally substituted with methyl, MeO—, $H_3C(O)S$—, $H_3C(O)_2S$—;

imidazolyl, pyrazolyl, oxadiazolyl, isoxazolyl each optionally substituted with methyl;

$R^2$ is $R^{2.1}R^{2.2}R^{2.3}C$—;

$R^{2.1}$ is phenyl, pyridinyl, each optionally substituted with one residue selected from the group consisting of NC—, F—, Cl— in para-position, preferably NC— in para-position and optionally another residue selected from the group consisting of Cl—, F—, MeO—, $Me(O)_2S$—;

$R^{2.2}$ is H;

$R^{2.3}$ is H or methyl;

$R^3$ is methyl;

$R^4$ is phenyl or pyridinyl, each substituted with a residue selected from the group consisting of Me, Cl—, $F_2HC$—, $F_3C$—;

$R^5$ is H;

or a salt thereof.

Also preferred are compounds of formula 1 wherein $R^1$ is $R^{1.1}HN$—, $R^{1.2}HN$—;

$R^{1.1}$ is $C_{3-6}$-cycloalkyl or a four-membered, non-aromatic heteroring, wherein one element is replaced by an O; wherein each element of one of the above mentioned rings is optionally substituted with NC—;

$R^{1.2}$ is a branched or unbranched $C_{1-6}$-alkyl-, optionally substituted independently from each other with one or two residues selected from the group consisting of halogen, NC or a ring selected from $C_{1-6}$-cycloalkyl- or oxadiazolyl; wherein each element of one of the above mentioned rings is optionally substituted with a residue selected from the group consisting of $C_{1-4}$-alkyl-, NC—;

$R^2$ is $R^{2.1}R^{2.2}R^{2.3}C$—;

is $R^{2.1}$ is phenyl or pyridinyl; wherein each element of one of the above mentioned rings is optionally substituted with a residue selected from the group consisting of NC—;

$R^{2.2}$ is H or $C_{1-4}$-alkyl-;

$R^{2.3}$ is H or $C_{1-4}$-alkyl-;

$R^3$ is H or $C_{1-4}$-alkyl-;

$R^4$ is phenyl or pyridinyl; wherein each element of one of the above mentioned rings is optionally substituted with a residue selected from the group consisting of $C_{1-4}$-alkyl-, $C_{1-4}$-alkyl-O—, $C_{1-4}$-haloalkyl-, halogen;

$R^5$ is selected from the group consisting of H, $C_{1-4}$-alkyl-, $C_{1-4}$-haloalkyl- or halogen;

or a salt thereof.

Also preferred are compounds of formula 1 wherein $R^1$ is $R^{1.1}HN$—;

$R^{1.1}$ is $C_{3-6}$-cycloalkyl or a four-membered, non-aromatic heteroring, wherein one element is replaced by an O; wherein each element of one of the above mentioned rings is optionally substituted with NC—;

$R^2$ is $R^{2.1}R^{2.2}R^{2.3}C$—;

$R^{2.1}$ is phenyl or pyridinyl; wherein each element of one of the above mentioned rings is optionally substituted with a residue selected from the group consisting of NC—;

$R^{2.2}$ is H or $C_{1-4}$-alkyl-;

$R^{2.3}$ is H or $C_{1-4}$-alkyl-;

$R^3$ is H or $C_{1-4}$-alkyl-;

$R^4$ is phenyl or pyridinyl; wherein each element of one of the above mentioned rings is optionally substituted with a residue selected from the group consisting of $C_{1-4}$-alkyl-, $C_{1-4}$-alkyl-O—, $C_{1-4}$-haloalkyl-, halogen;

$R^5$ is selected from the group consisting of H, $C_{1-4}$-alkyl-, $C_{1-4}$-haloalkyl- or halogen;

or a salt thereof.

Also preferred are compounds of formula 1 wherein $R^1$ is $R^{1.2}HN$—;

$R^{1.2}$ is a branched or unbranched $C_{1-6}$-alkyl-, optionally substituted independently from each other with one or two residues selected from the group consisting of halogen, NC or a ring selected from $C_{1-6}$-cycloalkyl- or oxadiazolyl; wherein each element of one of the above mentioned rings is optionally substituted with a residue selected from the group consisting of $C_{1-4}$-alkyl-, NC—;

$R^2$ is $R^{2.1}R^{2.2}R^{2.3}C$—;

$R^{2.1}$ is phenyl or pyridinyl; wherein each element of one of the above mentioned rings is optionally substituted with a residue selected from the group consisting of NC—;

$R^{2.2}$ is H or $C_{1-4}$-alkyl-;

$R^{2.3}$ is H or $C_{1-4}$-alkyl-;

$R^3$ is H or $C_{1-4}$-alkyl-;

$R^4$ is phenyl or pyridinyl; wherein each element of one of the above mentioned rings is optionally substituted with a residue selected from the group consisting of $C_{1-4}$-alkyl-, $C_{1-4}$-alkyl-O—, $C_{1-4}$-haloalkyl-, halogen;

$R^5$ is selected from the group consisting of H, $C_{1-4}$-alkyl-, $C_{1-4}$-haloalkyl- or halogen;

or a salt thereof.

Also preferred are compounds of formula 1 wherein $R^1$ is $R^{1.1}HN$—;

$R^{1.1}$ is $C_{3-6}$-cycloalkyl or a four-membered, non-aromatic heteroring, wherein one element is replaced by an O; wherein each element of one of the above mentioned rings is optionally substituted with NC—;

$R^2$ is $R^{2.1}R^{2.2}R^{2.3}C$—;

$R^{2.1}$ is phenyl or pyridinyl; wherein each element of one of the above mentioned rings is optionally substituted with a residue selected from the group consisting of NC—;

$R^{2.2}$ is methyl;

$R^{2.3}$ is H;

$R^3$ is methyl;

$R^4$ is phenyl or pyridinyl; wherein each element of one of the above mentioned rings is optionally substituted with a residue selected from the group consisting of $FH_2C$—, $F_2HC$—, $F_3C$—;

$R^5$ is H;

or a salt thereof.

Also preferred are compounds of formula 1 wherein $R^1$ is $R^{1.2}HN$—;

$R^{1.2}$ is a branched or unbranched $C_{1-6}$-alkyl-, optionally substituted independently from each other with one or two residues selected from the group consisting of halogen, NC or a ring selected from $C_{1-6}$-cycloalkyl- or oxadiazolyl; wherein each element of one of the above mentioned rings is optionally substituted with a residue selected from the group consisting of $C_{1-4}$-alkyl-, NC—;

$R^2$ is $R^{2.1}R^{2.2}R^{2.3}C$—;

$R^{2.1}$ is phenyl or pyridinyl; wherein each element of one of the above mentioned rings is optionally substituted with a residue selected from the group consisting of NC—;

$R^{2.2}$ is methyl;

$R^{2.3}$ is H;

$R^3$ is methyl;

$R^4$ is phenyl or pyridinyl; wherein each element of one of the above mentioned rings is optionally substituted with a residue selected from the group consisting of $FH_2C$—, $F_2HC$—, $F_3C$—;

$R^5$ is H;

or a salt thereof.

Also preferred are compounds of formula 1 wherein $R^1$ is $R^{1.1}HN$—, $R^{1.2}HN$—;

$R^{1.1}$ is cyclopropyl or oxetanyl; wherein each element of one of the above mentioned rings is optionally substituted with NC—;

$R^{1.2}$ is methyl or ethyl, optionally substituted independently from each other with one or two residues selected from the group consisting of halogen, NC or oxadiazolyl, substituted with methyl;

$R^2$ is $R^{2.1}R^{2.2}R^{2.3}C$—;

$R^{2.1}$ is phenyl or pyridinyl; wherein each element of one of the above mentioned rings is optionally substituted with a residue selected from the group consisting of NC—;

$R^{2.2}$ is methyl;

$R^{2.3}$ is H;

$R^3$ is methyl;

$R^4$ is phenyl or pyridinyl; wherein each element of one of the above mentioned rings is optionally substituted with a residue selected from the group consisting of $FH_2C$—, $F_2HC$—, $F_3C$—;

$R^5$ is H;

or a salt thereof.

Also preferred are the above compounds of formula 1, wherein $R^1$ is selected from a group consisting of

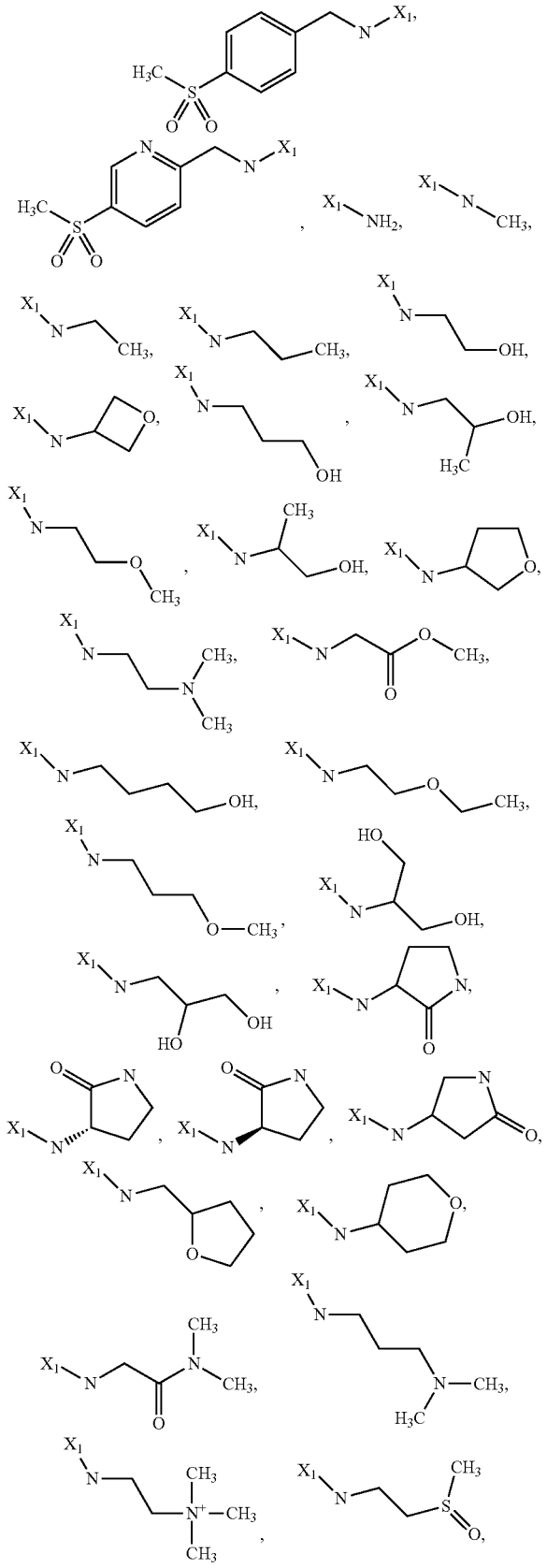

-continued
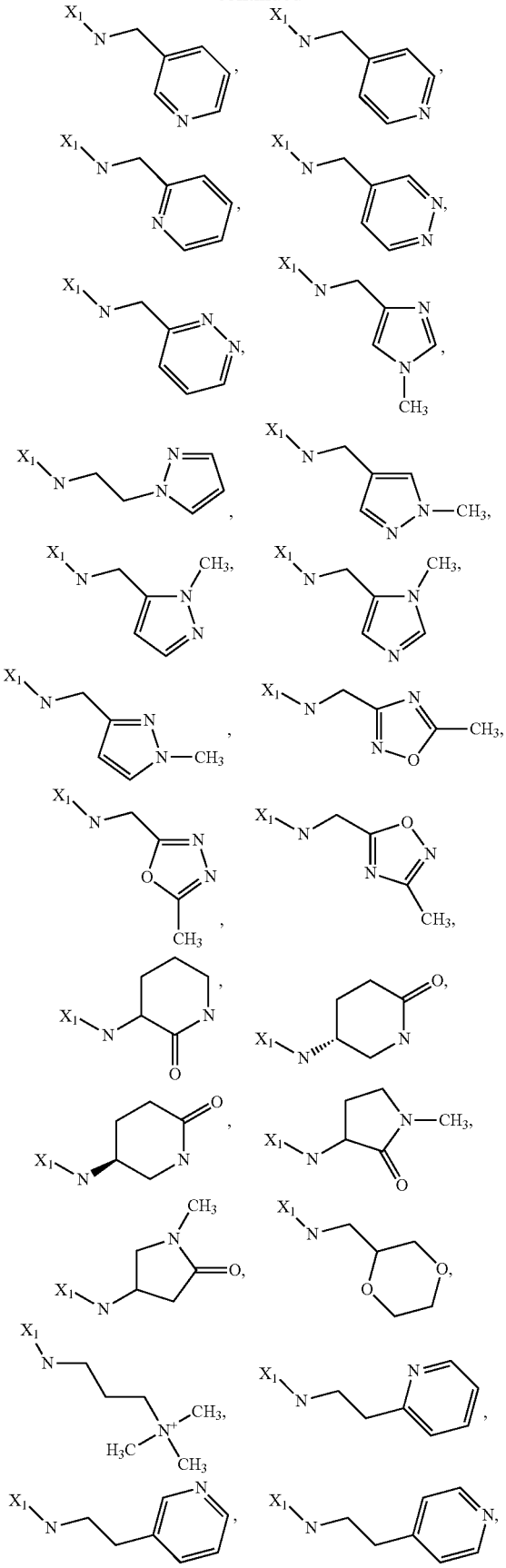
-continued
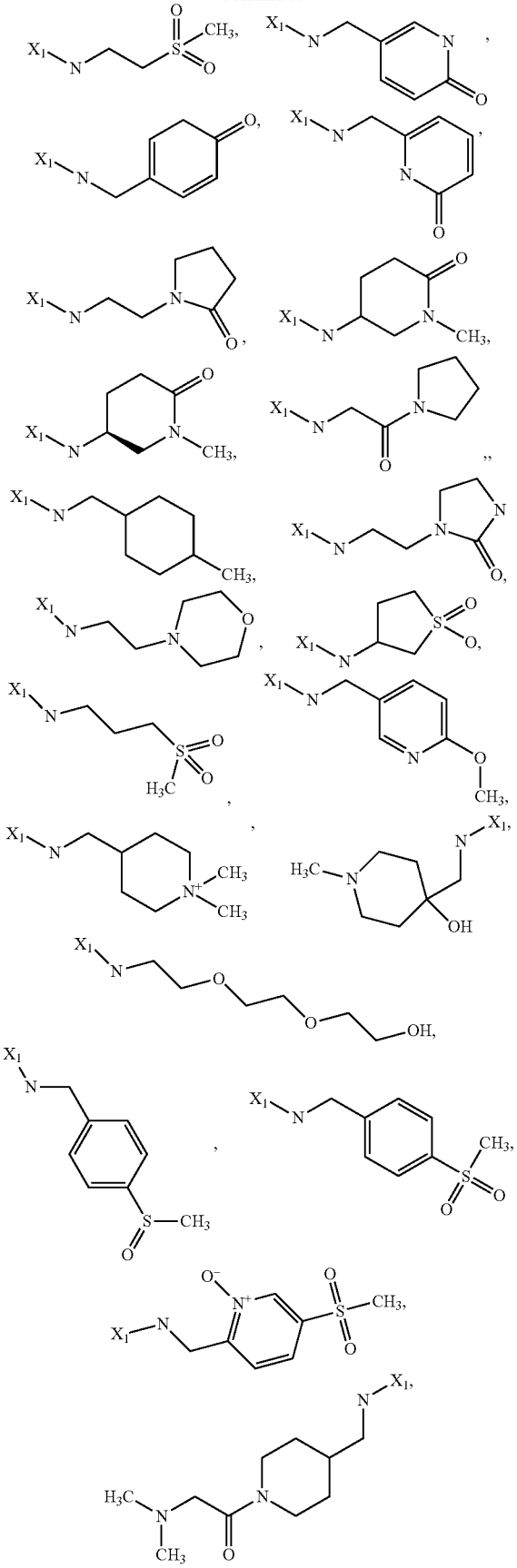

-continued

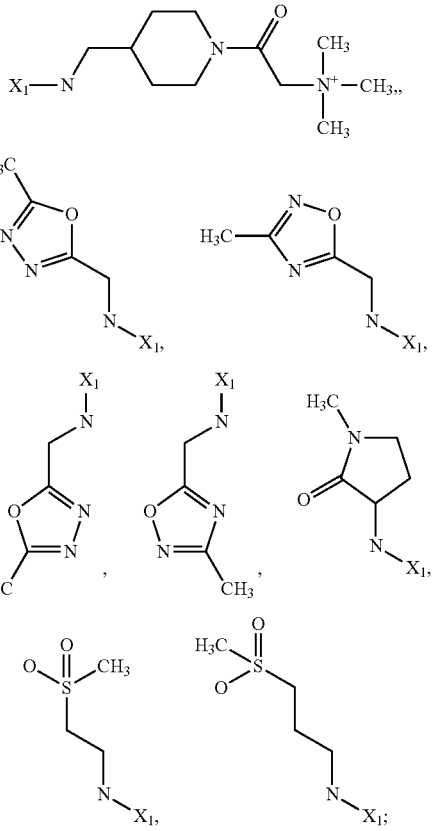

$R^2$ is selected from a group consisting of

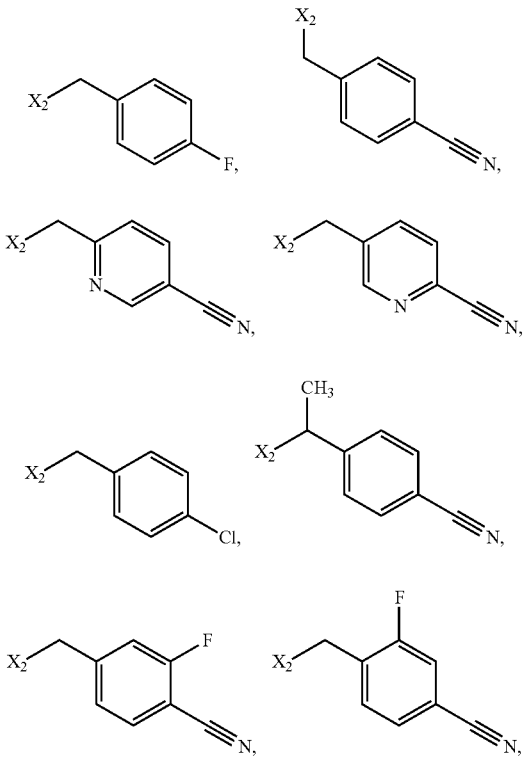

-continued

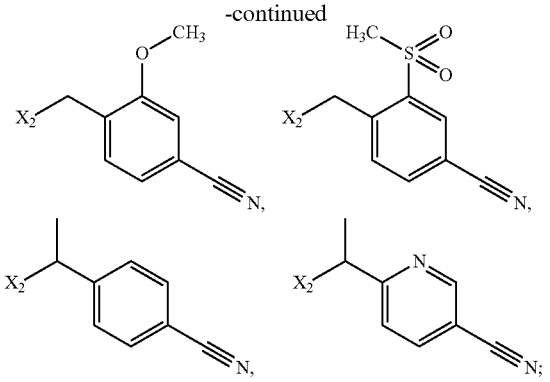

$R^3$ is methyl;

$R^4$ is selected from a group consisting of

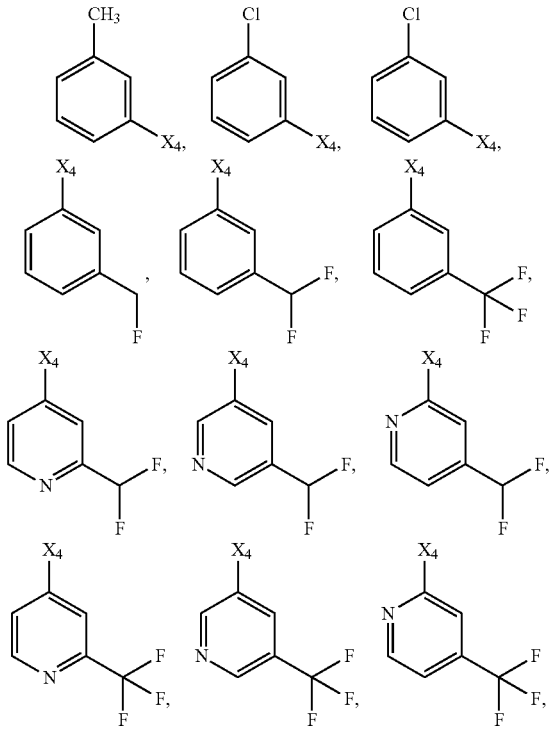

$R^5$ is H;

or a salt thereof.

Also preferred are the above compounds of formula 1, wherein $R^1$ is $R^{1.1}HN$—, $R^{1.2}HN$—;

$R^{1.1}$ is cyclopropyl or oxetanyl; wherein each element of one of the above mentioned rings is optionally substituted with NC—;

$R^{1.2}$ is methyl or ethyl, optionally substituted independently from each other with one or two residues selected from the group consisting of halogen, NC or oxadiazolyl, substituted with methyl;

wherein tertiary amines in principal can also be quaternary together with $(H_3C)^+Y^-$ and Y is an anion; preferably a pharmaceutically acceptable anion; preferably $Cl^-$ $R^2$ is selected from a group consisting of

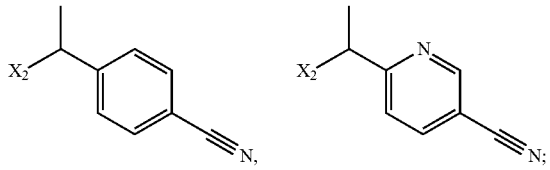

$R^3$ is methyl;

$R^4$ is selected from a group consisting of

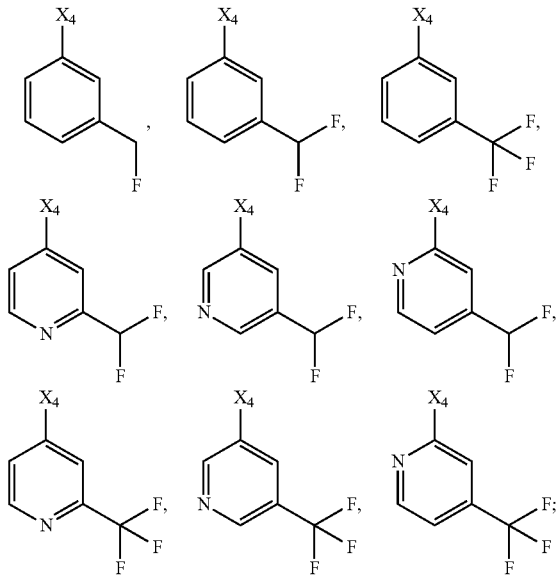

$R^5$ is H;

or a salt thereof.

From the above mentioned compounds those are preferred wherein $R^2$ is

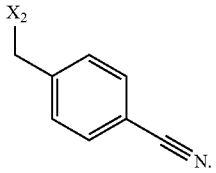

From the above mentioned compounds those are preferred wherein $R^2$ is

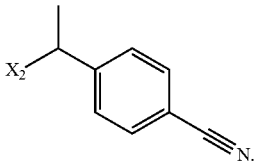

From the above mentioned compounds those are preferred wherein $R^2$ is

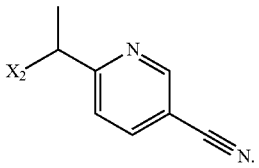

In a preferred embodiment of the invention $R^4$ is one of the above mentioned rings carrying the above mentioned optional substituted in meta-position to the element connection $R^4$ with the compound of formula 1.

From the above mentioned compounds those are preferred wherein $R^4$ is

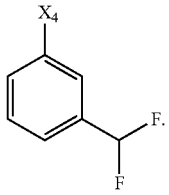

From the above mentioned compounds those are preferred wherein $R^4$ is

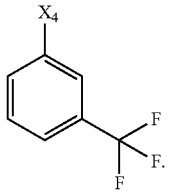

From the above mentioned compounds those are preferred wherein $R^4$ is

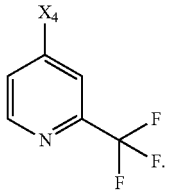

As seen from above the compounds of formula 1 can contain one or more nitrogen atoms and maybe from salts with one or more of them. Thus compounds of formula 1 comprise a pharmaceutically acceptable anion Y associated with the positive charge on a quaternary nitrogen atom. The anion Y may be any pharmaceutically acceptable anion of a mono or polyvalent (e.g. bivalent) acid. As will be realized when Y is polyvalent for example a divalent anion $Y^{2''}$ the compound of formula 1 may form a hemi-salt with the divalent anion of the formula 1

In an embodiment of the invention Y may be an "pharmaceutically acceptable anion" of a mineral acid, preferred are chloride, bromide, iodide, sulfate, nitrate or phosphate; or an anion of a suitable organic acid, for example acetate, maleate, fumarate, citrate, oxalate, succinate, tartrate, saccharinate, cinnamate, mandelate, lactate, malonate, malate, methanesulphonate (mesylate), p-toluenesulphonate, benzenesulfonate, napadisylate (naphthalene-1,5-disulphonate) (e.g. a heminapadisylate), 1-hydroxy-2-naphthoate, 1-hydroxynaphthalene-2-sulphonate. In another embodiment Y represents, for example, halide, acetate, mesylate or benzenesulfonate. In one embodiment of the invention Y represents halide, for example chloride, bromide or iodide. In another embodiment Y represents iodide. In another embodiment Y represents bromide. In another embodiment Y represents chloride. In another embodiment Y represents acetate. In another embodiment Y represents mesylate. In another embodiment Y represents benzenesulfonate (besylate).

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk, a dashed or a dotted line may be used in sub-formulas to indicate the bond which is connected to the core molecule as defined.

For example, the term "3-carboxypropyl-group" represents the following substituent:

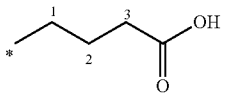

wherein the carboxy group is attached to the third carbon atom of the propyl group. The terms "1-methylpropyl-", "2,2-dimethylpropyl-" or "cyclopropylmethyl-" group represent the following groups:

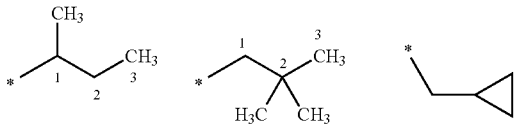

The asterisk, dashed or dotted line may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . .) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylene-diamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethane-sulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 2 to 4 or 6 (preferably 4), either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{2-n}$-alkylene" wherein n is an integer 3 to 5, either alone or in combination with another radical, denotes an acyclic, straight or branched chain divalent alkyl radical containing from 2 to 5 carbon atoms. For example the term $C_{2-5}$-alkylene includes —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "$C_{3-n}$-cycloalkyl", wherein n is an integer from 4 to 6, either alone or in combination with another radical denotes a cyclic, saturated, unbranched hydrocarbon radical with 3 to 6 C atoms. For example the term $C_{3-6}$-cycloalkyl includes cyclopropyl, cyclobutyl, cyclopentyl and cyclohexyl.

By the term "halo" added to a "alkyl", "alkylene" or "cycloalkyl" group (saturated or unsaturated) is such a alkyl or cycloalkyl group meant wherein one or more hydrogen atoms are replaced by a halogen atom selected from among fluorine, chlorine or bromine, preferably fluorine and chlorine, particularly preferred is fluorine. Examples include: $H_2FC$—, $HF_2C$—, $F_3C$—.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

With the elements of a ring the atoms forming this ring are meant. So, a phenyl ring contains 6 elements which are all carbon atoms, a pyrrol ring contains 5 elements, wherein 4 elements are carbon atoms and the remaining element is a nitrogen atom.

The term "non-aromatic heteroring" means a saturated, partially saturated or unsaturated monocyclic-ring systems containing one, two, three or four heteroatoms selected from N, $(O^-)N^+$, 0 or $(O)_rS$, wherein r=0, 1 or 2, consisting of four, five or six ring atoms. If the term is connected with a more detailed definition of the amount or kind of heteroatoms and the possible size of the non-aromatic heteroring, the detailed definition is restricting the above mentioned definition.

Furthermore the term is intended to include all possible isomeric forms. Thus, the term includes (if not otherwise restricted) the following exemplary structures which are not depicted as radicals as each form may be attached through a covalent bond to any atom so long as appropriate valences are maintained:

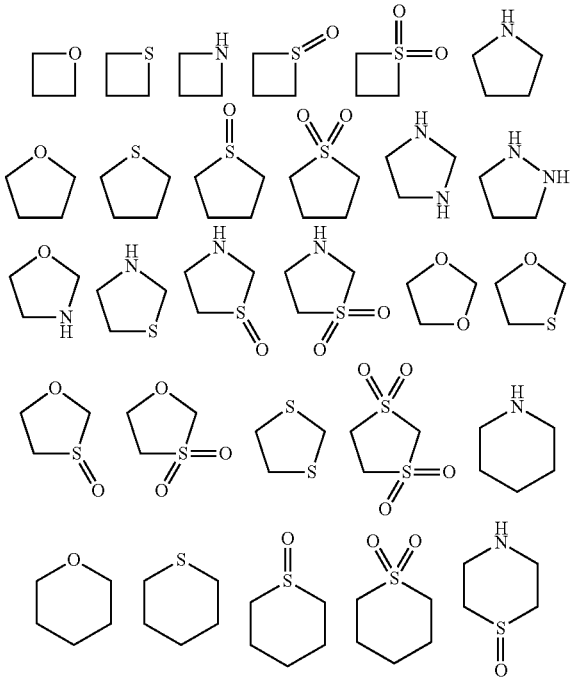

-continued

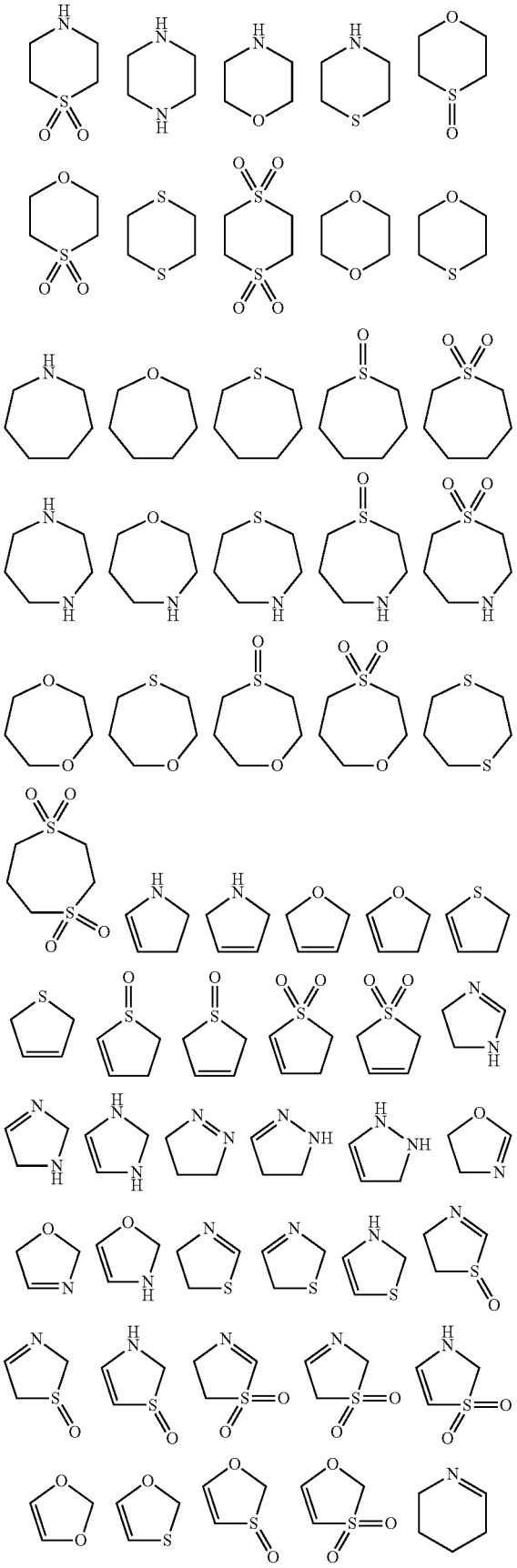

-continued

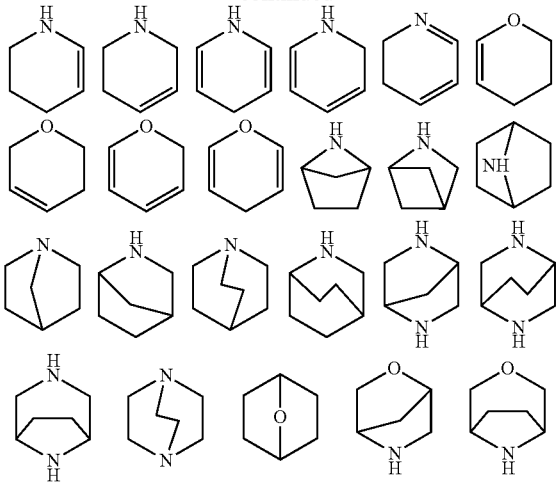

The term "aromatic heteroring" means a unsaturated monocyclic-ring systems containing one, two, three or four heteroatoms selected from N, $(O^-)N^+$, O or $(O)_rS$, wherein r=0, 1 or 2, consisting of four, five or six ring atoms. If the term is connected with a more detailed definition of the amount or kind of heteroatoms and the possible size of the aromatic heteroring, the detailed definition is restricting the above mentioned definition.

Furthermore the term is intended to include all possible isomeric forms. Thus, the term includes (if not otherwise restricted) the following exemplary structures which are not depicted as radicals as each form may be attached through a covalent bond to any atom so long as appropriate valences are maintained:

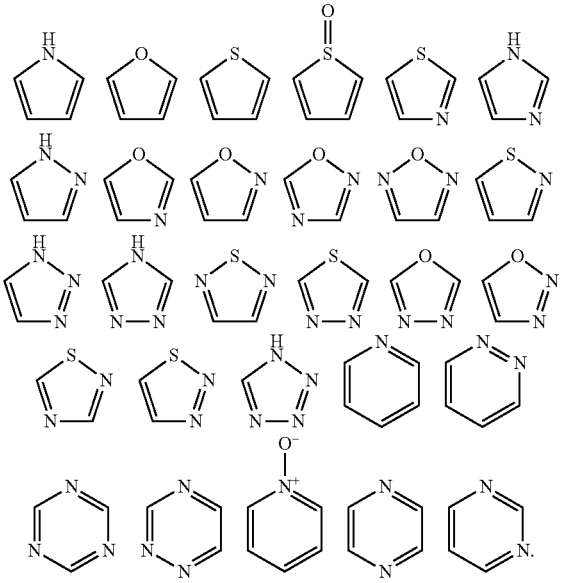

The term "ring system of two fused aromatic or non-aromatic heterorings" means a saturated or unsaturated polycyclic-ring systems including aromatic heteroring system containing one or more heteroatoms selected from N, O or $S(O)_r$, wherein r=0, 1 or 2, consisting of 8 to 14 ring atoms, preferably 8 to 10 ring atoms, wherein none of the heteroatoms is part of the aromatic heteroring. If the term is connected with a more detailed definition of the amount or kind of heteroatoms and the possible size of the aromatic heteroring, the detailed definition is restricting the above mentioned definition.

Furthermore the term is intended to include all possible isomeric forms. Thus, the term includes (if not otherwise restricted) the following exemplary structures which are not depicted as radicals as each form may be attached through a covalent bond to any atom so long as appropriate valences are maintained:

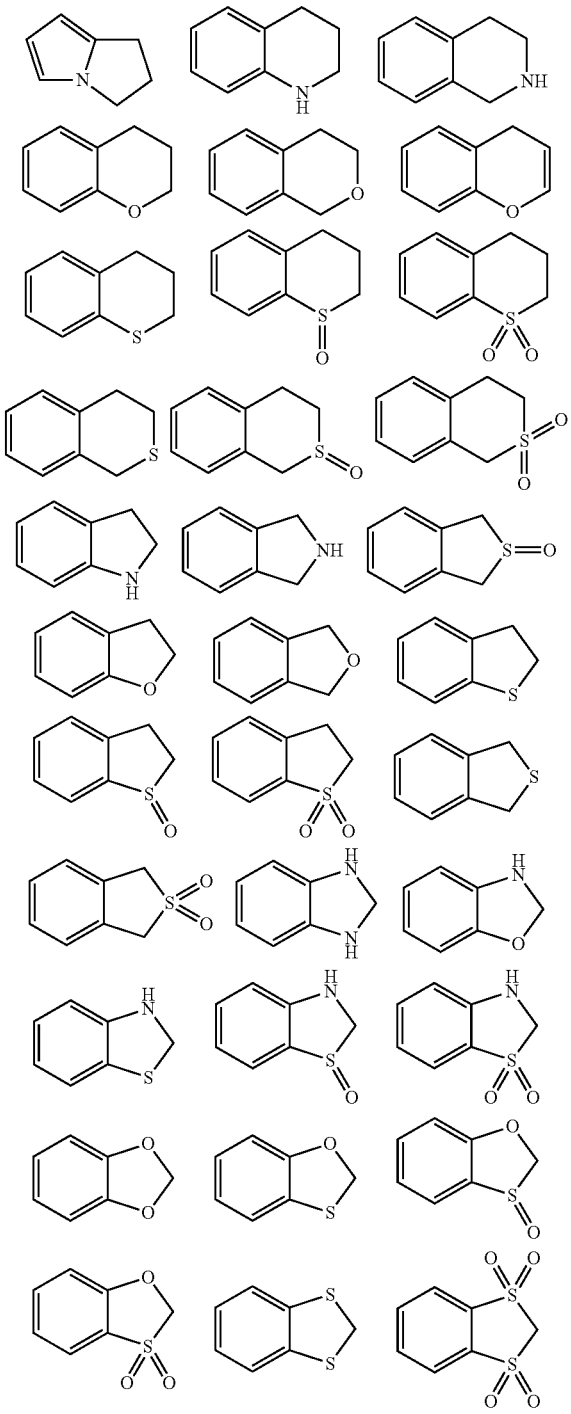

-continued

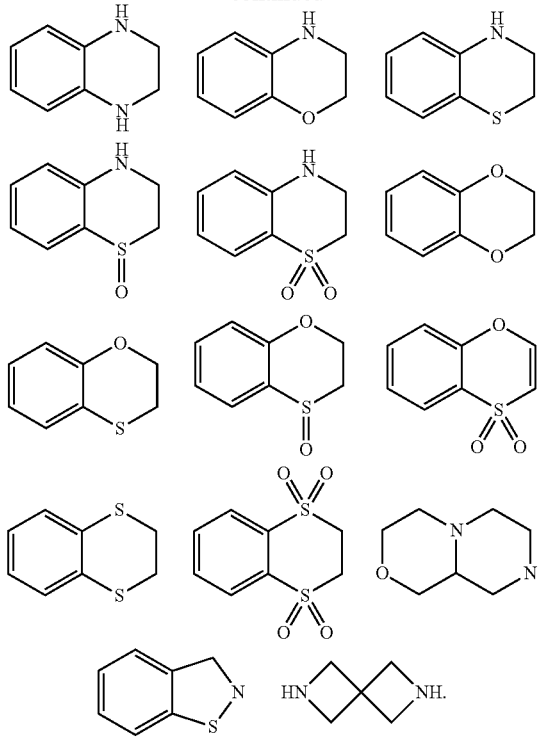

The following examples are also part of the term group defined with the term "ring system of two fused aromatic or non-aromatic heterorings", but are also a subgroup called "ring system of two fused aromatic heterorings"

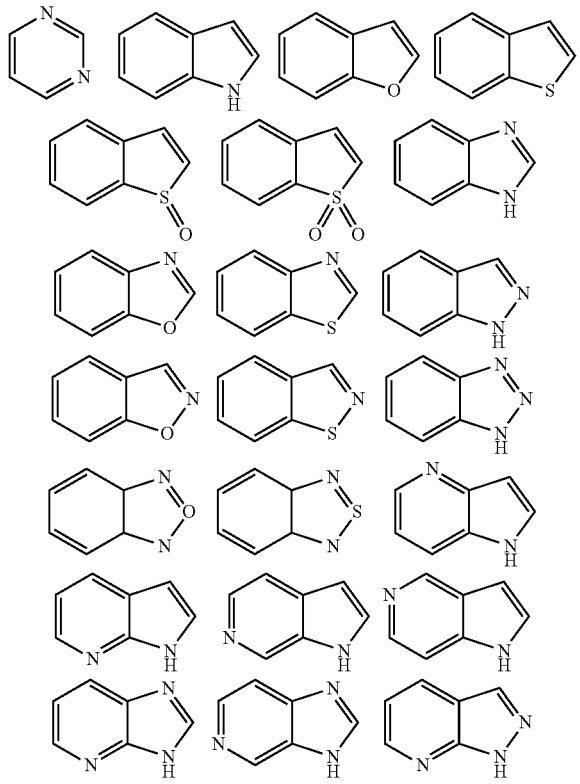

-continued

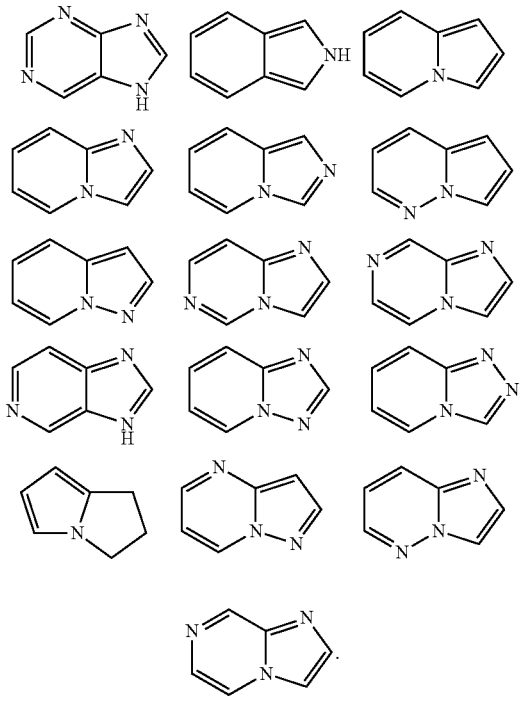

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes. Starting materials are commercially available or may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

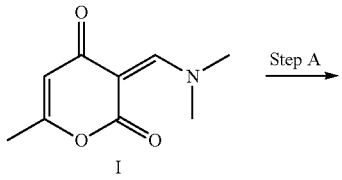

-continued

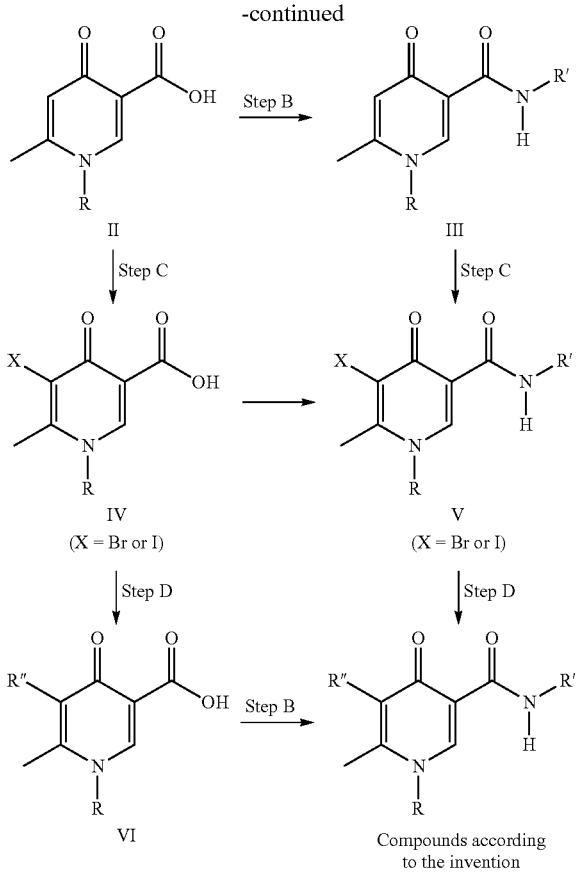

Starting material I can be prepared as described in US2003/87940.

Intermediates II can be prepared as described in WO10133973 and US2003/87940 by heating starting material I with amines R—$NH_2$ in the presence of a strong base, for example sodium tert-butoxide or sodium ethoxide, in an organic solvent, for example ethanol. The reaction usually takes place within 2 to 72 hours. Preferred reaction temperatures are between 50° C. and 150° C.

The amide coupling (Step B, intermediates II→intermediates III, intermediates IV→intermediates V, intermediates VI→compounds of the invention) can be achieved by reacting carboxylic acid intermediates II, IV or VI with amines R'—$NH_2$ in the presence of an amide coupling reagent, for example O-(Benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), 1-propanephosphonic acid cyclic anhydride (PPA) or O-(Benzotriazol-1-yl)-N,N,N',N'-tetramethyluronium tetrafluoroborate (TBTU), and in the presence of a base, for example triethylamine, diisopropyl-ethylamine (DIPEA, Hünig's base) or N-methyl-morpholine, in an organic solvent, for example N,N-dimethylformamide (DMF), N-methyl-2-pyrrolidone (NMP), dichloromethane, acetonitrile or dimethylacetamide (DMA) or mixtures thereof. The reaction usually takes place within 1 to 72 hours. Preferred reaction temperatures are between 0° C. and 50° C., most preferred room temperature. Alternatively, the carboxylic acid intermediates can be activated first as described in US2003/87940, for example with 1,1'-carbonyldiimidazole (CDI) in DMF, followed by reaction with the amine R'—$NH_2$.

The bromination (Step C, X=Br, intermediates II→intermediates IV, intermediates III→intermediates V) can be achieved by reacting intermediates II or III with bromination agents, for example bromine or N-bromosuccinimide, in an organic solvent, for example acetic acid, dichloromethane, methanol, acetonitrile, tetrahydrofuran or mixtures thereof. The iodination (Step C, X=I, intermediates II→intermediates IV, intermediates III→intermediates V) can be achieved by reacting intermediates II or III with iodination agents, for example iodine, iodinechloride (I—Cl) or N-iodosuccinimide, in an organic solvent, for example acetic acid, methanol, ethanol, dichloromethane, acetonitrile, N,N-dimethylformamide, tetrahydrofuran or mixtures thereof. The halogenation reaction usually takes place within 1 to 72 hours. Preferred reaction temperatures are between 0° C. and 50° C., most preferred room temperature.

The Suzuki coupling (Step D, intermediates IV→intermediates VI, intermediates V→compounds according to the invention) can be achieved by reacting intermediates IV or V with aryl or heteroaryl boronic acids R"—B $(OH)_2$ or the corresponding boronic esters in the presence of a palladium catalyst, for example tetrakis(triphenylphosphine)palladium (0) or [1,1'-bis(diphenylphosphino)ferrocene]dichloropalladium(II), and in the presence of a base, for example, potassium carbonate, barium dihydroxide or cesium carbonate, in an organic solvent, for example toluene, benzene, ethanol, ethylene glycol dimethyl ether, acetonitrile, dioxane or mixtures thereof, optionally in the presence of water. The reaction usually takes place within 1 to 72 hours. Preferred reaction temperatures are between 50° C. and 150° C.

Compounds according to the present invention can also be prepared according to the following scheme starting from 4-hydroxy-6-methyl-nicotinic acid. Halogenation (Step C) as described above, followed by Suzuki coupling (Step D) as described above, followed by amide coupling (Step B) as described above, yields intermediates VII. The alkylation of the pyridone nitrogen (Step E) can be achieved by reacting intermediate VII with alkylating agents, for example alkyl bromides, alkyl iodides, alkyl tosylates, alkyl mesylates or dialkyl sulfates, in the presence of a base, for example sodium carbonate, potassium carbonate, potassium hydroxide, sodium hydroxide or cesium carbonate, in an organic solvent, N,N-dimethylformamide (DMF), N-methyl-2-pyrrolidone (NMP) or dimethylacetamide (DMA). The reaction usually takes place within 1 to 72 hours. Preferred reaction temperatures are between 50° C. and 150° C.

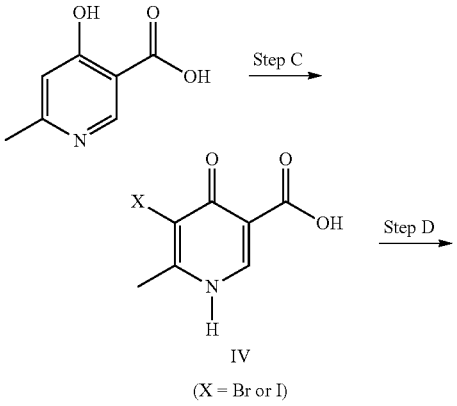

-continued

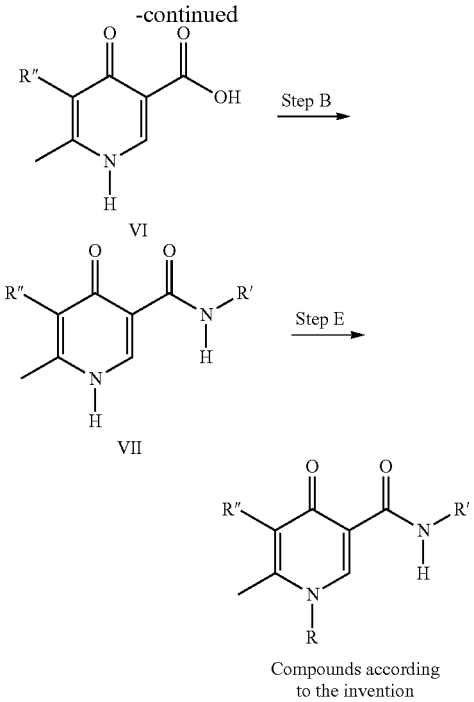

The intermediates for compounds according to the present invention with 2-alkyl substituents can be prepared according to Venkatramani et al., J. Het. Chem. 30, 723-738 (1993).

Preliminary Remarks:

The HPLC data given are measured under the following conditions:

| Method Name: | V003_003 | | | |
|---|---|---|---|---|
| Column: | XBridge C18, 4.6 × 30 mm, 3.5 μm | | | |
| Column Supplier: | Waters | | | |
| Gradient/Solvent Time [min] | % Sol [H2O, 0.1% $NH_4OH$] | % Sol [Methanol] | Flow [ml/min] | Temp [° C.] |
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

| Method Name: | Z002_002 | | | |
|---|---|---|---|---|
| Column: | Sunfire C18, 3 × 30 mm, 2.5 μm | | | |
| Column Supplier: | Waters | | | |
| Gradient/Solvent Time [min] | % Sol [H2O, 0.1% TFA] | % Sol [Methanol] | Flow [ml/min] | Temp [° C.] |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method Name: | Z002_005 | | | |
|---|---|---|---|---|
| Column: | Sunfire C18, 3 × 30 mm, 2.5 μm | | | |
| Column Supplier: | Waters | | | |
| Gradient/Solvent Time [min] | % Sol [H2O, 0.1% TFA] | % Sol [Methanol] | Flow [ml/min] | Temp [° C.] |
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

| Method Name: | Z002_007 | | | |
|---|---|---|---|---|
| Column: | Sunfire C18, 3 × 30 mm, 2.5 μm | | | |
| Column Supplier: | Waters | | | |
| Gradient/Solvent Time [min] | % Sol [H2O, 0.1% TFA] | % Sol [Methanol] | Flow [ml/min] | Temp [° C.] |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method Name: | Z003_001 | | | |
|---|---|---|---|---|
| Column: | XBridge C18, 3 × 30 mm, 2.5 μm | | | |
| Column Supplier: | Waters | | | |
| Gradient/Solvent Time [min] | % Sol [H2O, 0.1% $NH_4OH$] | % Sol [Methanol] | Flow [ml/min] | Temp [° C.] |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method Name: | Z003_003 | | | |
|---|---|---|---|---|
| Column: | XBridge C18, 3 × 30 mm, 2.5 μm | | | |
| Column Supplier: | Waters | | | |
| Gradient/Solvent Time [min] | % Sol [H2O, 0.1% $NH_4OH$] | % Sol [Methanol] | Flow [ml/min] | Temp [° C.] |
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.70 | 0 | 100 | 2.9 | 60 |

| Method Name: | Z011_S03 | | | |
|---|---|---|---|---|
| Column: | XBridge C18, 3 × 30 mm, 2.5 μm | | | |
| Column Supplier: | Waters | | | |
| Gradient/Solvent Time [min] | % Sol [H2O, 0.1% $NH_4OH$] | % Sol [Aceto-nitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z018_S04 | | | |
|---|---|---|---|---|
| Column: | Sunfire, 3 × 30 mm, 2.5 μm | | | |
| Column Supplier: | Waters | | | |
| Gradient/Solvent Time [min] | % Sol [H2O, 0.1% TFA] | % Sol [Aceto-nitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

-continued

Method Name: 001_CA04
Column: XBridge C18_4.6 × 30 mm, 3.5 μm
Column Supplier: Waters

| Gradient/Solvent Time [min] | % Sol [H2O, 0.1% $NH_4OH$] | % Sol [Methanol] | Flow [ml/min] | Temp [° C.] |
|---|---|---|---|---|
| 0.0 | 80 | 20 | 2.0 | 60 |
| 1.7 | 0 | 100 | 2.0 | 60 |
| 2.5 | 0 | 100 | 2.0 | 60 |

Method Name: 002_CA04
Column: XBridge C18_4.6 × 30 mm, 3.5 μm
Column Supplier: Waters

| Gradient/Solvent Time [min] | % Sol [H2O, 0.1% $NH_4OH$] | % Sol [Aceto-nitrile] | Flow [ml/min] | Temp [° C.] |
|---|---|---|---|---|
| 0.0 | 98 | 2 | 2.5 | 60 |
| 1.5 | 0 | 100 | 2.5 | 60 |
| 1.8 | 0 | 100 | 2.5 | 60 |

Method Name: 004_CA05
Column: XBridge C18_3.0 × 30 mm, 2.5 μm
Column Supplier: Waters

| Gradient/Solvent Time [min] | % Sol [H2O, 0.1% $NH_4OH$] | % Sol [Aceto-nitrile] | Flow [ml/min] | Temp [° C.] |
|---|---|---|---|---|
| 0.0 | 98 | 2 | 2.0 | 60 |
| 1.2 | 0 | 100 | 2.0 | 60 |
| 1.4 | 0 | 100 | 2.0 | 60 |

Method Name: 004_CC_ZQ4
Column: Sunfire C18_4.6 × 50 mm, 3.5 μm
Column Supplier: Waters

| Gradient/Solvent Time [min] | % Sol [H2O, 0.1% TFA] | % Sol [Methanol] | Flow [ml/min] | Temp [° C.] |
|---|---|---|---|---|
| 0.0 | 80 | 20 | 2.0 | 60 |
| 1.7 | 0 | 100 | 2.0 | 60 |
| 2.5 | 0 | 100 | 2.0 | 60 |
| 2.6 | 80 | 20 | 2.0 | 60 |

Method Name: 015_CC_SQD1
Column: BEH C18_2.1 × 30 mm, 1.7 μm
Column Supplier: Waters

| Gradient/Solvent Time [min] | % Sol [H2O, 0.1% NH,OH] | % Sol [Aceto-nitrile] | Flow [ml/min] | Temp [° C.] |
|---|---|---|---|---|
| 0.0 | 95.0 | 5.0 | 1.5 | 60 |
| 0.8 | 0.1 | 99.9 | 1.5 | 60 |
| 0.9 | 0.1 | 99.9 | 1.5 | 60 |

Method Name: Z002_006
Column: Sunfire C18, 3 × 30 mm, 2.5 μm
Column Supplier: Waters

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

-continued

Method Name: 005_CA01
Column: Sunfire C18_3.0 × 30 mm, 2.5 μm
Column producer: Waters

| Gradient/Solvent Time [min] | % Sol [H2O, 0.1% TFA] | % Sol [Aceto-nitrile] | Flow [ml/min] | Temp [° C.] |
|---|---|---|---|---|
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

Method Name: 002_CA03
Column: Sunfire C18_3.0 × 30 mm, 2.5 μm
Column producer: Waters

| Gradient/Solvent Time [min] | % Sol [H2O, 0.1% TFA] | % Sol [Aceto-nitrile] | Flow [ml/min] | Temp [° C.] |
|---|---|---|---|---|
| 0.0 | 99.0 | 1.0 | 2.0 | 60.0 |
| 0.9 | 0.0 | 100.0 | 2.0 | 60.0 |
| 1.1 | 0.0 | 100.0 | 2.0 | 60.0 |

Method Name: 001_CA07
Column: Sunfire C18 2.1 × 50 mm, 2.5 μm
Column producer: Waters

| Gradient/Solvent Time [min] | % Sol [H2O, 0.1% TFA] | % Sol [Acetonitrile 0.08% TFA] | Flow [ml/min] | Temp [° C.] |
|---|---|---|---|---|
| 0.0 | 95.0 | 5.0 | 1.5 | 60.0 |
| 0.75 | 0.0 | 100.0 | 1.5 | 60.0 |
| 0.85 | 0.0 | 100.0 | 1.5 | 60.0 |

Method Name: Z012_S04
Column: XBridge C18, 3 × 30 mm, 2.5 μm
Column Supplier: Waters

| Gradient/Solvent Time [min] | % Sol [H2O, 0.1% TFA] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z017_S04
Column: Stable Bond, 3 × 30 mm, 1.8 μm
Column Supplier: Agilent

| Gradient/Solvent Time [min] | % Sol [H2O, 0.1% TFA] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Preparation 1: 1-(4-Cyano-benzyl)-6-methyl-4-oxo-5-(3-trifluoromethyl-phenyl)-1,4-dihydro-pyridine-3-carboxylic acid

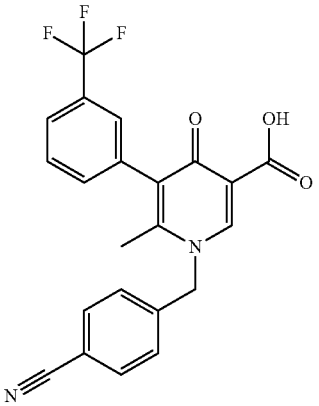

3-Dimethylaminomethylene-6-methyl-pyran-2,4-dione

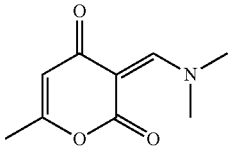

To a solution of 4-hydroxy-6-methyl-2-pyrone (11.50 g, 91.2 mmol) in toluene (30 mL) is added N,N-dimethylformamide dimethyl acetal (13.00 mL, 97.9 mmol). After stirring for 2 h at room temperature, the reaction mixture is evaporated under reduced pressure and co-evaporated with toluene several times. Yield: 18.5 g; ESI mass spectrum: $[M+H]^+$=182; Retention time HPLC: 0.72 min (Z002_007).

1b 1-(4-Cyano-benzyl)-6-methyl-4-oxo-1,4-dihydro-pyridine-3-carboxylic acid

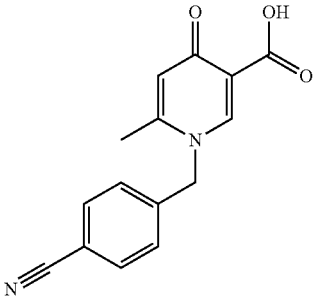

A solution of 3-dimethylaminomethylene-6-methyl-pyran-2,4-dione (preparation 1a, 2.00 g, 9.38 mmol based on 85% purity), 4-cyanobenzylamine hydrochloride (4.00 mL, 23.7 mmol) and sodium tert-butoxide (2.74 g, 28.5 mmol) in ethanol (11 mL) is heated for 48 h at 90° C. The reaction mixture is acidified with 4N aqueous HCl and extracted several times with dichloromethane. The combined organic layer is dried over $Na_2SO_4$, evaporated under reduced pressure and purified by preparative reversed-phase HPLC (Sunfire, gradient of methanol in water, 0.1% TFA, 60° C.). Yield: 0.94 g (37% of theory); ESI mass spectrum: $[M+H]^+$=269; Retention time HPLC: 0.86 min (Z002_005).

1c 5-Bromo-1-(4-cyano-benzyl)-6-methyl-4-oxo-1,4-dihydro-pyridine-3-carboxylic acid

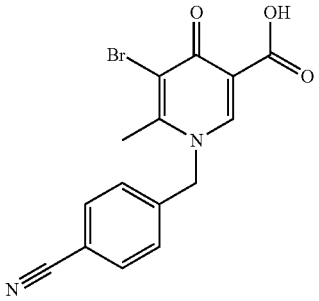

To a solution of 1-(4-cyano-benzyl)-6-methyl-4-oxo-1,4-dihydro-pyridine-3-carboxylic acid (preparation 1b, 12.9 g, 48.2 mmol) in glacial acetic acid (50 ml) is added at room temperature bromine (5.0 mL). The reaction mixture is stirred for 1 day at room temperature, then additional bromine (3.0 mL) is added. After stirring for an additional 4 days at room temperature, water is added to the reaction mixture and the formed precipitate is filtered off and dried. Yield: 14.0 g (84% of theory); ESI mass spectrum: $[M+H]^+$=347 (bromine isotope pattern); Retention time HPLC: 1.07 min (Z002_005).

1d 1-(4-Cyano-benzyl)-6-methyl-4-oxo-5-(3-trifluoromethyl-phenyl)-1,4-dihydro-pyridine-3-carboxylic acid

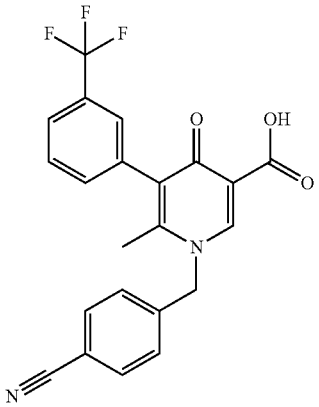

A mixture of 5-bromo-1-(4-cyano-benzyl)-6-methyl-4-oxo-1,4-dihydro-pyridine-3-carboxylic acid (preparation 1c, 2.55 g, 7.34 mmol), 3-(trifluoromethyl)phenylboronic acid (1.65 g, 8.69 mmol), 1,1'-[bis(diphenylphosphino)ferrocene] dichloropalladium(II) (340 mg, 0.47 mmol) and $Cs_2CO_3$ (4.20 g, 12.9 mmol) in dioxane (20.0 mL) is heated for 72 h at 80° C. The reaction mixture is filtered over silica, the filtrate is concentrated under reduced pressure and purified by preparative reversed-phase HPLC (first purification: Sunfire, gradient of methanol in water, 0.1% TFA; second purification: Xbridge, gradient of methanol in water, 0.1% $NH_4OH$, 60° C.). Yield: 514 mg (17% of theory); ESI mass spectrum: $[M+H]^+$=413; Retention time HPLC: 1.37 min (Z002_005).

Preparation 2: 1-[1-(4-Cyano-phenyl)-ethyl]-6-methyl-4-oxo-5-(3-trifluoromethyl-phenyl)-1,4-dihydro-pyridine-3-carboxylic acid

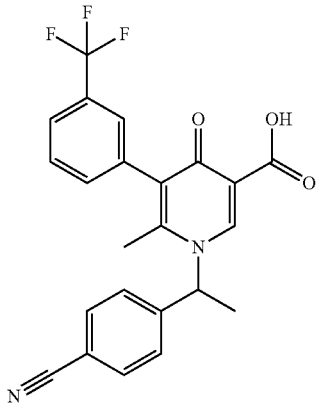

2a 1-[1-(4-Cyano-phenyl)-ethyl]-6-methyl-4-oxo-1,4-dihydro-pyridine-3-carboxylic acid

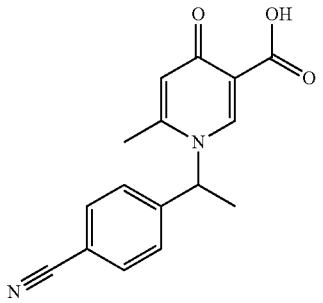

Preparation 2a is prepared following the procedure described for preparation 1b, substituting 4-cyanobenzylamine hydrochloride with 4-(1-aminoethyl)benzonitrile. ESI mass spectrum: $[M+H]^+$=283; Retention time HPLC: 0.78 min (Z018_S04).

2b 5-Bromo-1-[1-(4-cyano-phenyl)-ethyl]-6-methyl-4-oxo-1,4-dihydro-pyridine-3-carboxylic acid

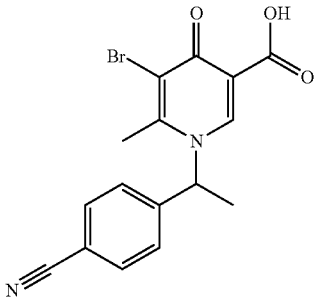

Preparation 2b is prepared following the procedure described for preparation 1c, substituting preparation 1b with preparation 2a as starting material. ESI mass spectrum: $[M+H]^+$=361 (bromine isotope pattern); Retention time HPLC: 0.91 min (Z018_S04).

2c 1-[1-(4-Cyano-phenyl)-ethyl]-6-methyl-4-oxo-5-(3-trifluoromethyl-phenyl)-1,4-dihydro-pyridine-3-carboxylic acid

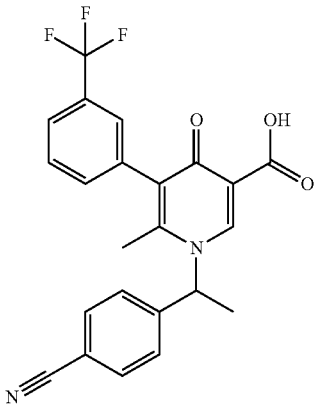

Preparation 2c is prepared following the procedure described for preparation 1d, substituting preparation 1c with preparation 2b as starting material. ESI mass spectrum: $[M+H]^+$=427; Retention time HPLC: 1.07 min (Z018_S04).

Preparation 3: 1-[1-(4-Cyano-phenyl)-ethyl]-5-(3-difluoromethyl-phenyl)-6-methyl-4-oxo-1,4-dihydro-pyridine-3-carboxylic acid

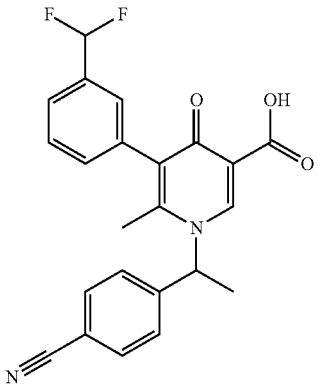

Preparation 3 is prepared following the procedure described for preparation 1d, substituting 3-(trifluoromethyl) phenylboronic acid with 2-(difluoromethyl)phenylboronic acid and substituting preparation 1c with preparation 2b as starting material. ESI mass spectrum: $[M+H]^+$=409; Retention time HPLC: 1.00 min (Z018_S04).

Preparation 4: 1-[1-(4-Cyano-phenyl)-ethyl]-2-methyl-4-oxo-2'-trifluoromethyl-1,4-dihydro-[3,4'] bipyridinyl-5-carboxylic acid

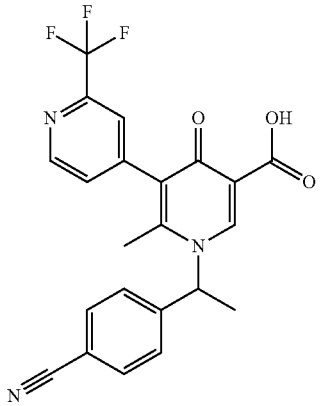

Preparation 4 is prepared following the procedure described for preparation 1d, substituting 3-(trifluoromethyl) phenylboronic acid with 2-(trifluoromethyl)pyridine-4-boronic acid and substituting preparation 1c with preparation 2b as starting material. ESI mass spectrum: $[M+H]^+$=428; Retention time HPLC: 0.99 min (Z018_S04).

Preparation 5: 6-Methyl-4-oxo-5-(3-trifluoromethyl-phenyl)-1,4-dihydro-pyridine-3-carboxylic acid 4-methanesulfonyl-benzylamide

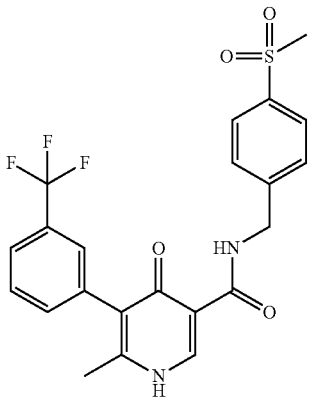

5a 5-Bromo-6-methyl-4-oxo-1,4-dihydro-pyridine-3-carboxylic acid

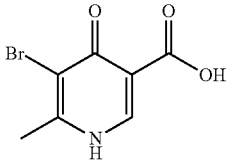

To a solution of 4-hydroxy-6-methyl-nicotinic acid (10.00 g, 65.3 mmol) in glacial acetic acid (35 mL) is added bromine (4.00 mL, 78.1 mmol). After stirring for 18 h at room temperature, additional bromine (0.5 mL) is added and the reaction mixture is stirred for an additional 24 h. The reaction mixture is evaporated under reduced pressure and the remaining residue is co-evaporated with toluene. The remaining residue is treated with a small amount of MeOH and then triturated with water. The precipitate is filtered off and dried. Yield: 13.8 g (92% of theory); ESI mass spectrum: $[M+H]^+$=232 (bromine isotope pattern); Retention time HPLC: 0.61 min (Z002_002).

5b 6-Methyl-4-oxo-5-(3-trifluoromethyl-phenyl)-1,4-dihydro-pyridine-3-carboxylic acid

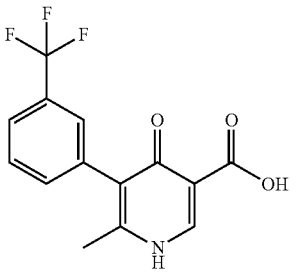

To a solution of 5-bromo-6-methyl-4-oxo-1,4-dihydro-pyridine-3-carboxylic acid (preparation 5a, 12.05 g, 51.9 mmol), 3-(trifluoromethyl)phenylboronic acid (13.6 g, 71.6 mmol), 1,1'-[bis(diphenylphosphino)ferrocene]dichloropalladium(II) (3.60 g, 4.92 mmol) in acetonitrile (100 mL) is added 2 M aqueous $K_2CO_3$ solution (47 mL, 94 mmol). After stirring for 6 h at 75° C., the reaction mixture is filtered and the filtrate is concentrated under reduced pressure. The resulting residue is dissolved in dichloromethane and extracted several times with water. The combined aqueous layer is acidified with 4 N aqueous HCl. The formed precipitate is filtered off, washed with 50 mL hexanes/ethyl acetate (4:1) and dried. Yield: 13.5 g (88% of theory); ESI mass spectrum: $[M+H]^+$=298; Retention time HPLC: 0.80 min (Z003_001).

5c 6-Methyl-4-oxo-5-(3-trifluoromethyl-phenyl)-1,4-dihydro-pyridine-3-carboxylic acid 4-methanesulfonyl-benzylamide

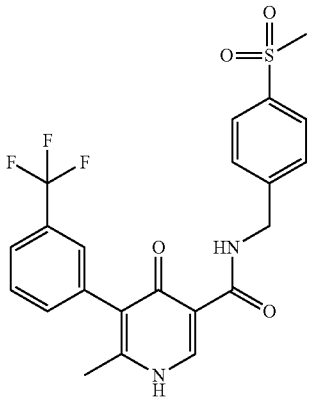

A solution of 6-methyl-4-oxo-5-(3-trifluoromethyl-phenyl)-1,4-dihydro-pyridine-3-carboxylic acid (preparation 5b, 3.00 g, 10.1 mmol), HBTU (4.00 g, 10.5 mmol), DIPEA (5.00 mL, 29.4 mmol) in NMP (15 mL) is stirred for 30 min. Then, 4-methylsulfonylbenzylamine hydrochloride (2.46 g, 11.1 mmol) is added and the reaction mixture is stirred for 72 h at room temperature. Water is added to the reaction mixture. The formed gummy precipitate is dissolved in MeOH and purified by preparative reversed-phase HPLC (Gilson, XBridge, gradient of methanol in water, 0.3% $NH_4OH$, 60° C.). Yield: 1.50 g (32% of theory); ESI mass spectrum: $[M+H]^+$=465; Retention time HPLC: 0.89 min (Z003_001).

Preparation 6: 6-Methyl-4-oxo-5-(3-trifluoromethyl-phenyl)-1,4-dihydro-pyridine-3-carboxylic acid methylamide

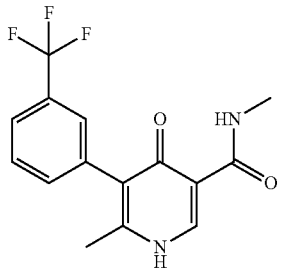

A solution of 6-methyl-4-oxo-5-(3-trifluoromethyl-phenyl)-1,4-dihydro-pyridine-3-carboxylic acid (preparation 5b, 0.800 g, 2.69 mmol), HBTU (1.07 g, 2.81 mmol), DIPEA (0.78 mL, 4.59 mmol) in NMP (5 mL) is stirred for 30 min. Then, methylamine (5.00 mL of 2M solution in THF, 10.0 mmol) is added and the reaction mixture is stirred for 18 h at room temperature. The reaction mixture is concentrated under reduced pressure and purified by preparative reversed-phase HPLC (XBridge, gradient of methanol in water, 0.3% $NH_4OH$, 60° C.). Yield: 0.20 g (24% of theory); ESI mass spectrum: $[M+H]^+$=311; Retention time HPLC: 1.10 min (V003_003).

Preparation 7: 6-Methyl-4-oxo-5-(3-trifluoromethyl-phenyl)-1,4-dihydro-pyridine-3-carboxylic acid (5-methanesulfonyl-pyridin-2-ylmethyl)-amide

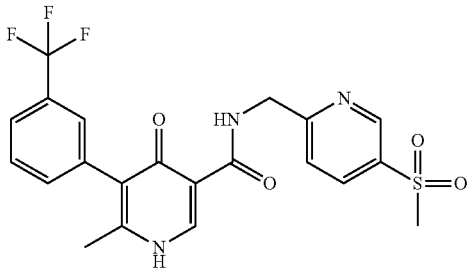

A solution of 6-methyl-4-oxo-5-(3-trifluoromethyl-phenyl)-1,4-dihydro-pyridine-3-carboxylic acid (preparation 5b, 0.800 g, 2.69 mmol), HBTU (1.07 g, 2.81 mmol), DIPEA (1.37 mL, 8.08 mmol) in NMP (5 mL) is stirred for 30 min. Then, C-(5-methanesulfonyl-pyridin-2-yl)-methylamine (0.55 g, 2.95 mmol) is added and the reaction mixture is stirred for 18 h at room temperature. The reaction mixture is diluted with a small amount of MeOH. Upon addition of water a precipitate forms which is collected by filtration and dried. Yield: 0.78 g (62% of theory); ESI mass spectrum: $[M+H]^+$=466; Retention time HPLC: 1.09 min (V003_003).

Preparation 8: 5-Bromo-1-(4-cyano-benzyl)-6-methyl-4-oxo-1,4-dihydro-pyridine-3-carboxylic acid 4-methanesulfonyl-benzylamide

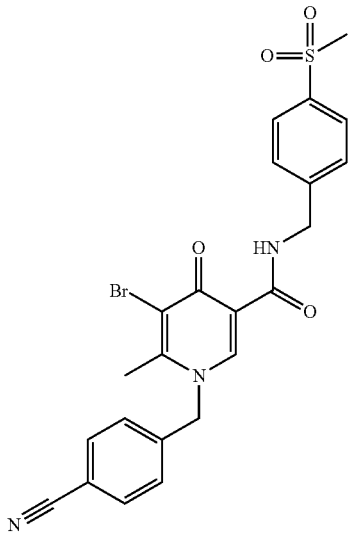

A solution of 5-bromo-1-(4-cyano-benzyl)-6-methyl-4-oxo-1,4-dihydro-pyridine-3-carboxylic acid (preparation 1c, 1.00 g, 2.88 mmol), TBTU (0.925 g, 2.88 mmol), DIPEA (1.50 mL, 8.67 mmol) in DMF (7 mL) is stirred for 30 min. Then, 4-(methylsulfonyl)benzylamine hydrochloride (0.766 g, 3.46 mmol) is added and the reaction mixture is stirred for 18 h at room temperature. The reaction mixture is diluted with MeOH, basified with $NH_4OH$, filtered and purified by preparative reversed-phase HPLC (XBridge, gradient of methanol in water, 0.3% $NH_4OH$, 60° C.). Yield: 0.66 g (29% of theory); ESI mass spectrum: $[M+H]^+$=514 (bromine isotope pattern); Retention time HPLC: 0.88 min (Z003_001).

Preparation 9: 5-Bromo-1-[1-(4-cyano-phenyl)-ethyl]-6-methyl-4-oxo-1,4-dihydro-pyridine-3-carboxylic acid methylamide

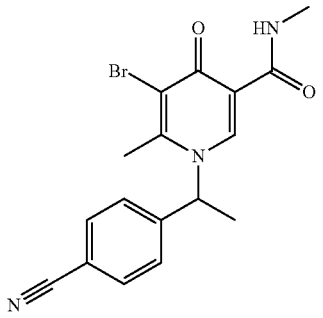

A solution of 5-bromo-1-[1-(4-cyano-phenyl)-ethyl]-6-methyl-4-oxo-1,4-dihydro-pyridine-3-carboxylic acid (preparation 2b, 0.51 g, 1.41 mmol), HBTU (0.620 g, 1.64 mmol), DIPEA (0.50 mL, 2.93 mmol) in DMF (2.7 g) is stirred for 30 min. Then, methylamine (1.6 mL of 2M solution in THF, 3.20 mmol) is added and the reaction mixture is stirred for 18 h at room temperature. The reaction mixture is diluted with MeOH and purified by preparative reversed-phase HPLC (XBridge, gradient of acetonitrile in water, 0.3% $NH_4OH$, 60° C.). Yield: 0.31 g (59% of theory); ESI mass spectrum: $[M+H]^+$=374 (bromine isotope pattern); Retention time HPLC: 0.70 min (Z011_S03).

Preparation 10: 5-Bromo-1-[1-(4-cyano-phenyl)-ethyl]-6-methyl-4-oxo-1,4-dihydro-pyridine-3-carboxylic acid ethylamide

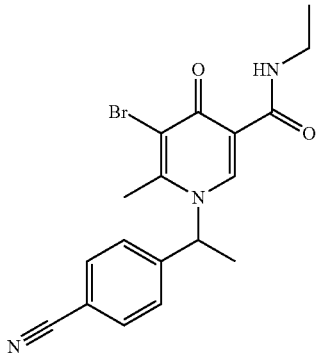

5-Bromo-1-[1-(4-cyano-phenyl)-ethyl]-6-methyl-4-oxo-1,4-dihydro-pyridine-3-carboxylic acid ethylamide is prepared as described for preparation 9, substituting methylamine with ethylamine. ESI mass spectrum: $[M+H]^+$=388 (bromine isotope pattern); Retention time HPLC: 0.92 min (Z018_S04).

Preparation 11: 5-Bromo-1-[1-(4-cyano-phenyl)-ethyl]-6-methyl-4-oxo-1,4-dihydro-pyridine-3-carboxylic acid 4-methanesulfonyl-benzylamide

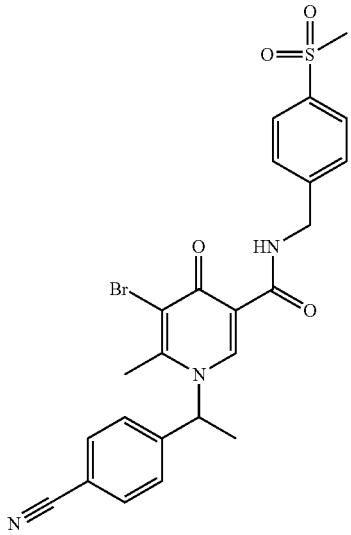

5-Bromo-1-(4-cyano-benzyl)-6-methyl-4-oxo-1,4-dihydro-pyridine-3-carboxylic acid 4-methanesulfonyl-benzylamide can be prepared as described for preparation 9, substituting methylamine with 4-methylsulfonylbenzylamine hydrochloride; ESI mass spectrum: $[M+H]^+$=528 (bromine isotope pattern); Retention time HPLC: 0.95 min (Z018_S04).

Preparation 12: 1-(4-Cyano-benzyl)-4-oxo-5-(3-trifluoromethyl-phenyl)-1,4-dihydro-pyridine-3-carboxylic acid

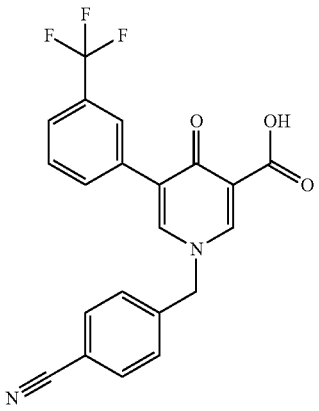

12a 1-(4-Cyano-benzyl)-4-oxo-1,4-dihydro-pyridine-3-carboxylic acid

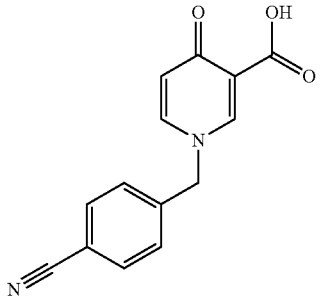

To a solution of 4-hydroxynicotinic acid (2.00 g, 14.4 mmol) in DMF (30 mL) is added sodium hydride (0.62 g, 55% dispersion in mineral oil, 14.2 mmol). After stirring for 10 min at room temperature, 4-cyanobenzyl bromide (2.88 g, 14.7 mmol) is added. After stirring for 2 h at room temperature, DMF (15 mL) is added and the reaction mixture is diluted with water. The formed precipitate is filtered off and dried. Yield: 2.57 g (56% of theory); ESI mass spectrum: $[M+H]^+$=255; Retention time HPLC: 0.68 min (Z002_002).

12b 5-Bromo-1-(4-cyano-benzyl)-4-oxo-1,4-dihydro-pyridine-3-carboxylic acid

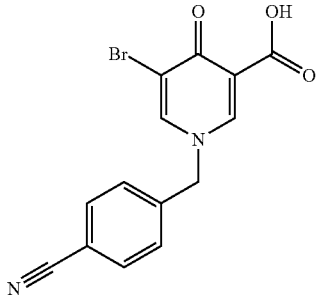

To a solution of 1-(4-cyano-benzyl)-4-oxo-1,4-dihydro-pyridine-3-carboxylic acid (preparation 12a, 2.57 g, 10.1 mmol) in glacial acetic acid (10 ml) is added bromine (2 mL). The reaction mixture is stirred for 6 days at room temperature and additional bromine (1 mL) is added on the first 2 days, respectively. The reaction mixture is evaporated under reduced pressure and co-evaporated with toluene twice. The remaining residue is purified by preparative reversed-phase HPLC (XBridge, gradient of methanol in water, 0.3% $NH_4OH$, 60° C.). Yield: 566 mg (17% of theory); ESI mass spectrum: $[M+H]^+$=333 (bromine isotope pattern); Retention time HPLC: 0.84 min (Z002_002).

12c 1-(4-Cyano-benzyl)-4-oxo-5-(3-trifluoromethyl-phenyl)-1,4-dihydro-pyridine-3-carboxylic acid

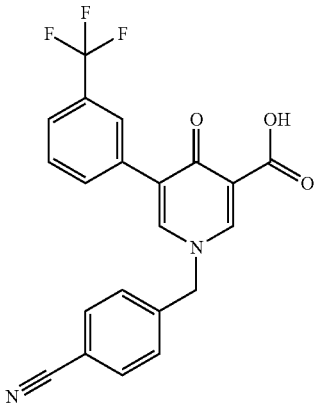

A mixture of 5-bromo-1-(4-cyano-benzyl)-4-oxo-1,4-dihydro-pyridine-3-carboxylic acid (preparation 12b, 0.56 g, 1.68 mmol), 3-(trifluoromethyl)phenylboronic acid (0.39 g, 2.05 mmol), 1,1'-[bis(diphenylphosphino)ferrocene]dichloropalladium(II) (75 mg, 0.10 mmol) and $Cs_2CO_3$ (0.82 g, 2.51 mmol) in dioxane (4 mL) is heated for 24 h at 60° C. The reaction mixture is acidified with acetic acid and purified by preparative reversed-phase HPLC (Sunfire, gradient of methanol in water, 0.1% TFA, 60° C.). Yield: 186 mg (28% of theory); ESI mass spectrum: $[M+H]^+$=399; Retention time HPLC: 1.22 min (Z002_002).

Preparation 13: 2-Methyl-4-oxo-2'-trifluoromethyl-1,4-dihydro-[3,4']bipyridinyl-5-carboxylic acid 4-methanesulfonyl-benzylamide

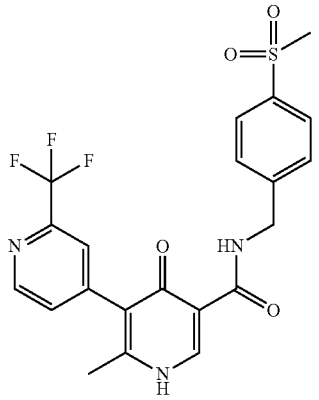

13a 2-Methyl-4-oxo-2'-trifluoromethyl-1,4-dihydro-[3,4']bipyridinyl-5-carboxylic acid

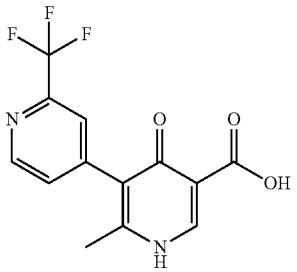

Preparation 13a is prepared as described for preparation 5b, replacing 3-(trifluoromethyl)phenylboronic acid with 2-(trifluoromethyl)pyridine-4-boronic acid. ESI mass spectrum: $[M+H]^+$=299; Retention time HPLC: 0.81 min (Z018_S04).

13b 2-Methyl-4-oxo-2'-trifluoromethyl-1,4-dihydro-[3,4']bipyridinyl-5-carboxylic acid 4-methanesulfonyl-benzylamide

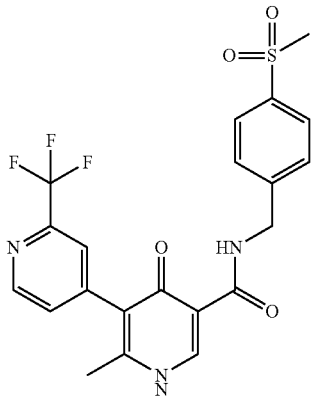

Preparation 13b is prepared as described for preparation 5c, replacing preparation 5b with preparation 13a as starting material and NMP with DMF as solvent. ESI mass spectrum: $[M+H]^+$=466; Retention time HPLC: 0.88 min (Z018_S04).

Example 1.1

1-(4-Cyano-benzyl)-6-methyl-4-oxo-5-(3-trifluoromethyl-phenyl)-1,4-dihydro-pyridine-3-carboxylic acid (2-hydroxy-ethyl)-amide

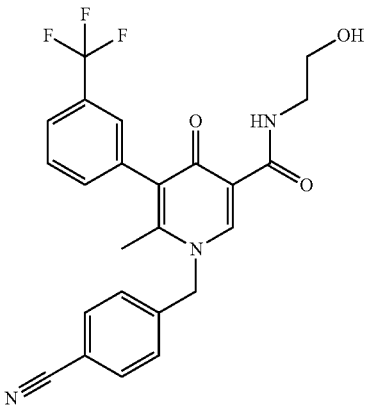

A solution of 1-(4-cyano-benzyl)-6-methyl-4-oxo-5-(3-trifluoromethyl-phenyl)-1,4-dihydro-pyridine-3-carboxylic acid (preparation 1, 70 mg, 0.102 mmol), TBTU (37 mg, 0.115 mmol), DIPEA (40 μL, 0.234 mmol) in DMF (0.5 mL) is stirred for 15 min at room temperature. Ethanolamine (7 μL, 0.116 mmol) is added and the reaction mixture is stirred for 1.5 h at room temperature. The reaction mixture is purified by preparative reversed-phase HPLC (Sunfire, gradient of methanol in water, 0.1% TFA, 60° C.). Yield: 16 mg (34% of theory); ESI mass spectrum: $[M+H]^+$=456; Retention time HPLC: 1.34 min (Z002_005).

The following examples are prepared as described for Example 1.1, employing the appropriate amines instead of ethanolamine, respectively.

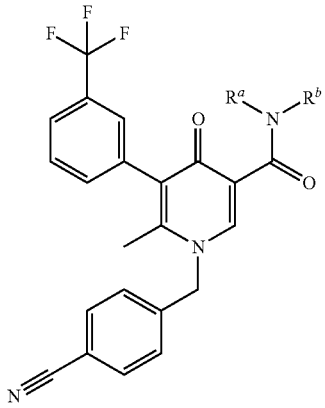

| Example | $R^aR^bN$— | MS $[M+H]^+$ | Retention time HPLC/Method |
|---|---|---|---|
| 1.2 | 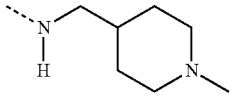 | 523 | 1.19 min Z002_005 |
| 1.3 | 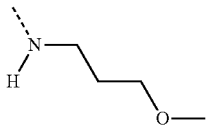 | 484 | 1.45 min Z002_005 |
| 1.4 | 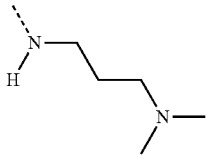 | 497 | 1.17 min Z002_005 |
| 1.5 | 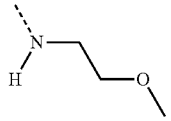 | 470 | 1.42 min Z002_005 |
| 1.6 | 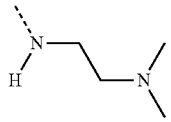 | 483 | 1.16 min Z002_005 |

-continued

| Example | $R^aR^bN$— | MS [M + H]$^+$ | Retention time HPLC/Method |
|---|---|---|---|
| 1.7 | 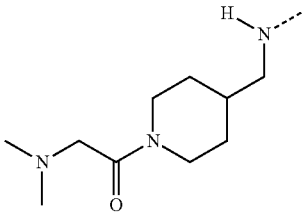 | 594 | 1.21 min Z002_005 |
| 1.8 | 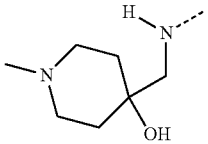 | 539 | 1.19 min Z003_003 |
| 1.9 | 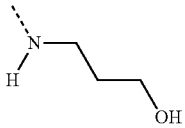 | 470 | 1.16 min Z003_003 |
| 1.10 | 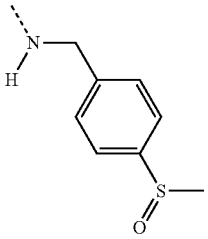 | 564 | 1.02 min Z003_001 |
| 1.11 | 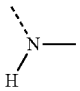 | 426 | 1.18 min Z003_003 |
| 1.12 | 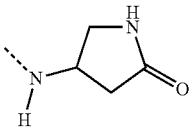 | 495 | 0.79 min Z011_S03 |
| 1.13 | 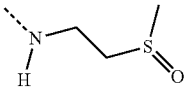 | 502 | 0.80 min Z011_S03 |
| 1.14 | 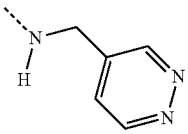 | 504 | 0.82 min Z011_S03 |
| 1.15 | 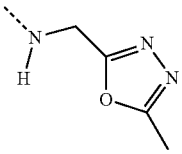 | 508 | 0.84 min Z011_S03 |

-continued

| Example | $R^aR^bN$— | MS [M + H]$^+$ | Retention time HPLC/Method |
|---|---|---|---|
| 1.16 | 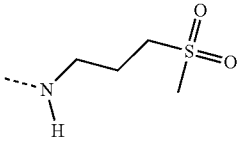 | 532 | 0.83 min Z011_S03 |

Example 1.17

1-(4-Cyano-benzyl)-6-methyl-4-oxo-5-(3-trifluoromethyl-phenyl)-1,4-dihydro-pyridine-3-carboxylic acid (2,3-dihydroxy-propyl)-amide

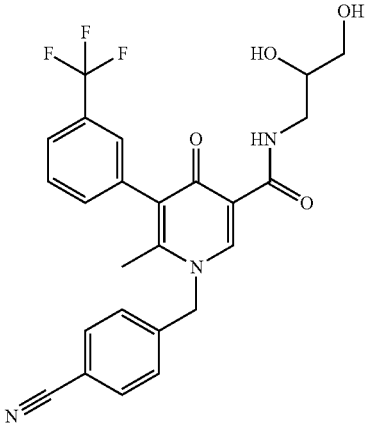

The carboxylic acid (preparation 1, 41 mg, 0.1 mmol) is dissolved in DMF (1 mL) and TBTU (32 mg, 0.1 mmol) and $NEt_3$ (42 μL, 0.3 mmol) are added. The mixture is shaken for 15 min and then added to a solution of 3-amino-1,2-propanediol (11 mg, 0.12 mmol) dissolved in DMF (0.1 mL). The reaction mixture is shaken overnight and purified by preparative reversed phase HPLC (XBridge, gradient of methanol in water+0.3% $NH_4OH$, 60° C.). Yield: 16 mg (30% of theory); ESI mass spectrum: $[M+H]^+$=486; Retention time HPLC: 1.59 min (004_CC_ZQ4).

The following examples are prepared as described for Example 1.17, employing the appropriate amines instead of 3-amino-1,2-propanediol, respectively.

| Example | $R^aR^bN$— | MS [M + H]$^+$ | Retention time HPLC/Method |
|---|---|---|---|
| 1.18 | 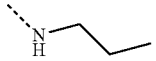 | 454 | 1.5 min 001_CA04 |
| 1.19 | 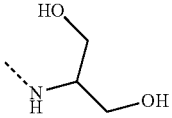 | 486 | 1.2 min 001_CA04 |
| 1.20 | 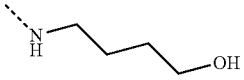 | 484 | 1.7 min 004_CC_ZQ4 |

-continued
| Example | $R^aR^bN$— | MS $[M + H]^+$ | Retention time HPLC/Method |
|---|---|---|---|
| 1.21 | 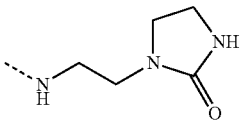 | 524 | 1.6 min 004_CC_ZQ4 |
| 1.22 | 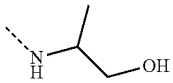 | 470 | 1.3 min 001_CA04 |
| 1.23 | 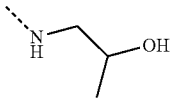 | 470 | 1.3 min 001_CA04 |
| 1.24 | 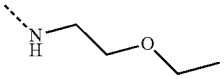 | 484 | 1.4 min 001_CA04 |
| 1.25 | 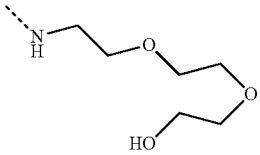 | 544 | 1.3 min 001_CA04 |
| 1.26 | 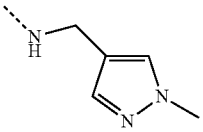 | 506 | 1.4 min 001_CA04 |
| 1.27 | 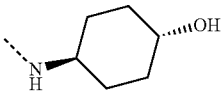 | 510 | 1.4 min 001_CA04 |
| 1.28 | 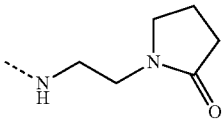 | 523 | 1.3 min 001_CA04 |
| 1.29 | 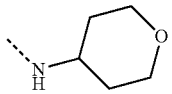 | 496 | 1.3 min 001_CA04 |
| 1.30 | 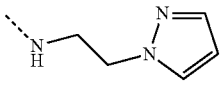 | 506 | 1.7 min 004_CC_ZQ4 |
| 1.31 | 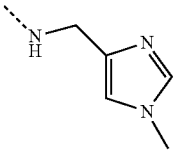 | 506 | 1.3 min 001_CA04 |
| 1.32 | 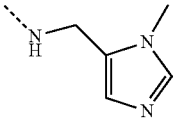 | 506 | 1.3 min 001_CA04 |
| 1.33 | 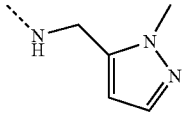 | 506 | 1.4 min 001_CA04 |
| 1.34 | 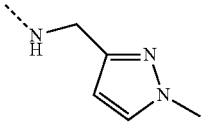 | 506 | 1.4 min 001_CA04 |
| 1.35 | 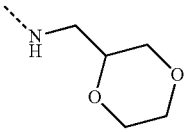 | 512 | 1.4 min 001_CA04 |
| 1.36 | 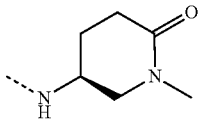 | 523 | 1.3 min 001_CA04 |
| 1.37 | 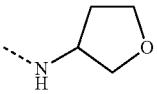 | 482 | 1.4 min 001_CA04 |
| 1.38 | 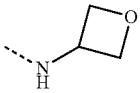 | 468 | 1.3 min 001_CA04 |
| 1.39 | 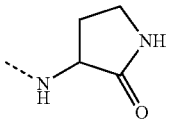 | 495 | 1.3 min 001_CA04 |
| 1.40 | 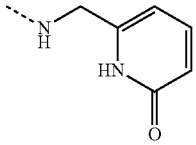 | 519 | 1.3 min 001_CA04 |
| 1.41 | 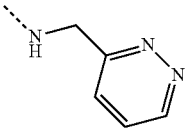 | 504 | 1.3 min 001_CA04 |
| 1.42 | 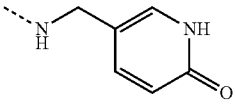 | 519 | 1.3 min 001_CA04 |
| 1.43 | 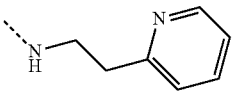 | 517 | 1.4 min 001_CA04 |
| 1.44 | 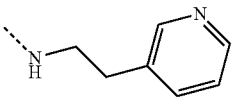 | 517 | 1.4 min 001_CA04 |

-continued
| Example | $R^aR^bN$— | MS $[M + H]^+$ | Retention time HPLC/Method |
|---|---|---|---|
| 1.45 | 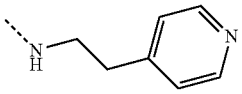 | 517 | 1.4 min 001_CA04 |
| 1.46 | 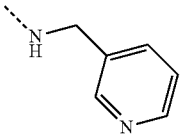 | 503 | 1.4 min 001_CA04 |
| 1.47 | 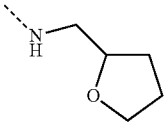 | 496 | 1.4 min 001_CA04 |
| 1.48 | 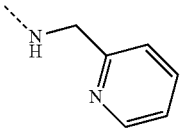 | 503 | 1.4 min 001_CA04 |
| 1.49 | 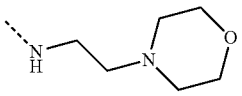 | 525 | 1.4 min 001_CA04 |
| 1.50 | 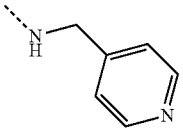 | 503 | 1.4 min 001_CA04 |
| 1.51 | 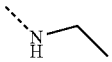 | 440 | 1.4 min 001_CA04 |
| 1.52 | 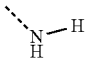 | 412 | 0.82 min Z11_S03 |
| 1.53 | 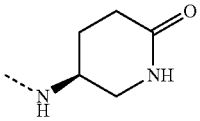 | 509 | 1.0 min 002_CA04 |
| 1.54 | 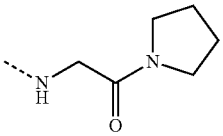 | 523 | 1.1 min 002_CA04 |
| 1.55 | 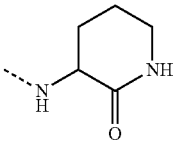 | 509 | 1.0 min 002_CA04 |
| 1.56 | 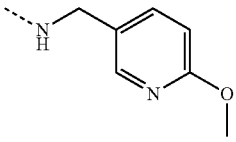 | 533 | 1.2 min 002_CA04 |
-continued
| Example | $R^aR^bN$— | MS $[M + H]^+$ | Retention time HPLC/Method |
|---|---|---|---|
| 1.57 | 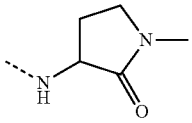 | 509 | 1.0 min 002_CA04 |
| 1.58 | 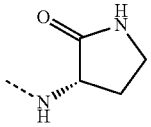 | 495 | 1.0 min 002_CA04 |
| 1.59 | 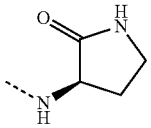 | 495 | 1.0 min 002_CA04 |
| 1.60 | 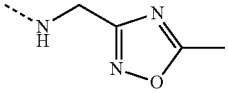 | 508 | 1.1 min 002_CA04 |
| 1.61 | 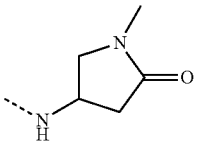 | 509 | 1.0 min 002_CA04 |
| 1.62 | 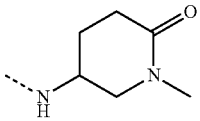 | 523 | 1.0 min 002_CA04 |
| 1.63 | 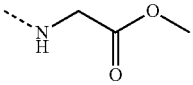 | 484 | 1.1 min 002_CA04 |
| 1.64 | 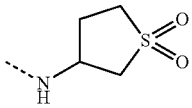 | 530 | 1.1 min 002_CA04 |
| 1.65 | 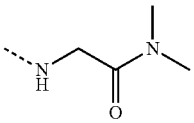 | 497 | 1.0 min 002_CA04 |
| 1.66 | 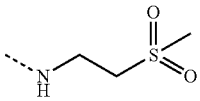 | 518 | 1.0 min 002_CA04 |
| 1.67 | 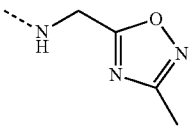 | 508 | 0.9 min Z011_S03 |

Example 2.1

1-Benzyl-6-methyl-4-oxo-5-(3-trifluoromethyl-phenyl)-1,4-dihydro-pyridine-3-carboxylic acid 4-methanesulfonyl-benzylamide

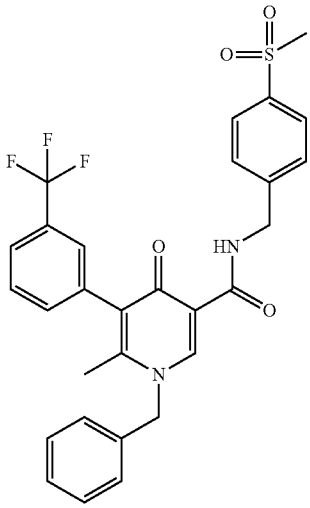

A mixture of 6-methyl-4-oxo-5-(3-trifluoromethyl-phenyl)-1,4-dihydro-pyridine-3-carboxylic acid 4-methane-sulfonyl-benzylamide (preparation 5, 50 mg, 0.108 mmol), $K_2CO_3$ (27 mg, 0.193 mmol) and benzyl bromide (0.015 mL, 0.129 mmol) in DMF (0.5 mL) is stirred for 30 min at 80° C. (microwave). The reaction mixture is diluted with MeOH, filtered and purified by preparative reversed-phase HPLC (XBridge, gradient of methanol in water, 0.3% $NH_4OH$, 60° C.). Yield: 28 mg (47% of theory); ESI mass spectrum: $[M+H]^+$=555; Retention time HPLC: 1.16 min (Z003_001).

The following examples are prepared as described for Example 2.1, employing the appropriate aryl- or heteroaryl-methyl bromides instead of benzyl bromide, respectively.

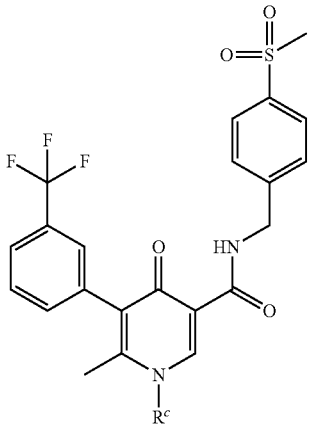

| Example | $R^c$ | MS $[M + H]^+$ | Retention time HPLC/Method |
|---|---|---|---|
| 2.2 | 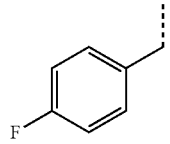 | 573 | 1.17 min Z003_001 |
| 2.3 | 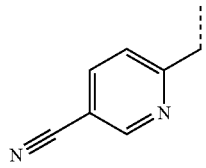 | 581 | 1.03 min Z003_001 |
| 2.4 | 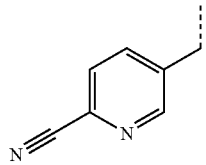 | 581 | 1.04 min Z003_001 |
| 2.5 | 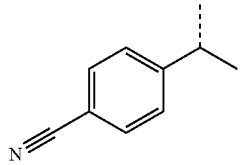 | 594 | 1.09 min Z003_001 |
| 2.6 | 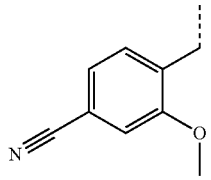 | 610 | 1.12 min Z003_001 |
| 2.7 | 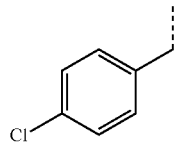 | 589 | 1.23 min Z003_001 |
| 2.8 | 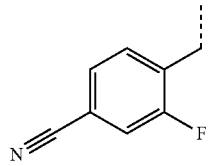 | 598 | 1.11 min Z003_001 |
| 2.9 | 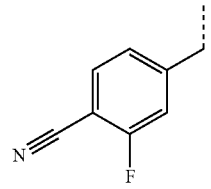 | 598 | 1.12 min Z003_001 |
| 2.10 | 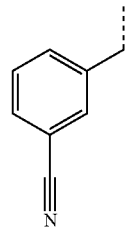 | 580 | 1.10 min Z003_001 |
| 2.11 | 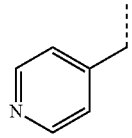 | 556 | 1.01 min Z003_001 |

-continued

| Example | $R^c$ | MS $[M + H]^+$ | Retention time HPLC/Method |
|---|---|---|---|
| 2.12 | 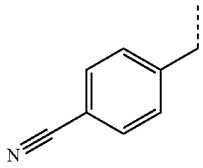 | 580 | 1.03 min Z003_001 |

Example 2.5A and Example 2.5B

Enantiomers of Example 2.5

90 mg of racemic example 2.5 are separated by chiral HPLC (Daicel IB, 250 mm×20 mm, 20% MeOH+0.2% diethylamine in supercritical $CO_2$, 40° C.).

Early eluting enantiomer (Example 2.5A): Retention time chiral HPLC=4.086 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=594. Yield: 37 mg Late eluting enantiomer (Example 2.5B): Retention time chiral HPLC=5.952 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=594. Yield: 34 mg The following examples are prepared as described for Example 2.1, substituting preparation 5 with preparation 6 and employing the appropriate aryl- or heteroaryl-methyl bromides instead of benzyl bromide, respectively.

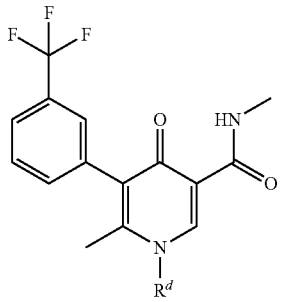

| Example | $R^d$ | MS $[M + H]^+$ | Retention time HPLC/Method |
|---|---|---|---|
| 3.1 | 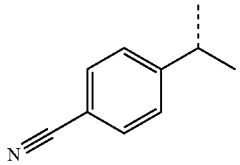 | 440 | 1.09 min Z003_001_A05 |
| 3.2 | 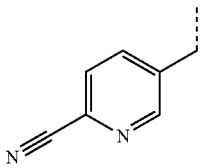 | 427 | 1.02 min Z003_001_A05 |

-continued

| Example | $R^d$ | MS $[M + H]^+$ | Retention time HPLC/Method |
|---|---|---|---|
| 3.3 | 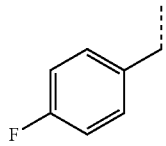 | 419 | 1.18 min Z003_001_A05 |
| 3.4 | 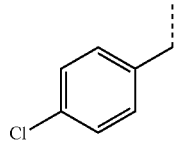 | 435 | 1.23 min Z003_001_A05 |
| 3.5 | 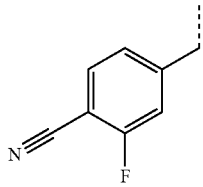 | 444 | 1.13 min Z003_001_A05 |
| 3.6 | 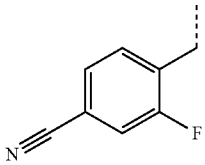 | 444 | 1.08 min Z003_001_A05 |
| 3.7 | 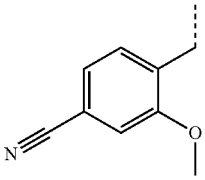 | 456 | 1.11 min Z003_001_A05 |
| 3.8 | 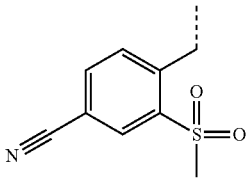 | 557 | 0.93 min Z011_S03 |
| 3.9 | 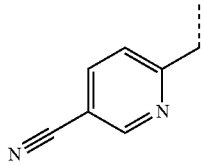 | 427 | 1.04 min Z003_001_A05 |

Example 3.1A and Example 3.1B

Enantiomers of Example 3.1

100 mg of racemic example 3.1 are separated by chiral HPLC (Daicel IB, 250 mm×20 mm, 20% MeOH+0.2% diethylamine in supercritical $CO_2$, 40° C.).

Early eluting enantiomer (Example 3.1A): Retention time chiral HPLC=1.759 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=440. Yield: 43 mg Late eluting enantiomer (Example 3.1B): Retention time chiral HPLC=2.459 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=440. Yield: 36 mg The following examples are prepared as described for Example 2.1, substituting preparation 5 with preparation 7 and employing the appropriate aryl- or heteroaryl-methyl bromides instead of benzyl bromide, respectively.

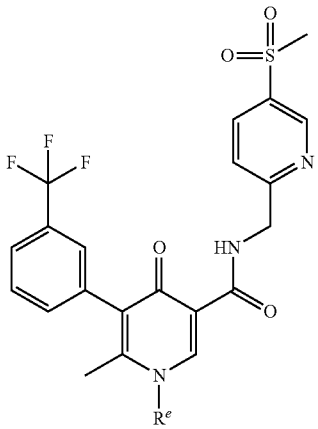

| Example | $R^e$ | MS $[M + H]^+$ | Retention time HPLC/Method |
|---|---|---|---|
| 4.1 | 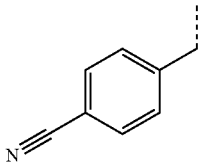 | 581 | 1.06 min Z003_001 |
| 4.2 | 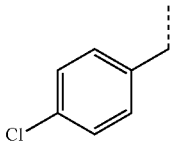 | 590 | 1.46 min V003_003 |
| 4.3 | 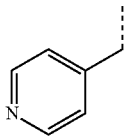 | 557 | 1.23 min V003_003 |
| 4.4 | 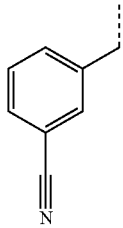 | 581 | 1.32 min V003_003 |

-continued

| Example | $R^e$ | MS $[M + H]^+$ | Retention time HPLC/Method |
|---|---|---|---|
| 4.5 | 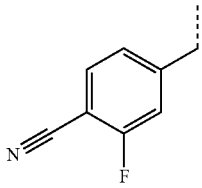 | 599 | 1.34 min V003_003 |
| 4.6 | 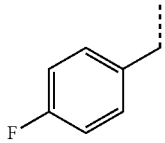 | 573 | 1.17 min Z003_001 |
| 4.7 | 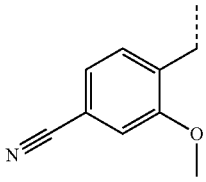 | 611 | 1.09 min Z003_001 |
| 4.8 | 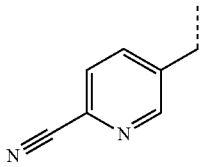 | 582 | 1.01 min Z003_001 |
| 4.9 | 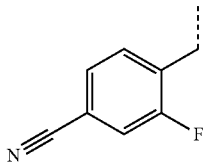 | 599 | 1.09 min Z003_001 |
| 4.10 | 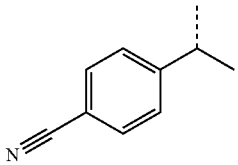 | 595 | 1.07 min Z003_001 |

The following examples are prepared as described for Example 2.1, substituting preparation 5 with preparation 13 and employing the appropriate aryl- or heteroaryl-methyl bromides instead of benzyl bromide, respectively.

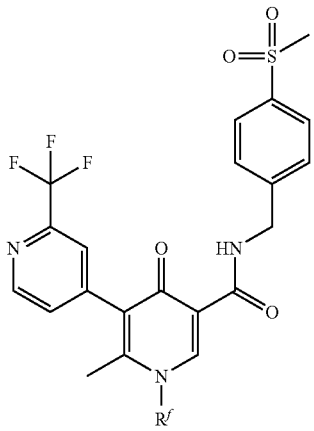

| Example | $R^f$ | MS [M + H]$^+$ | Retention time HPLC/Method |
|---|---|---|---|
| 5.1 | 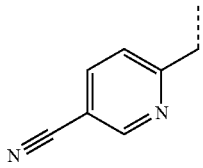 | 582 | 0.95 min Z018_S04 |
| 5.2 | 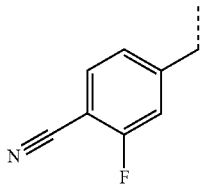 | 599 | 1.01 min Z018_S04 |
| 5.3 | 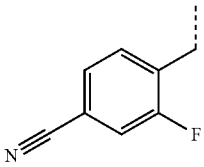 | 599 | 0.99 min Z018_S04 |

Example 6.1

1-(4-Cyano-benzyl)-6-methyl-4-oxo-5-phenyl-1,4-dihydro-pyridine-3-carboxylic acid 4-methanesulfonyl-benzylamide

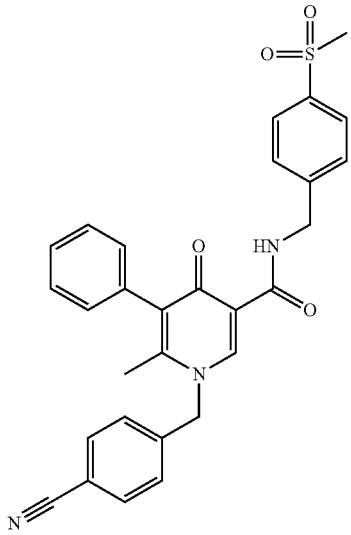

To a solution of 5-bromo-1-(4-cyano-benzyl)-6-methyl-4-oxo-1,4-dihydro-pyridine-3-carboxylic acid 4-methanesulfonyl-benzylamide (preparation 8, 80 mg, 0.156 mmol), phenylboronic acid (27 mg, 0.22 mmol), 1,1'-[bis(diphenylphosphino)ferrocene]dichloropalladium(II) (11 mg, 0.016 mmol) in acetonitrile (2 mL) is added 2 M aqueous $K_2CO_3$ solution (0.16 mL, 0.32 mmol). After stirring for 72 h at 75° C., the reaction mixture is filtered, basified with aqueous $NH_4OH$ solution and purified by preparative reversed-phase HPLC (XBridge, gradient of methanol in water, 0.3% $NH_4OH$, 60° C.). Yield: 59 mg (74% of theory); ESI mass spectrum: $[M+H]^+$=512; Retention time HPLC: 0.98 min (Z003_001).

The following examples are prepared as described for Example 6.1, employing the appropriate aryl- or heteroaryl-boronic acids instead of phenylboronic acid.

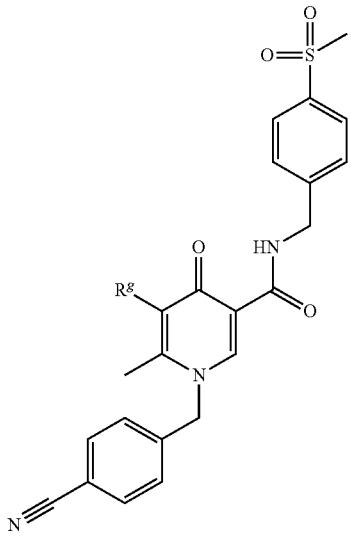

| Example | $R^g$ | MS $[M + H]^+$ | Retention time HPLC/Method |
|---|---|---|---|
| 6.2 | 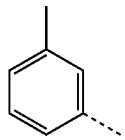 | 526 | 1.05 min Z003_001 |
| 6.3 | 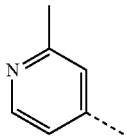 | 527 | 0.85 min Z003_001 |
| 6.4 | 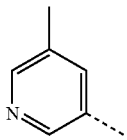 | 527 | 0.82 min Z003_001 |
| 6.5 | 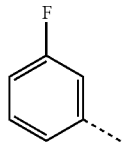 | 530 | 0.99 min Z003_001 |
| 6.6 | 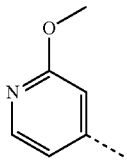 | 543 | 0.91 min Z003_001 |
| 6.7 | 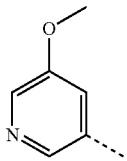 | 543 | 0.86 min Z003_001 |
| 6.8 | 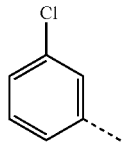 | 546 | 1.06 min Z003_001 |
| 6.9 | 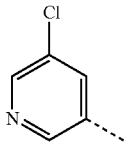 | 547 | 0.95 min Z003_001 |
| 6.10 | 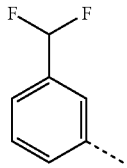 | 562 | 0.93 min Z003_001 |

-continued

| Example | $R^g$ | MS $[M + H]^+$ | Retention time HPLC/Method |
|---|---|---|---|
| 6.11 | 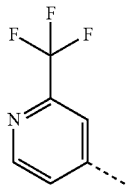 | 581 | 0.97 min Z003_001 |
| 6.12 | 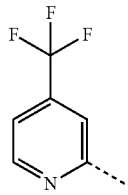 | 581 | 0.94 min Z003_001 |
| 6.13 | 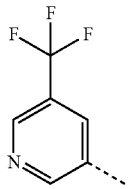 | 581 | 0.99 min Z003_001 |

The following examples are prepared as described for Example 1.17, replacing preparation 1 with preparation 2 as starting material and employing the appropriate amines, respectively.

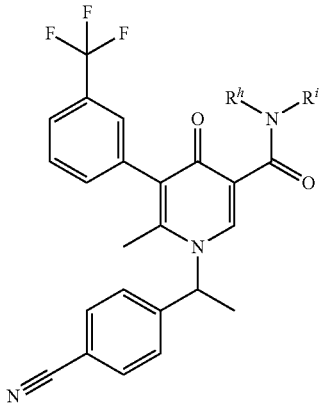

| Example | $R^hR^iN$— | MS $[M + H]^+$ | Retention time HPLC/Method |
|---|---|---|---|
| 7.1 | 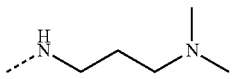 | 511 | 0.5 min 015_CC_SQD1 |
| 7.2 | 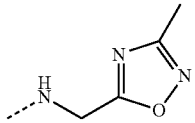 | 522 | 0.5 min 015_CC_SQD1 |

-continued

| Example | $R^hR^iN$— | MS [M + H]$^+$ | Retention time HPLC/Method |
|---|---|---|---|
| 7.3 | 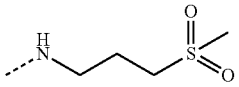 | 546 | 0.4 min 015_CC_SQD1 |
| 7.4 | 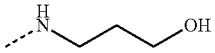 | 484 | 0.4 min 015_CC_SQD1 |
| 7.5 | 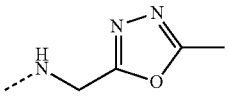 | 522 | 0.4 min 015_CC_SQD1 |
| 7.6 | 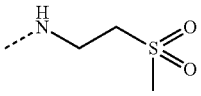 | 532 | 0.4 min 015_CC_SQD1 |
| 7.7 | 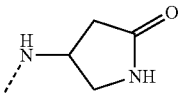 | 509 | 0.4 min 015_CC_SQD1 |
| 7.8 | 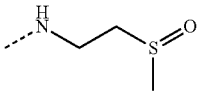 | 516 | 0.4 min 015_CC_SQD1 |
| 7.9 | 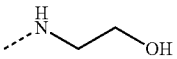 | 470 | 0.4 min 015_CC_SQD1 |
| 7.10 | 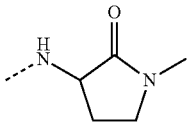 | 523 | 0.4 min 015_CC_SQD1 |
| 7.11 | 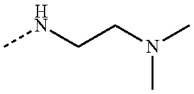 | 417 | 0.5 min 015_CC_SQD1 |
| 7.12 | 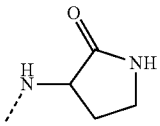 | 509 | 0.4 min 015_CC_SQD1 |

Examples 7.13-7.20 are prepared as described for Example 1.17, replacing preparation 1 with preparation 2 as starting material and employing the appropriate amines, respectively.

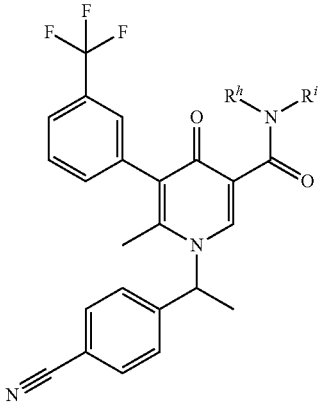

| | Example | $R^hR^iN$— | MS [M + H]$^+$ | Retention time HPLC/Method |
|---|---|---|---|---|
| BI01290664 | 7.13 | 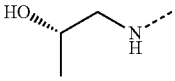 | 484 | 0.78 min 005_CA01 |
| BI01289587 | 7.14 | 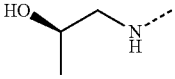 | 484 | 0.77 min 002_CA03 |
| BI01289640 | 7.15 | 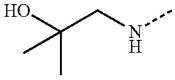 | 498 | 0.81 min 005_CA01 |
| BI01289946 | 7.16 | 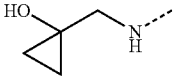 | 496 | 0.73 min 004_CA05 |
| BI01252544 | 7.17 | 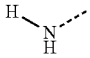 | 426 | 1.03 min 002_CA04 |
| BI01229575 | 7.18 | 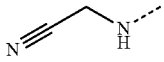 | 465 | 1.04 min Z018_S04 |
| BI01278675 | 7.19 | 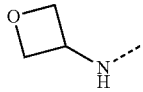 | 482 | 0.87 min Z018_S04 |
| BI01299522 | 7.20 | 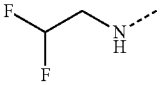 | 490 | 0.93 min Z018_S04 |

Example 8

1-[1-(4-Cyano-phenyl)-ethyl]-5-(3-difluoromethyl-phenyl)-6-methyl-4-oxo-1,4-dihydro-pyridine-3-carboxylic acid methylamide

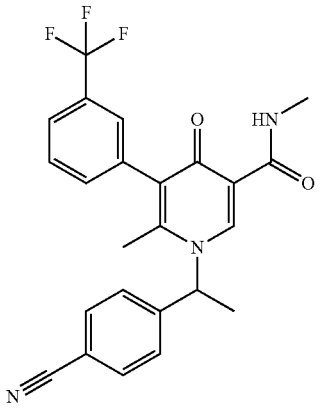

To a solution of 5-bromo-1-[1-(4-cyano-phenyl)-ethyl]-6-methyl-4-oxo-1,4-dihydro-pyridine-3-carboxylic acid methylamide (preparation 9, 100 mg, 0.267 mmol), 3-difluoromethyl-phenylboronic acid (67 mg, 0.390 mmol), palladium (0) tetrakis(triphenylphosphine) (25 mg, 0.022 mmol) in acetonitrile (2 mL) is added 2 M aqueous $K_2CO_3$ solution (0.30 mL, 0.60 mmol). After stirring for 18 h at 75° C., the reaction mixture is purified by preparative reversed-phase HPLC (XBridge, gradient of methanol in water, 0.1% $NH_4OH$, 60° C.). Yield: 80 mg (71% of theory); ESI mass spectrum: $[M+H]^+$=422; Retention time HPLC: 0.99 min (Z018_S04).

Example 8A and Example 8B

Enantiomers of Example 8

80 mg of racemic example 8 are separated by chiral HPLC (Daicel IB, 250 mm×20 mm, 20% MeOH+0.2% diethylamine in supercritical $CO_2$, 40° C.).

Early eluting enantiomer (Example 8A): Retention time chiral HPLC=2.143 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=422. Yield: 27 mg Late eluting enantiomer (Example 8B): Retention time chiral HPLC=3.136 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=422. Yield: 31 mg The following examples are prepared as described for Example 1.17, replacing preparation 1 with preparation 3 as starting material and employing the appropriate amines, respectively.

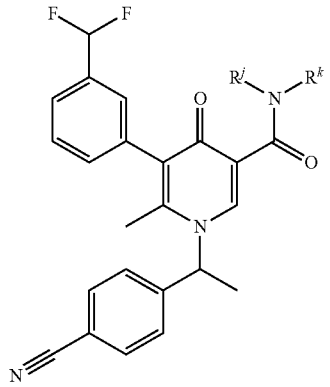

| Example | $R^jR^kN$— | MS $[M + H]^+$ | Retention time HPLC/Method |
|---|---|---|---|
| 8.1 | 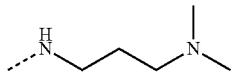 | 493 | 0.5 min 015_CC_SQD1 |
| 8.2 | 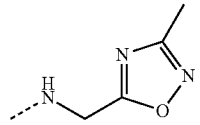 | 504 | 0.4 min 015_CC_SQD1 |
| 8.3 | 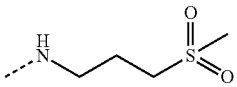 | 528 | 0.4 min 015_CC_SQD1 |
| 8.4 | 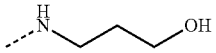 | 466 | 0.4 min 015_CC_SQD1 |
| 8.5 | 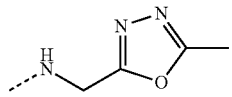 | 504 | 0.4 min 015_CC_SQD1 |
| 8.6 | 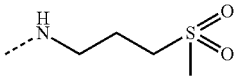 | 514 | 0.4 min 015_CC_SQD1 |
| 8.7 | 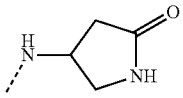 | 491 | 0.4 min 015_CC_SQD1 |
| 8.8 | 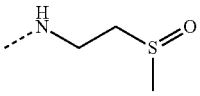 | 498 | 0.4 min 015_CC_SQD1 |
| 8.9 | 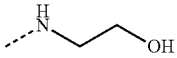 | 452 | 0.4 min 015_CC_SQD1 |
| 8.10 | 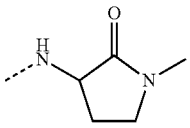 | 505 | 0.4 min 015_CC_SQD1 |
| 8.11 | 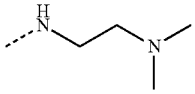 | 479 | 0.4 min 015_CC_SQD1 |

-continued

| Example | $R^jR^kN$— | MS $[M + H]^+$ | Retention time HPLC/Method |
|---|---|---|---|
| 8.12 | 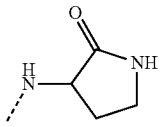 | 491 | 0.4 min 015_CC_ SQD1 |
| 8.13 | 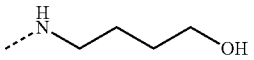 | 480 | 0.7 min 004_CA05 |
| 8.14 | 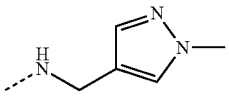 | 502 | 0.7 min 004_CA05 |
| 8.15 | 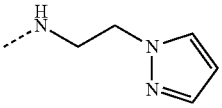 | 502 | 0.7 min 004_CA05 |
| 8.16 | 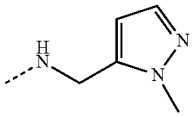 | 502 | 0.7 min 004_CA05 |
| 8.17 | 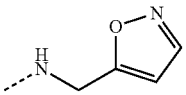 | 489 | 0.7 min 004_CA05 |
| 8.18 | 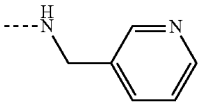 | 499 | 0.7 min 004_CA05 |
| 8.19 | 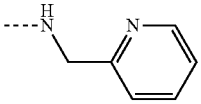 | 499 | 0.7 min 004_CA05 |
| 8.20 | 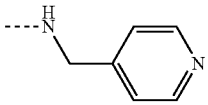 | 499 | 0.7 min 004_CA05 |
| 8.21 | 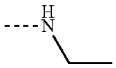 | 436 | 0.7 min 004_CA05 |
| 8.22 | 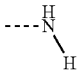 | 408 | 0.6 min 004_CA05 |
| 8.23 | 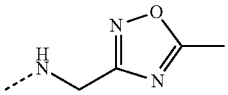 | 504 | 0.84 min Z011_S03 |

Examples 8.24-8.28 are prepared as described for Example 1.17, replacing preparation 1 with preparation 3 as starting material and employing the appropriate amines, respectively.

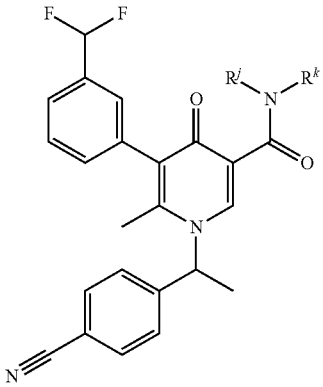

| | Example | $R^jR^kN$— | MS $[M + H]^+$ | Retention time HPLC/Method |
|---|---|---|---|---|
| B101213073 | 8.24 | 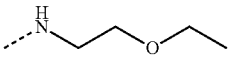 | 480 | 1.05 min Z018_S04 |
| B101213074 | 8.25 | 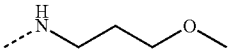 | 480 | 1.02 min Z018_S04 |
| B101213072 | 8.26 | 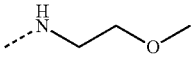 | 466 | 1.00 min Z018_S04 |
| B101237203 | 8.27 | 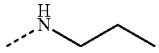 | 450 | 0.89 min Z011_S03 |
| B101237199 | 8.28 | 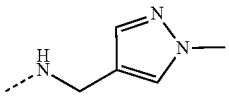 | 502 | 0.83 min Z011_S03 |

Example 9

1-[1-(4-Cyano-phenyl)-ethyl]-2-methyl-4-oxo-2'-trifluoromethyl-1,4-dihydro-[3,4']bipyridinyl-5-carboxylic acid methylamide

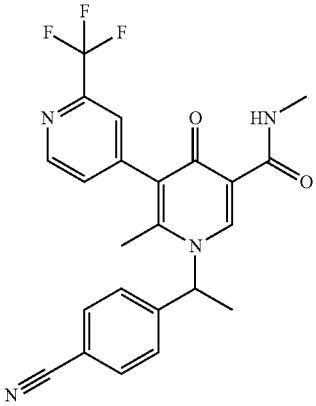

To a solution of 5-bromo-1-[1-(4-cyano-phenyl)-ethyl]-6-methyl-4-oxo-1,4-dihydro-pyridine-3-carboxylic acid methylamide (preparation 9, 240 mg, 0.641 mmol), 2-(trifluoromethyl)pyridine-4-boronic acid (148 mg, 0.78 mmol), palladium (0) tetrakis(triphenylphosphine) (79 mg, 0.068 mmol) in acetonitrile (4 mL) is added 2 M aqueous $K_2CO_3$ solution (0.60 mL, 1.20 mmol). After stirring for 72 h at 75° C., the reaction mixture is diluted with methanol and purified by preparative reversed-phase HPLC (XBridge, gradient of methanol in water, 0.1% $NH_4OH$, 60° C.). Yield: 48 mg (17% of theory); ESI mass spectrum: $[M+H]^+$=441; Retention time HPLC: 0.78 min (Z011_S03).

Example 9A and Example 9B

Enantiomers of Example 9

48 mg of racemic example 9 are separated by chiral HPLC (Daicel IB, 250 mm×20 mm, 20% MeOH+0.2% diethylamine in supercritical $CO_2$ 40° C.).

Early eluting enantiomer (Example 9A): Retention time chiral HPLC=1.832 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=441. Yield: 23 mg Late eluting enantiomer (Example 9B): Retention time chiral HPLC=2.710 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=441. Yield: 24 mg The following examples are prepared as described for Example 1.17, replacing preparation 1 with preparation 4 as starting material and employing the appropriate amines, respectively.

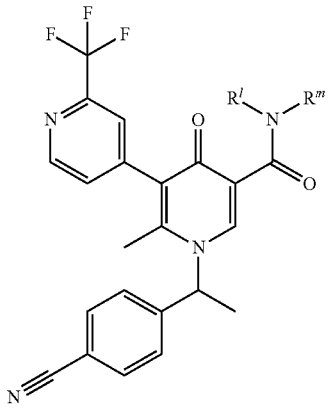

| Example | $R^lR^mN$— | MS $[M+H]^+$ | Retention time HPLC/Method |
|---|---|---|---|
| 9.1 | 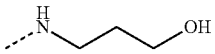 | 485 | 0.6 min 004_CA55 |
| 9.2 | 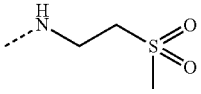 | 533 | 0.6 min 004_CA55 |
| 9.3 | 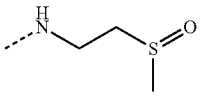 | 517 | 0.6 min 004_CA55 |

-continued

| Example | $R^lR^mN$— | MS $[M+H]^+$ | Retention time HPLC/Method |
|---|---|---|---|
| 9.4 | 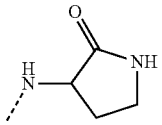 | 510 | 0.6 min 004_CA55 |
| 9.5 | 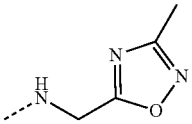 | 523 | 0.7 min 004_CA05 |
| 9.6 | 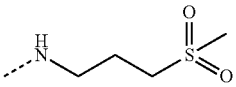 | 547 | 0.6 min 004_CA05 |
| 9.7 | 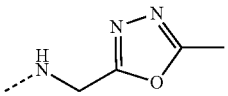 | 523 | 0.6 min 004_CA05 |
| 9.8 | 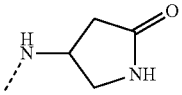 | 510 | 0.6 min 004_CA05 |
| 9.9 | 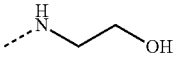 | 471 | 0.6 min 004_CA05 |
| 9.10 | 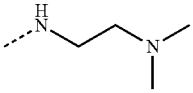 | 498 | 0.7 min 004_CA05 |
| 9.11 | 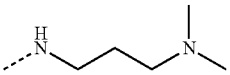 | 512 | 0.7 min 004_CA05 |
| 9.12 | 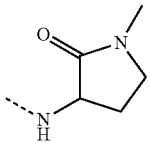 | 524 | 0.8 min Z011_S03 |

Example 9.5A and Example 9.5B

Enantiomers of Example 9.5

155 mg of racemic example 9.5 are separated by chiral HPLC (Daicel IB, 250 mm×20 mm, 20% MeOH+0.2% diethylamine in supercritical $CO_2$, 40° C.).

Early eluting enantiomer (Example 9.5A): Retention time chiral HPLC=2.106 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=523. Yield: 61 mg Late eluting enantiomer (Example 9.5B): Retention time chiral HPLC=3.017 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=523. Yield: 57 mg Examples 9.13-9.55 are prepared according to one of the following procedures (Procedure A or Procedure B) employing the appropriate amines.

Procedure A

The carboxylic acid (preparation 4, 43 mg, 100 μmol) is dissolved in acetonitrile (1 mL) and N-methylmorpholine (55 μL, 0.500 mmol) is added. The mixture is cooled to 0° C., then the amine (250 μmol) and 1-propanephosphonic acid cyclic anhydride (50% in ethyl acetate, 200 μL, 343 μmol) are added. The reaction mixture is shaken overnight and purified by preparative reversed phase HPLC (XBridge, gradient of acetonitrile in water).

Procedure B

The carboxylic acid (preparation 4, 40 mg, 94 μmol) is dissolved in DMF (1 mL) and $NEt_3$ (41 μL, 0.29 mmol) is added. The mixture is shaken for 15 min and then HATU (36 mg, 94 μmol) is added. The mixture is shaken for 15 min and then the amine (187 μmol) is added. The reaction mixture is shaken overnight and purified by preparative reversed phase HPLC (XBridge, gradient of acetonitrile in water).

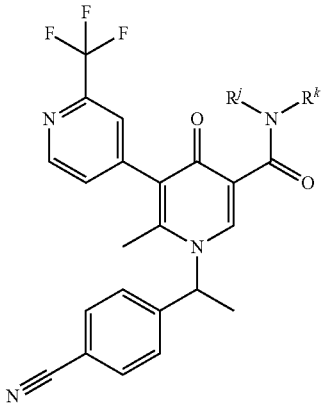

| Example | $R^jR^kN$— | MS $[M + H]^+$ | Retention time HPLC/ Method | Procedure |
|---|---|---|---|---|
| 9.13 | 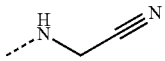 | 466 | 0.92 min Z011_S03 | A |
| 9.14 | 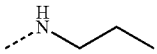 | 469 | 0.98 min Z011_S03 | A |
| 9.15 | 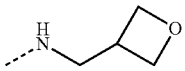 | 497 | 0.90 min Z011_S03 | A |
| 9.16 | 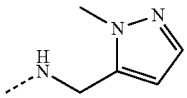 | 521 | 0.92 min Z011_S03 | B |
| 9.17 | 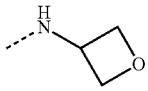 | 483 | 0.91 min Z011_S03 | A |
| 9.18 | 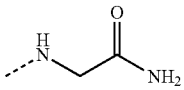 | 484 | 0.84 min Z011_S03 | A |
| 9.19 | 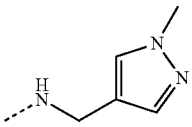 | 521 | 0.91 min Z011_S03 | A |

-continued

| Example | $R^jR^kN$— | MS $[M + H]^+$ | Retention time HPLC/ Method | Procedure |
|---|---|---|---|---|
| 9.20 | 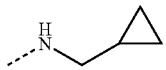 | 481 | 0.99 min Z011_S03 | A |
| 9.21 | 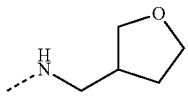 | 511 | 0.93 min Z011_S03 | A |
| 9.22 | 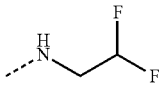 | 491 | 0.96 min Z011_S03 | A |
| 9.23 | 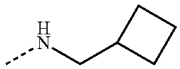 | 495 | 1.04 min Z011_S03 | A |
| 9.24 | 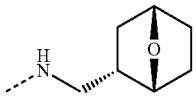 | 537 | 0.97 min Z011_S03 | A |
| 9.25 | 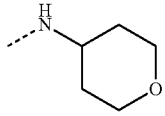 | 511 | 0.93 min Z011_S03 | A |
| 9.26 | 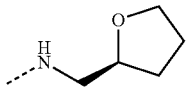 | 511 | 0.95 min Z011_S03 | A |
| 9.27 | 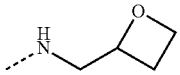 | 497 | 0.91 min Z011_S03 | A |
| 9.28 | 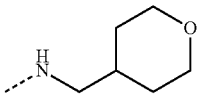 | 525 | 0.95 min Z011_S03 | A |
| 9.29 | 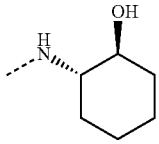 | 525 | 0.96 min Z011_S03 | B |
| 9.30 | 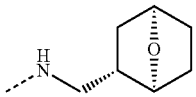 | 537 | 0.95 min Z011_S03 | A |
| 9.31 | 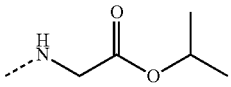 | 527 | 1.00 min Z011_S03 | A |
| 9.32 | 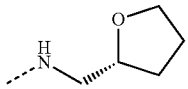 | 511 | 0.95 min Z011_S03 | A |
| 9.33 | 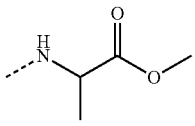 | 513 | 1.01 min Z18_S04 | A |

-continued

| Example | $R^jR^kN$— | MS $[M + H]^+$ | Retention time HPLC/ Method | Procedure |
|---|---|---|---|---|
| 9.34 | 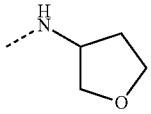 | 497 | 0.92 min Z011_S03 | A |
| 9.35 | 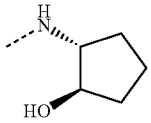 | 511 | 0.94 min Z011_S03 | B |
| 9.36 | 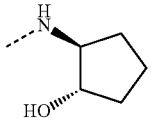 | 511 | 0.93 min Z011_S03 | B |
| 9.37 | 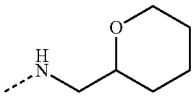 | 525 | 0.99 min Z011_S03 | A |
| 9.38 | 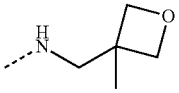 | 511 | 0.93 min Z011_S03 | A |
| 9.39 | 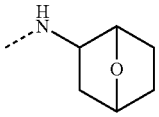 | 523 | 0.95 min Z011_S03 | A |
| 9.40 | 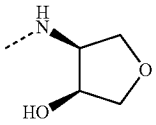 | 513 | 0.86 min Z011_S03 | B |
| 9.41 | 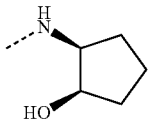 | 511 | 0.92 min Z011_S03 | B |
| 9.42 | 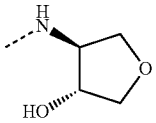 | 513 | 0.87 min Z011_S03 | B |
| 9.43 | 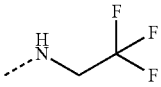 | 509 | 1.01 min Z011_S03 | A |
| 9.44 | 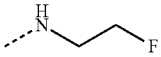 | 473 | 0.93 min Z011_S03 | A |
| 9.45 | 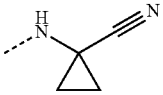 | 492 | 0.95 min Z011_S03 | A |
| 9.46 | 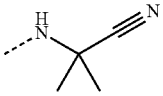 | 494 | 0.98 min Z011_S03 | A |

-continued

| Example | $R^jR^kN$— | MS $[M + H]^+$ | Retention time HPLC/ Method | Procedure |
|---|---|---|---|---|
| 9.47 | 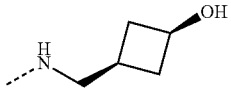 | 511 | 0.89 min Z011_S03 | A |
| 9.48 | 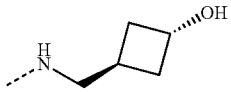 | 511 | 0.89 min Z011_S03 | A |
| 9.49 | 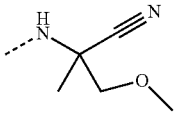 | 524 | 0.98 min Z011_S03 | A |
| 9.50 | 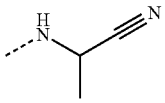 | 480 | 0.96 min Z011_S03 | A |
| 9.51 | 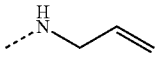 | 467 | 0.97 min Z011_S03 | A |
| 9.52 | 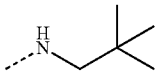 | 497 | 1.05 min Z011_S03 | A |
| 9.53 | 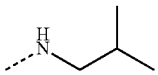 | 483 | 1.02 min Z011_S03 | A |
| 9.54 | 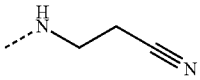 | 480 | 0.91 min Z011_S03 | A |
| 9.55 | 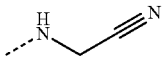 | 465 | 0.95 min Z011_S03 | A |

Examples 9.56-9.59 are prepared in two steps: (1) Amide coupling as described for Example 1.17, replacing preparation 1 with preparation 2b and employing the appropriate amines, respectively; (2) Suzuki coupling as described for preparation 5b, substituting 3-s (trifluoromethyl)phenylboronic acid with 2-(trifluoromethyl)pyridine-4-boronic acid and substituting preparation 5a with the appropriate intermediates from step 1, respectively.

Intermediates from Step 1 (Amide Coupling)

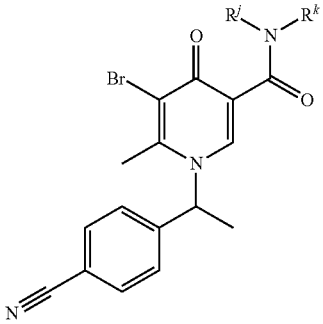

| Intermediate for Example . . . | $R^jR^kN$— | MS [M + H]$^+$ | Retention time HPLC/ Method |
|---|---|---|---|
| 9.56 | 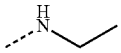 | 388 (Br pattern) | 0.75 min Z011_S03 |
| 9.57 | 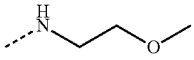 | 418 (Br pattern) | 0.73 min Z011_S03 |
| 9.58 | 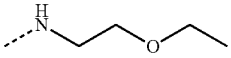 | 432 (Br pattern) | 0.78 min Z011_S03 |
| 9.59 | 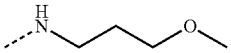 | 432 (Br pattern) | 0.74 min Z011_S03 |

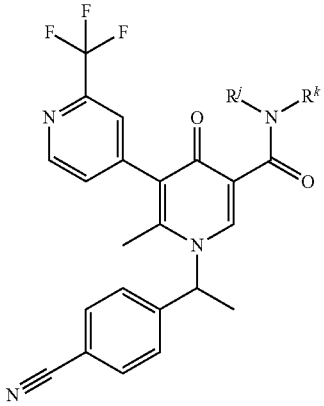

| Example | $R^jR^kN$— | MS [M + H]$^+$ | Retention time HPLC/Method |
|---|---|---|---|
| 9.56 | 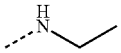 | 455 | 1.00 min Z018_S04 |
| 9.57 | 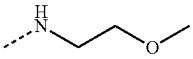 | 485 | 0.81 min Z011_S03 |
| 9.58 | 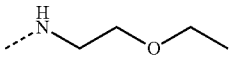 | 499 | 1.02 min Z018_S04 |
| 9.59 | 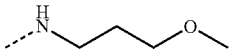 | 499 | 0.83 min Z011_S03 |

Example 9.56A and Example 9.56B

Enantiomers of Example 9.56

35 mg of racemic example 9.56 are separated by chiral HPLC (Daicel IB, 250 mm×20 mm, 15% MeOH+0.2% diethylamine in supercritical $CO_2$, 40° C.).

Early eluting enantiomer (Example 9.56A): Retention time chiral HPLC=2.426 min (Daicel Chiralpak®IB, 4.6 mm×250 mm 5 μm, 4 ml/min, 10 min, 15% MeOH+0.2% diethylamine in supercritical $CO_2$, 40° C., 150 bar back pressure); ESI mass spectrum: $[M+H]^+$=455. Yield: 12 mg Late eluting enantiomer (Example 9.56B): Retention time chiral HPLC=3.599 min (Daicel Chiralpak®IB, 4.6 mm×250 mm 5 μm, 4 ml/min, 10 min, 15% MeOH+0.2% diethylamine in supercritical $CO_2$, 40° C., 150 bar back pressure); ESI mass spectrum: $[M+H]^+$=455. Yield: 11 mg Examples 9.60-9.63 are prepared in two steps: (1) Amide coupling as described for preparation 13b employing the appropriate amines, respectively; (2) Alkylation as described for example 2.1, substituting benzyl bromide with 4-(1-bromo-ethyl)-benzonitrile and substituting preparation 5 with the appropriate intermediates from step 1, respectively. Intermediates from Step 1 (Amide Coupling)

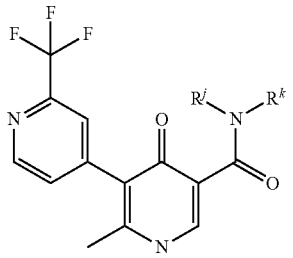

| Intermediate for Example . . . | $R^jR^kN$— | MS [M + H]$^+$ | Retention time HPLC/Method |
|---|---|---|---|
| 9.60 | 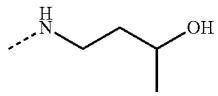 | 370 | 0.51 min Z018_S04 |
| 9.61 | 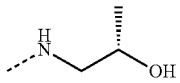 | 356 | 0.46 min Z011_S03 |
| 9.62 | 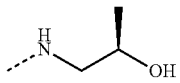 | 356 | 0.49 min Z011_S03 |
| 9.63 | 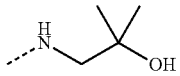 | 370 | 0.51 min Z011_S03 |

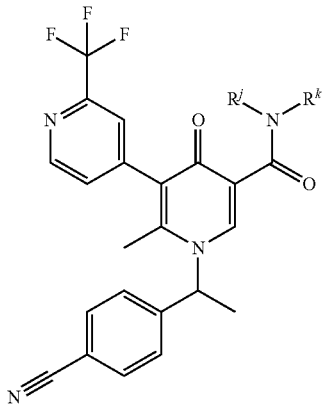

| Example | $R^jR^kN$— | MS [M + H]$^+$ | Retention time HPLC/Method |
|---|---|---|---|
| 9.60 | 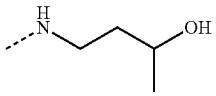 | 499 | 0.95 min Z018_S04 |
| 9.61 | 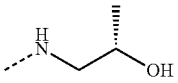 | 485 | 0.61 min 004_CA55 |
| 9.62 | 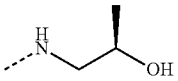 | 485 | 0.93 min Z018_S04 |
| 9.63 | 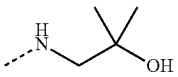 | 499 | 0.96 min Z018_S04 |

Example 10

1-[1-(4-Cyano-phenyl)-ethyl]-6-methyl-4-oxo-5-(3-trifluoromethyl-phenyl)-1,4-dihydro-pyridine-3-carboxylic acid ethylamide

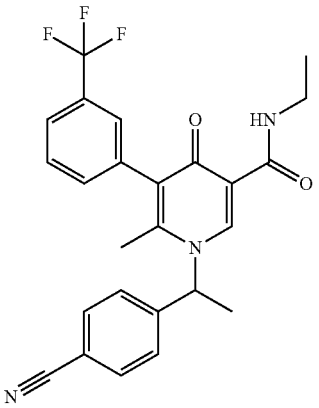

To a solution of 5-bromo-1-[1-(4-cyano-phenyl)-ethyl]-6-methyl-4-oxo-1,4-dihydro-pyridine-3-carboxylic acid ethylamide (preparation 10, 50 mg, 0.129 mmol), 3-trifluoromethyl-phenylboronic acid (29 mg, 0.155 mmol), 1,1'-[bis(diphenylphosphino)ferrocene]dichloropalladium(II) (9 mg, 0.012 mmol) in acetonitrile (1 mL) is added 2 M aqueous $K_2CO_3$ solution (0.20 mL, 0.40 mmol). After stirring for 24 h at 75° C., the reaction mixture is diluted with methanol and purified by preparative reversed-phase HPLC (XBridge, gradient of methanol in water, 0.1% $NH_4OH$, 60° C.). Yield: 56 mg (96% of theory); ESI mass spectrum: $[M+H]^+$=454; Retention time HPLC: 0.93 min (Z011_S03).

Example 10A and Example 10B

Enantiomers of Example 10

56 mg of racemic example 10 are separated by chiral HPLC (Daicel IB, 250 mm×20 mm, 20% MeOH+0.2% diethylamine in supercritical $CO_2$, 40° C.).

Early eluting enantiomer (Example 10A): Retention time chiral HPLC=1.62 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=454. Yield: 22 mg Late eluting enantiomer (Example 10B): Retention time chiral HPLC=1.99 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=454. Yield: 20 mg Example 11

1-[1-(4-Cyano-phenyl)-ethyl]-5-(3-difluoromethyl-phenyl)-6-methyl-4-oxo-1,4-dihydro-pyridine-3-carboxylic acid 4-methanesulfonyl-benzylamide

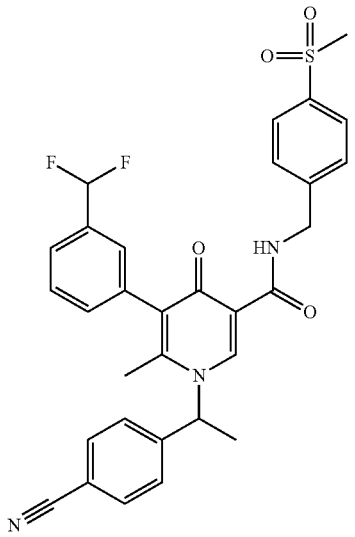

To a solution of 5-bromo-1-[1-(4-cyano-phenyl)-ethyl]-6-methyl-4-oxo-1,4-dihydro-pyridine-3-carboxylic acid 4-methanesulfonyl-benzylamide (preparation 11, 110 mg, 0.208 mmol), 3-difluoromethyl-phenylboronic acid (48 mg, 0.28 mmol), palladium (0) tetrakis(triphenylphosphine) (32 mg, 0.028 mmol) in acetonitrile (2 mL) is added 2 M aqueous $K_2CO_3$ solution (0.21 mL, 0.42 mmol). After stirring for 18 h at 75° C., the reaction mixture is diluted with methanol, acidified with acetic acid and purified by preparative reversed-phase HPLC (XBridge, gradient of methanol in water, 0.1% TFA, 60° C.). Yield: 90 mg (75% of theory); ESI mass spectrum: $[M+H]^+$=576; Retention time HPLC: 1.03 min (Z018_S04).

Example 11A and Example 11B

Enantiomers of Example 11

105 mg of racemic example 11 are separated by chiral HPLC (Daicel IB, 250 mm×20 mm, 30% MeOH+0.2% diethylamine in supercritical $CO_2$, 40° C.).

Early eluting enantiomer (Example 11A): Retention time chiral HPLC=2.519 min (Daicel Chiralpak®IB, 4.6 mm×250 mm 5 μm, 4 ml/min, 10 min, 30% MeOH+0.2% diethylamine in supercritical $CO_2$, 40° C., 150 bar back pressure); ESI mass spectrum: $[M+H]^+$=576. Yield: 33 mg Late eluting enantiomer (Example 11B): Retention time chiral HPLC=3.480 min (Daicel Chiralpak®IB, 4.6 mm×250 mm 5 μm, 4 ml/min, 10 min, 30% MeOH+0.2% diethylamine in supercritical $CO_2$, 40° C., 150 bar back pressure); ESI mass spectrum: $[M+H]^+$=576. Yield: 26 mg Example 12.1

(2-{[1-(4-Cyano-benzyl)-6-methyl-4-oxo-5-(3-trifluoromethyl-phenyl)-1,4-dihydro-pyridine-3-carbonyl]-amino}-ethyl)-trimethyl-ammonium chloride

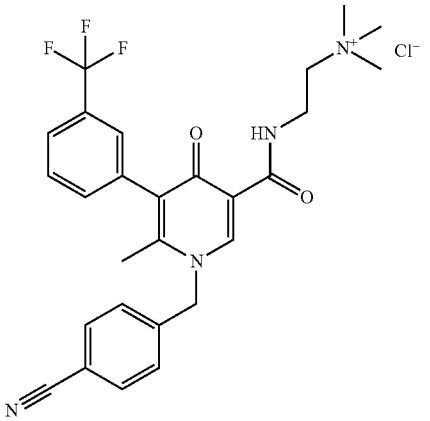

To a solution of example 1.6 (19 mg, 0.032 mmol) in acetonitrile (1 mL) is added $K_2CO_3$ (9 mg, 0.065 mmol) and methyl iodide (10 μL, 0.162 mmol). After stirring for 2 h at 55° C., the reaction mixture is acidified with glacial acetic acid and purified by preparative reversed-phase HPLC (Sunfire, gradient of methanol in water, 0.1% TFA, 60° C.). The product-containing fraction is acidified with 1N aqueous HCl, evaporated, re-dissolved in acetonitrile/1N aqueous HCl and lyophilized Yield: 17 mg (quantitative); ESI mass spectrum: $[M+H]^+$=497; Retention time HPLC: 1.16 min (Z002_005).

Example 12.2

(3-{[1-(4-Cyano-benzyl)-6-methyl-4-oxo-5-(3-trifluoromethyl-phenyl)-1,4-dihydro-pyridine-3-carbonyl]-amino}-propyl)-trimethyl-ammonium chloride

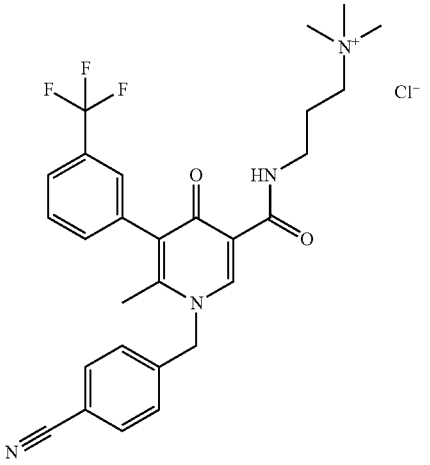

Example 12.2 is prepared as described for example 12.1, replacing example 1.6 with example 1.4 as starting material. ESI mass spectrum: $[M+H]^+$=511; Retention time HPLC: 1.16 min (Z002_005).

Example 12.3

4-({[1-(4-Cyano-benzyl)-6-methyl-4-oxo-5-(3-trifluoromethyl-phenyl)-1,4-dihydro-pyridine-3-carbonyl]-amino}-methyl)-1,1-dimethyl-piperidinium chloride

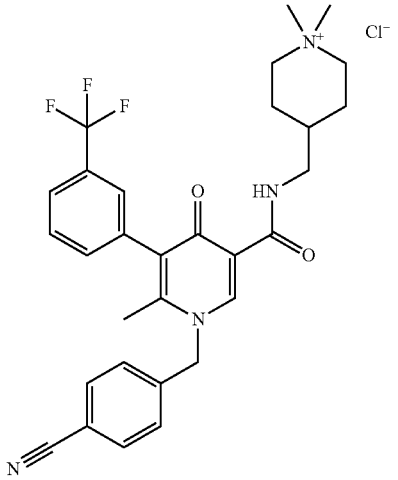

Example 12.3 is prepared as described for example 12.1, replacing example 1.6 with example 1.2 as starting material. ESI mass spectrum: $[M+H]^+$=537; Retention time HPLC: 1.18 min (Z002_005).

Example 12.4

{2-[4-({[1-(4-Cyano-benzyl)-6-methyl-4-oxo-5-(3-trifluoromethyl-phenyl)-1,4-dihydro-pyridine-3-carbonyl]-amino}-methyl)-piperidin-1-yl]-2-oxo-ethyl}-trimethyl-ammonium chloride

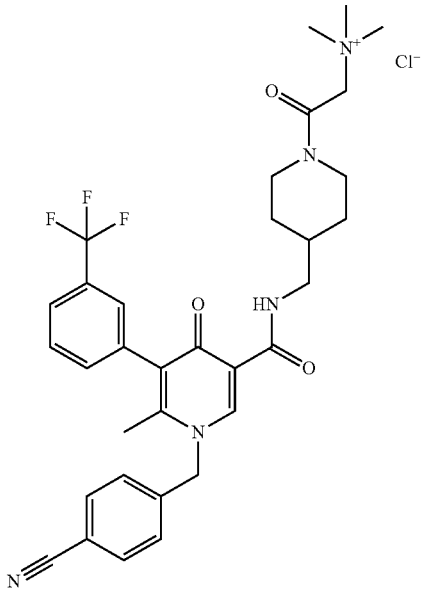

Example 12.4 is prepared as described for example 12.1, replacing example 1.6 with example 1.7 as starting material. ESI mass spectrum: $[M+H]^+$=608; Retention time HPLC: 1.21 min (Z002_005). Example 13.1

1-(4-Cyano-benzyl)-4-oxo-5-(3-trifluoromethyl-phenyl)-1,4-dihydro-pyridine-3-carboxylic acid 4-methanesulfonyl-benzylamide

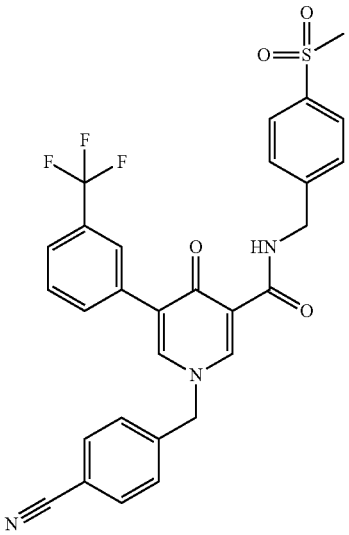

A solution of 1-(4-cyano-benzyl)-4-oxo-5-(3-trifluoromethyl-phenyl)-1,4-dihydro-m pyridine-3-carboxylic acid (preparation 12, 90 mg, 0.226 mmol), TBTU (74 mg, 0.231 mmol), DIPEA (100 µL, 0.585 mmol) in DMF (1 mL) is stirred for 15 min at room temperature. 4-Methylsulfonyl-benzylamine hydrochloride (55 mg, 0.248 mmol) is added and the reaction mixture is stirred for 18 h at room temperature. The reaction mixture is purified by preparative reversed-phase HPLC (XBridge, gradient of methanol in water, 0.1% $NH_4OH$, 60° C.). Yield: 41 mg (32% of theory); ESI mass spectrum: $[M+H]^+$=566; Retention time HPLC: 1.04 min (Z003_001).

Example 13.2

1-(4-Cyano-benzyl)-4-oxo-5-(3-trifluoromethyl-phenyl)-1,4-dihydro-pyridine-3-carboxylic acid (5-methanesulfonyl-pyridin-2-ylmethyl)-amide

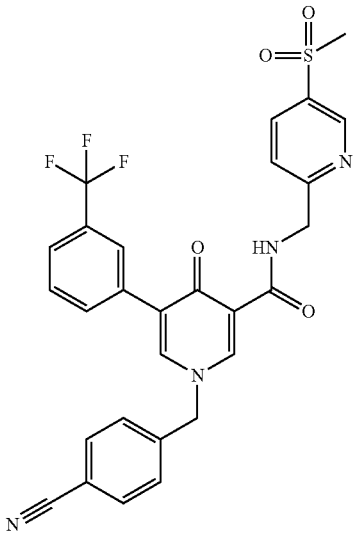

Example 13.2 is prepared as described for example 13.1, replacing 4-methylsulfonylbenzylamine hydrochloride with C-(5-methanesulfonyl-pyridin-2-yl)-methylamine. ESI mass spectrum: $[M+H]^+$=567; Retention time HPLC: 0.99 min (Z003_001).

Example 14

Pyridin-N-oxide of example 4.1

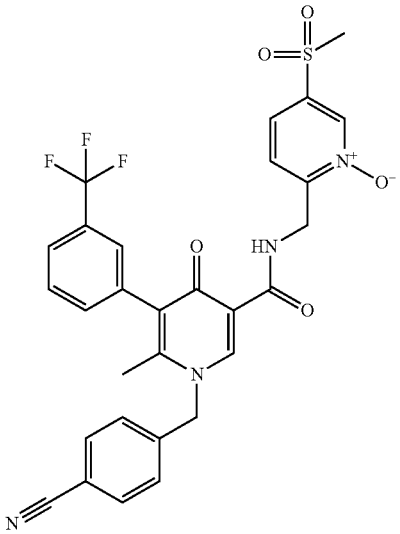

To a solution of 1-(4-cyano-benzyl)-6-methyl-4-oxo-5-(3-trifluoromethyl-phenyl)-1,4-dihydro-pyridine-3-carboxylic acid (5-methanesulfonyl-pyridin-2-ylmethyl)-amide (example 4.1, 34 mg, 0.059 mmol) in dichloromethane (2 mL) is added 3-chloroperoxybenzoic acid (MCPBA, 69 mg, 0.28 mmol). After stirring for 2 days at room temperature, the reaction mixture is purified by preparative reversed-phase HPLC (XBridge, gradient of methanol in water, 0.1% $NH_4OH$, 60° C.). Yield: 17 mg (49% of theory); ESI mass spectrum: $[M+H]^+$=597; Retention time HPLC: 1.13 min (Z003_003).

Example 15

1-[1-(5-Cyano-pyridin-2-yl)-ethyl]-2-methyl-4-oxo-2'-trifluoromethyl-1,4-dihydro-[3,4']bipyridinyl-5-carboxylic acid methylamide

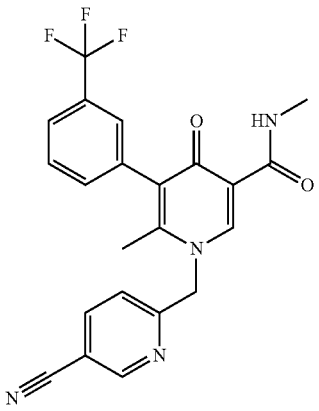

15a 6-(1-Bromo-ethyl)-nicotinonitrile

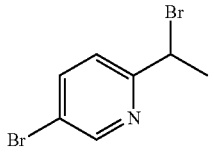

A solution of 5-bromo-2-ethylpyridine (500 mg, 2.69 mmol), N-bromosuccinimide (484 mg, 2.69 mmol) and 2,2'-azo-bis(isobutyronitrile) (5 mg, 0.03 mmol) in chloroform is heated at reflux for 2 h. After stirring over night at room temperature, the reaction mixture is filtered, evaporated under reduced pressure and purified by preparative reversed-phase HPLC (Gilson, XBridge, gradient of acetonitrile in water, 0.1% HCOOH). Yield: 37 mg (5% of theory); Retention time HPLC: 0.89 min (Z011_S03).

15b 1-[1-(5-Bromo-pyridin-2-yl)-ethyl]-2-methyl-4-oxo-2'-trifluoromethyl-1,4-dihydro-[3,4']bipyridinyl-5-carboxylic acid methylamide

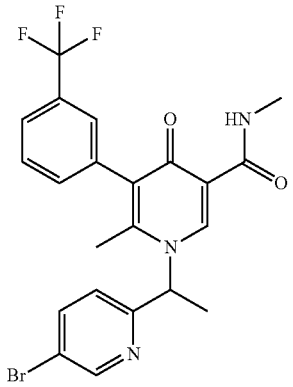

Preparation 15b is prepared as described for example 2.1, substituting benzyl bromide with preparation 15a, substituting preparation 5 with preparation 6 and DMF with NMP. ESI mass spectrum: $[M+H]^+$=494 (bromine pattern); Retention time HPLC: 1.51 min (Z002_006).

15c 6-(1-Bromo-ethyl)-nicotinonitrile

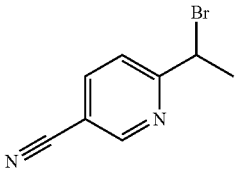

A solution of 6-ethyl-nicotinonitrile (synthesis described in WO2008/71404, 1000 mg, 7.57 mmol), N-bromosuccinimide (1632 mg, 9.08 mmol) and 2,2'-azo-bis(isobutyronitrile) (62 mg, 0.38 mmol) in chloroform (12 mL) is heated at reflux for 7 min. After cooling to room temperature, the reaction mixture is filtered and the volatiles are removed under reduced pressure (260 mbar, 55° C.) to yield the product which was used without further purification. Yield: 1597 mg (quant.); ESI mass spectrum: $[M+H]^+$=211 (Br pattern); Retention time HPLC: 0.92 min (Z018_S04).

Example 15

1-[1-(5-Cyano-pyridin-2-yl)-ethyl]-2-methyl-4-oxo-2'-trifluoromethyl-1,4-dihydro-[3,4']bipyridinyl-5-carboxylic acid methylamide

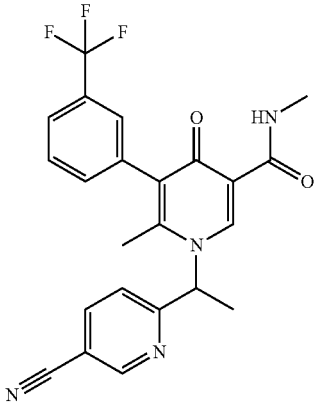

A solution of preparation 15b (42 mg, 85 μmol), zinc cyanide (13 mg, 111 μmol) and Pd-tetrakis(triphenylphosphine) (5 mg) in DMF (0.5 mL) is heated overnight at 110° C. After cooling to room temperature, the reaction mixture is filtered and purified by preparative reversed-phase HPLC (Gilson, XBridge, gradient of acetonitrile in water, 0.1% HCOOH). Yield: 9 mg (37% of theory); ESI mass spectrum: $[M+H]^+$=441; Retention time HPLC: 1.37 min (Z002_006).

Alternatively, example 15 is prepared as described for example 2.1, substituting benzyl bromide with preparation 15c, substituting preparation 5 with preparation 6 and DMF with NMP.

Example 15A and Example 15B

Enantiomers of Example 15

58 mg of racemic example 15 are separated by chiral HPLC (Daicel IB, 250 mm×20 mm, 20% MeOH+0.2% diethylamine in supercritical $CO_2$, 40° C., 10 mL/min)

Early eluting enantiomer (Example 15A): Retention time chiral HPLC=1.858 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=441. Yield: 15 mg Late eluting enantiomer (Example 15B): Retention time chiral HPLC=2.633 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=441. Yield: 13 mg Example 16

1-[1-(5-Cyano-pyridin-2-yl)-ethyl]-5-(3-difluoromethyl-phenyl)-6-methyl-4-oxo-1,4-dihydro-pyridine-3-carboxylic acid methylamide

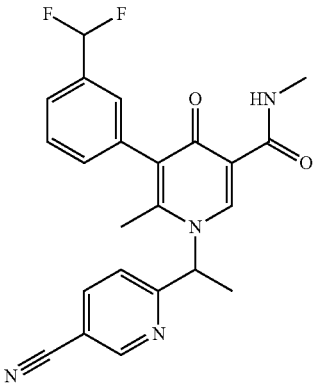

16a 5-(3-Difluoromethyl-phenyl)-6-methyl-4-oxo-1,4-dihydro-pyridine-3-carboxylic acid

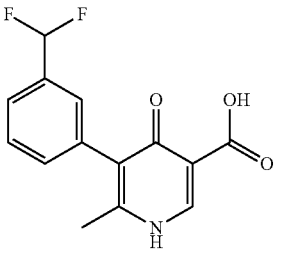

Preparation 16a is prepared as described for preparation 5b, substituting 3-(trifluoromethyl)phenylboronic acid with 3-(difluoromethyl)phenylboronic acid. ESI mass spectrum: $[M+H]^+$=280; Retention time HPLC: 1.51 min (Z018_S04).

16b 5-(3-Difluoromethyl-phenyl)-6-methyl-4-oxo-1,4-dihydro-pyridine-3-carboxylic acid methylamide

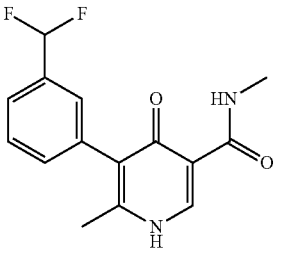

A solution of 5-(3-difluoromethyl-phenyl)-6-methyl-4-oxo-1,4-dihydro-pyridine-3-carboxylic acid (preparation 16a, 931 mg, 3.33 mmol), TBTU (1.17 g, 3.64 mmol), triethylamine (0.94 mL, 6.70 mmol) in DMF (3 mL) is stirred for 30 min. Then, methylamine (5.23 mL of 2M solution in THF, 10.5 mmol) is added and the reaction mixture is stirred for 18 h at room temperature. The reaction mixture is concentrated under reduced pressure and purified by preparative reversed-phase HPLC (XBridge, gradient of acetonitrile in water, 0.3% $NH_4OH$, 60° C.). Yield: 0.25 g (25% of theory); ESI mass spectrum: $[M+H]^+$=293; Retention time HPLC: 0.59 min (Z011_S03).

16c 1-[1-(5-Bromo-pyridin-2-yl)-ethyl]-5-(3-difluoromethyl-phenyl)-6-methyl-4-oxo-1,4-dihydro-pyridine-3-carboxylic acid methylamide

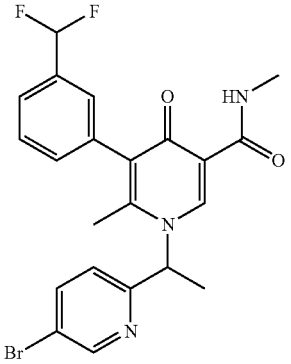

Preparation 16c is prepared as described for example 2.1, substituting benzyl bromide with preparation 15a, substituting preparation 5 with preparation 16b and DMF with NMP. ESI mass spectrum: $[M+H]^+$=476 (bromine pattern); Retention time HPLC: 1.02 min (Z018_S04).

Example 16

1-[1-(5-Cyano-pyridin-2-yl)-ethyl]-5-(3-difluoromethyl-phenyl)-6-methyl-4-oxo-1,4-dihydro-pyridine-3-carboxylic acid methylamide

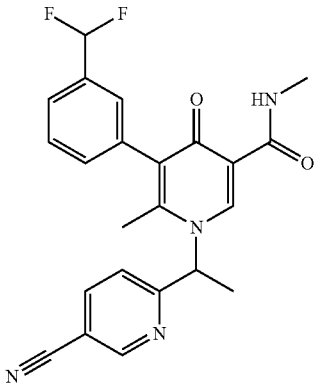

Example 16 is prepared as described for Example 15, substituting preparation 15b with preparation 16c. ESI mass spectrum: $[M+H]^+$=423; Retention time HPLC: 0.94 min (Z018_S04).

Example 16A and Example 16B

Enantiomers of Example 16

86 mg of racemic example 16 are separated by chiral HPLC (Daicel IB, 250 mm×20 mm, 20% MeOH+0.2% diethylamine in supercritical $CO_2$, 40° C., 10 mL/min)

Early eluting enantiomer (Example 16A): Retention time chiral HPLC=2.351 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=423. Yield: 31 mg Late eluting enantiomer (Example 16B): Retention time chiral HPLC=3.507 min (Daicel Chiralpak®IB, 4.6 mm×250 mm 5 μm, 4 ml/min, 10 min, 20% MeOH+0.2% diethylamine in supercritical $CO_2$, 40° C., 150 bar back pressure); ESI mass spectrum: $[M+H]^+$=423. Yield: 32 mg Example 17

1-[1-(5-Cyano-pyridin-2-yl)-ethyl]-6-methyl-4-oxo-5-(3-trifluoromethyl-phenyl)-1,4-dihydro-pyridine-3-carboxylic acid ethylamide

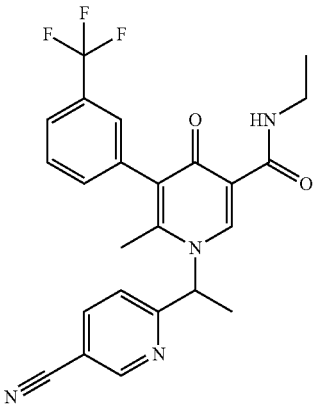

17a 6-Methyl-4-oxo-5-(3-trifluoromethyl-phenyl)-1,4-dihydro-pyridine-3-carboxylic acid ethylamide

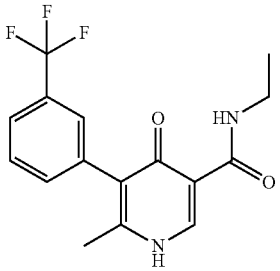

Preparation 17a is prepared as described for preparation 6 and substituting methylamine with ethylamine. ESI mass spectrum: $[M+H]^+$=325; Retention time HPLC: 0.70 min (Z011_S03).

17b 1-[1-(5-Bromo-pyridin-2-yl)-ethyl]-6-methyl-4-oxo-5-(3-trifluoromethyl-phenyl)-1,4-dihydro-pyridine-3-carboxylic acid ethylamide

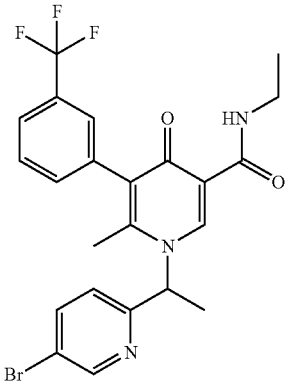

Preparation 17b is prepared as described for example 2.1, substituting benzyl bromide with preparation 15a, substituting preparation 5 with preparation 17a and DMF with NMP. ESI mass spectrum: $[M+H]^+$=508 (bromine pattern); Retention time HPLC: 1.26 min (Z018_S04).

Example 17

1-[1-(5-Cyano-pyridin-2-yl)-ethyl]-6-methyl-4-oxo-5-(3-trifluoromethyl-phenyl)-1,4-dihydro-pyridine-3-carboxylic acid ethylamide

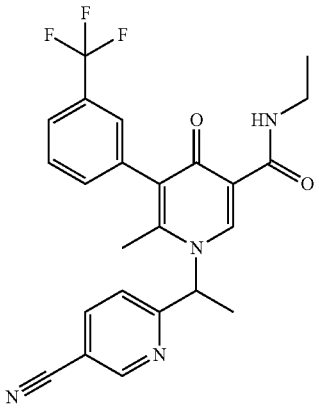

Example 17 is prepared as described for Example 15, substituting preparation 15b with preparation 17b. ESI mass spectrum: [M+H]=455; Retention time HPLC: 1.03 min (Z018_S04).

Example 18

1-[1-(5-Cyano-pyridin-2-yl)-ethyl]-5-(3-difluoromethyl-phenyl)-6-methyl-4-oxo-1,4-dihydro-pyridine-3-carboxylic acid ethylamide

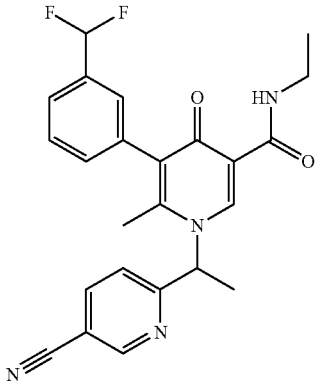

18a 5-(3-Difluoromethyl-phenyl)-6-methyl-4-oxo-1,4-dihydro-pyridine-3-carboxylic acid ethylamide

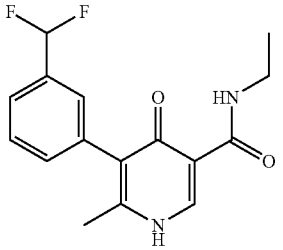

Preparation 18a is prepared as described for preparation 6, substituting preparation 5b with preparation 16a and methylamine with ethylamine. ESI mass spectrum: $[M+H]^+$=307; Retention time HPLC: 0.62 min (Z011_S03).

18b 1-[1-(5-Bromo-pyridin-2-yl)-ethyl]-5-(3-difluoromethyl-phenyl)-6-methyl-4-oxo-1,4-dihydro-pyridine-3-carboxylic acid ethylamide

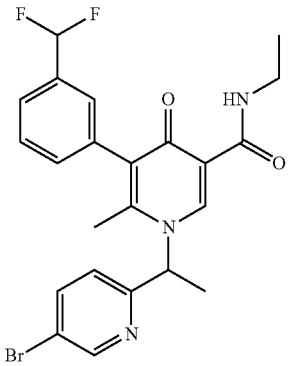

Preparation 18b is prepared as described for example 2.1, substituting benzyl bromide with preparation 15a, substituting preparation 5 with preparation 18a and DMF with NMP. ESI mass spectrum: $[M+H]^+$=490 (bromine pattern); Retention time HPLC: 1.06 min (Z018_S04).

Example 18

1-[1-(5-Cyano-pyridin-2-yl)-ethyl]-5-(3-difluoromethyl-phenyl)-6-methyl-4-oxo-1,4-dihydro-pyridine-3-carboxylic acid ethylamide

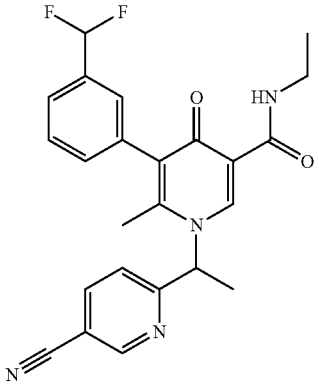

Example 18 is prepared as described for Example 15, substituting preparation 15b with preparation 18b. ESI mass spectrum: $[M+H]^+$=437; Retention time HPLC: 0.76 min (002_CA03).

Example 19

1-[1-(5-Cyano-pyridin-2-yl)-ethyl]-2-methyl-4-oxo-2'-trifluoromethyl-1,4-dihydro-[3,4']bipyridinyl-5-carboxylic acid ethylamide

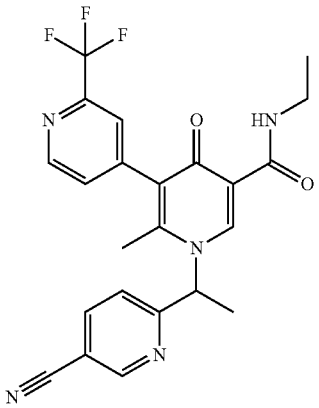

19a 2-Methyl-4-oxo-2'-trifluoromethyl-1,4-dihydro-[3,4']bipyridinyl-5-carboxylic acid ethylamide

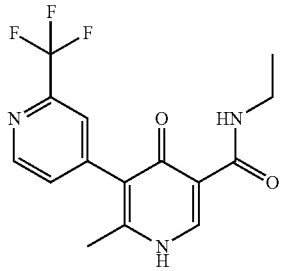

Preparation 19a is prepared as described for preparation 16b, substituting preparation 16a with preparation 13a and methylamine with ethylamine. ESI mass spectrum: $[M+H]^+$=326; Retention time HPLC: 0.84 min (Z018_S04).

19b 1-[1-(5-Bromo -pyridin-2-yl)-ethyl]-2-methyl-4-oxo-2'-trifluoromethyl-1,4-dihydro-[3,4']bipyridinyl-5-carboxylic acid ethylamide

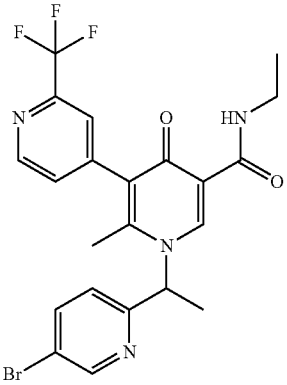

Preparation 19b is prepared as described for example 2.1, substituting benzyl bromide with preparation 15a, substituting preparation 5 with preparation 19a and DMF with NMP. ESI mass spectrum: $[M+H]^+$=509 (bromine pattern); Retention time HPLC: 1.04 min (Z018_S04).

Example 19

1-[1-(5-Cyano-pyridin-2-yl)-ethyl]-2-methyl-4-oxo-2'-trifluoromethyl-1,4-dihydro-[3,4']bipyridinyl-5-carboxylic acid ethylamide

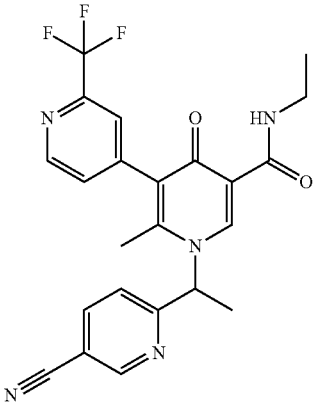

Example 19c is prepared as described for Example 15, substituting preparation 15b with preparation 19b. ESI mass spectrum: $[M+H]^+$=456; Retention time HPLC: 0.96 min (Z018_S04).

Examples 20-24. are prepared in three steps: (1) Amide coupling as described for preparation 6, employing the appropriate amines, respectively; (2) Alkylation as described for example 2.1, substituting preparation 5 with the corresponding intermediates from step 1 and substituting DMF with NMP; (3) Cyanation as described for Example 15, substituting preparation 15b with the corresponding intermediates from step 2.

Intermediates from Step 1 (Amide Coupling)

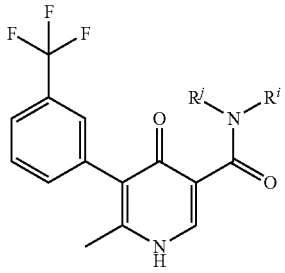

| Intermediate for Example . . . | $R^jR^kN$— | MS $[M + H]^+$ | Retention time HPLC/ Method |
|---|---|---|---|
| 20 (Preparation 6) | 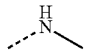 | 311 | 1.10 min V003_003 |
| 21 | 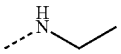 | 325 | 0.70 min Z011_S03 |
| 22 | 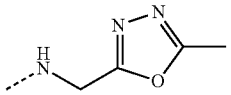 | 393 | 0.64 mi Z011_S03 |
| 23 | 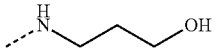 | 355 | 0.63 min Z011_S03 |
| 24 | 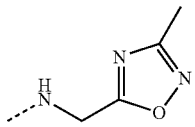 | 393 | 0.65 min Z011_S03 |

Intermediates from Step 2 (Alkylation)
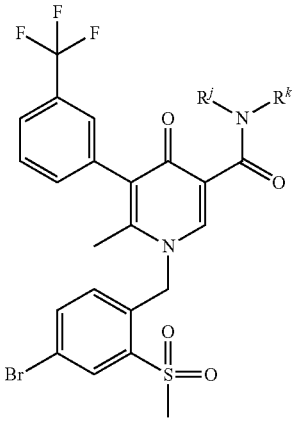
| Intermediate for Example... | $R^jR^kN$— | MS $[M + H]^+$ | Retention time HPLC/ Method |
|---|---|---|---|
| 20 | 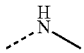 | 557 | 0.93 min Z011_S03 |
| 21 | 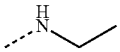 | 571 | 0.96 min Z011_S03 |
| 22 | 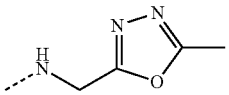 | 639 | 0.91 min Z011_S03 |
| 23 | 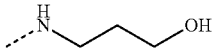 | 601 | 0.90 min Z011_S03 |
| 24 | 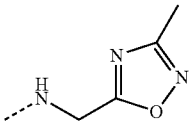 | 639 | 0.95 min Z011_S03 |
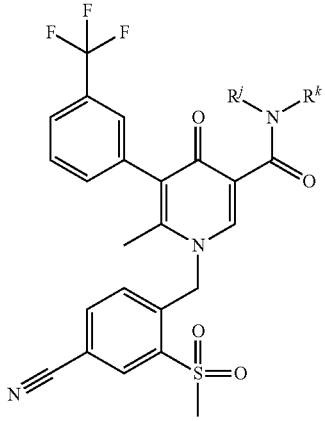
| Example | $R^jR^kN$— | MS $[M + H]^+$ | Retention time HPLC/Method |
|---|---|---|---|
| 20 | 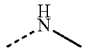 | 504 | 0.85 min Z011_S03 |
| 21 | 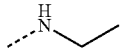 | 518 | 1.01 min Z012_S04 |
| 22 | 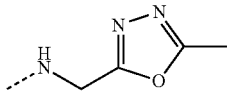 | 586 | 0.91 min Z011_S03 |
| 23 | 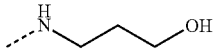 | 548 | 1.36 min Z002_006 |
| 24 | 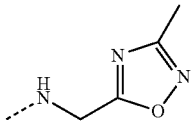 | 586 | 1.39 min Z002_006 |
Example 25
1-[4-Cyano-2-(propane-1-sulfonyl)-benzyl]-6-methyl-4-oxo-5-(3-trifluoromethyl-phenyl)-1,4-dihydro-pyridine-3-carboxylic acid methylamide
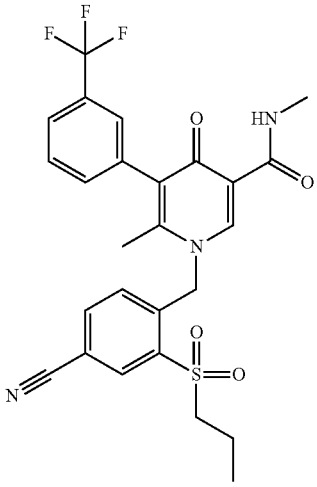

25a 1-(2-Bromo-4-cyano-benzyl)-6-methyl-4-oxo-5-(3-trifluoromethyl-phenyl)-1,4-dihydro-pyridine-3-carboxylic acid methylamide

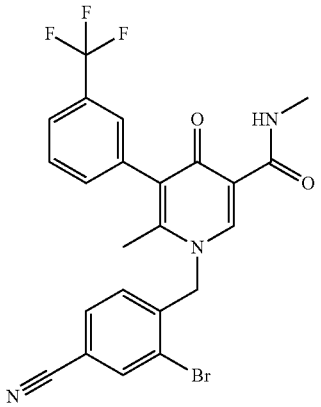

Preparation 25a is prepared as described for example 2.1, substituting benzyl bromide with 2-bromo-4-cyanobenzyl bromide and DMF with NMP. ESI mass spectrum: $[M+H]^+$=504 (bromine pattern); Retention time HPLC: 1.06 min (Z018_S04).

Example 25

1-[4-Cyano-2-(propane-1-sulfonyl)-benzyl]-6-methyl-4-oxo-5-(3-trifluoromethyl-phenyl)-1,4-dihydro-pyridine-3-carboxylic acid methylamide

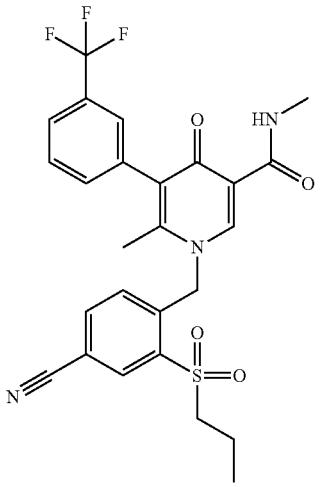

A mixture of preparation 25a (70 mg, 139 μmol), sodium 1-propylsulfinate (54 mg, 415 μmol), L-proline (20 mg, 174 μmol), CuI (7 mg, 37 μmol), $K_2CO_3$ (24 mg, 174 μmol) in DMSO (0.7 mL) is heated 60 min at 110° C. The reaction mixture is purified by preparative reversed-phase HPLC (XBridge, gradient of methanol in water, 0.3% $NH_4OH$, 60° C.). Yield: 11 mg (15% of theory); ESI mass spectrum: $[M+H]^+$=532; Retention time HPLC: 1.06 min (Z003_001).

Examples 26 and 27 are prepared as described for example 25, employing the appropriate sulfinates, respectively.

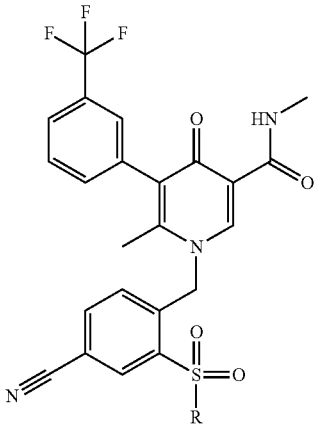

| Example | R | MS $[M + H]^+$ | Retention time HPLC/Method |
|---|---|---|---|
| 26 | Ethyl | 518 | 1.03 min Z018_504 |
| 27 | Cyclopropyl | 530 | 0.59 min 001_CA07 |

Examples 28-30 are prepared as described for example 9, substituting 2-(trifluoromethyl)pyridine-4-boronic acid with the boronic acids or esters indicated in the table below.

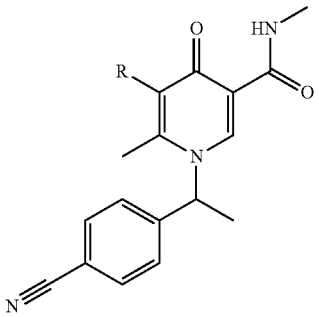

| Example | Boronic Acid or Boronic Ester | MS $[M + H]^+$ | Retention time HPLC/Method |
|---|---|---|---|
| 28 | 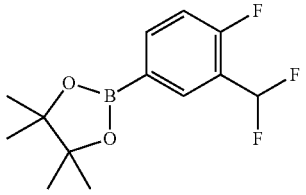 | 440 | 0.84 min Z011_S03 |
| 29 | 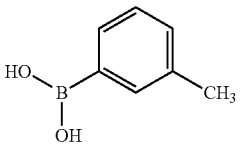 | 386 | 0.98 min Z018_S04 |

-continued

| Example | Boronic Acid or Boronic Ester | MS [M + H]+ | Retention time HPLC/ Method |
|---|---|---|---|
| 30 | 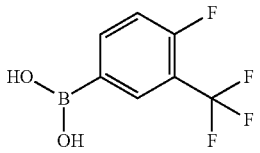 | 458 | 1.04 min Z018_S04 |

Example 31

1-[1-(4-Cyano-phenyl)-ethyl]-5-(3-fluoromethyl-phenyl)-6-methyl-4-oxo-1,4-dihydro-pyridine-3-carboxylic acid methylamide

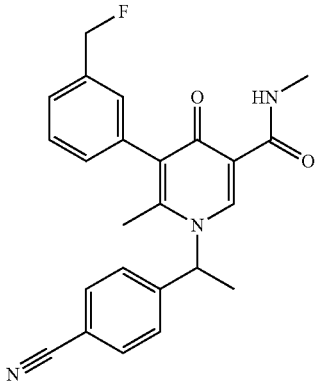

31a 1-[1-(4-Cyano-phenyl)-ethyl]-5-(3-hydroxymethyl-phenyl)-6-methyl-4-oxo-1,4-dihydro-pyridine-3-carboxylic acid methylamide

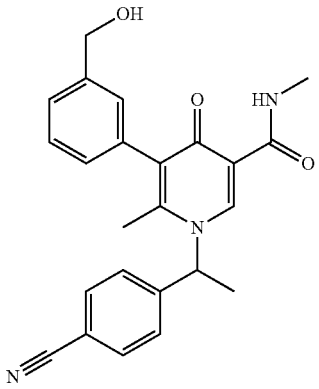

Preparation 31a is prepared as described for example 9, substituting 2-(trifluoromethyl)pyridine-4-boronic acid with 3-(hydroxymethyl)phenylboronic acid. ESI mass spectrum: $[M+H]^+$=402; Retention time HPLC: 0.69 min (Z011_S03).

Example 31

1-[1-(4-Cyano-phenyl)-ethyl]-5-(3-fluoromethyl-phenyl)-6-methyl-4-oxo-1,4-dihydro-pyridine-3-carboxylic acid methylamide

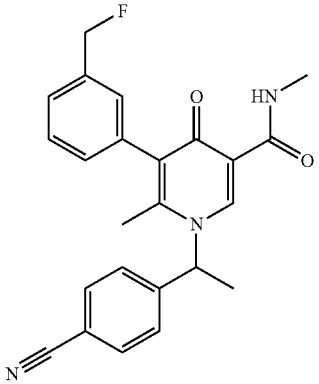

A solution of preparation 31a (60 mg, 149 μmol) and [bis(2-methoxyethyl)amino]sulfur trifluoride (50% in toluene, 74 μL, 202 μmol) in dichloromethane (1 mL) is stirred for 3 h at room temperature. The reaction mixture is quenched with 1N HCl, extracted twice with dichloromethane and the organic phase is concentrated under reduced pressure. The remaining residue is purified by preparative reversed-phase HPLC (Stable Bond, gradient of acetonitrile in water, 0.1% TFA, 60° C.). Yield: 30 mg (50% of theory); ESI mass spectrum: $[M+H]^+$=404; Retention time HPLC: 0.95 min (Z017_504).

xample 31A and Example 31B

Enantiomers of Example 31

25 mg of racemic example 31 are separated by chiral HPLC (Daicel IB, 250 mm×20 mm, 25% MeOH+0.2% diethylamine in supercritical $CO_2$, 40° C., 10 mL/min)

Early eluting enantiomer (Example 31A): Retention time chiral HPLC=4.172 min (Daicel Chiralpak®IB, 4.6 mm×250 mm 5 μm, 4 ml/min, 10 min, 25% MeOH+0.2% diethylamine in supercritical $CO_2$, 40° C., 150 bar back pressure); ESI mass spectrum: $[M+H]^+$=404. Yield: 11 mg Late eluting enantiomer (Example 31B): Retention time chiral HPLC=5.707 min (Daicel Chiralpak®IB, 4.6 mm×250 mm 5 μm, 4 ml/min, 10 min, 25% MeOH+0.2% diethylamine in supercritical $CO_2$, 40° C., 150 bar back pressure); ESI mass spectrum: $[M+H]^+$=404. Yield: 10 mg Examples 32-34 are prepared as described for example 2.1, substituting benzyl bromide with the appropriate aryl- or heteroaryl-methyl bromides and substituting preparation 5 with preparation 16b.

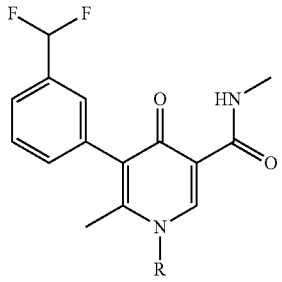

| Example | R | MS [M + H]$^+$ | Retention time HPLC/Method |
|---|---|---|---|
| 32 | 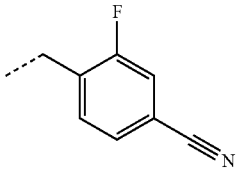 | 426 | 0.98 Z018_S04 |
| 33 | 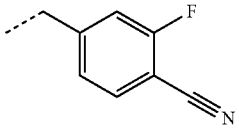 | 426 | 0.99 min Z018_S04 |
| 34 | 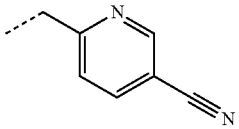 | 409 | 0.99 min Z018_S04 |

Example 35

1-[1-(4-Cyano-phenyl)-propyl]-6-methyl-4-oxo-5-(3-trifluoromethyl-phenyl)-1,4-dihydro-pyridine-3-carboxylic acid ethylamide

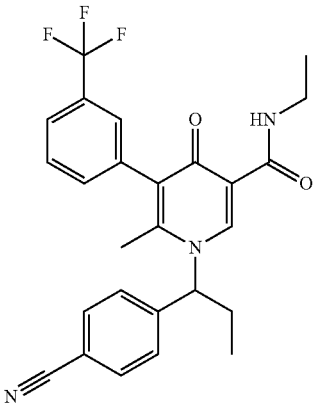

35a 1-[1-(4-Bromo -phenyl)-propyl]-6-methyl-4-oxo -5-(3-trifluoromethyl-phenyl)-1,4-dihydro-pyridine-3-carboxylic acid ethylamide

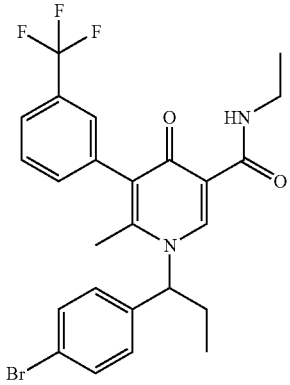

Preparation 35a is prepared as described for example 2.1, substituting benzyl bromide with 1-bromo-4-(1-bromopropyl)benzene and substituting preparation 5 with preparation 17a. ESI mass spectrum: [M+H]$^+$=521 (bromine pattern); Retention time HPLC: 1.21 min (Z018_S04).

Example 35

1-[1-(4-Cyano-phenyl)-propyl]-6-methyl-4-oxo-5-(3-trifluoromethyl-phenyl)-1,4-dihydro-pyridine-3-carboxylic acid ethylamide

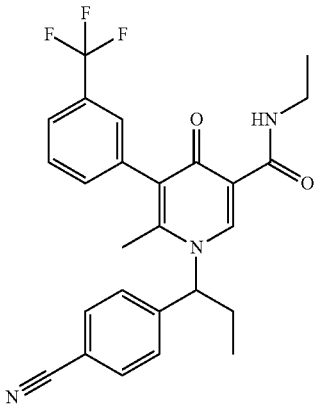

Example 35 is prepared as described for Example 15, substituting preparation 15b with preparation 35a. ESI mass spectrum: [M+H]$^+$=468; Retention time HPLC: 0.51 min (Z011_S03).

Example 36

1-[1-(4-Cyano-phenyl)-propyl]-2-methyl-4-oxo-2'-trifluoromethyl-1,4-dihydro-[3,4']bipyridinyl-5-carboxylic acid methylamide

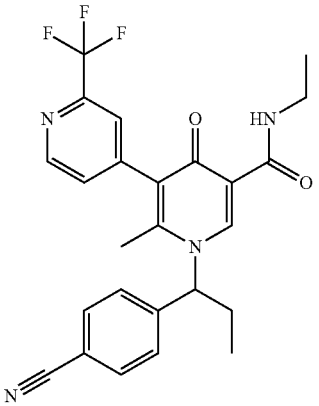

36a 2-Methyl-4-oxo-2'-trifluoromethyl-1,4-dihydro-[3,4']bipyridinyl-5-carboxylic acid methylamide

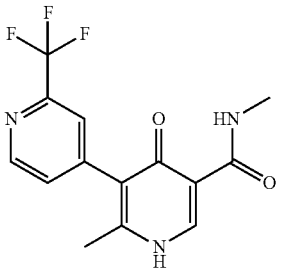

Preparation 36a is prepared as described for preparation 16b, substituting preparation 16a with preparation 13a. ESI mass spectrum: $[M+H]^+$=312.

36b 1-[1-(4-Bromo-phenyl)-propyl]-2-methyl-4-oxo-2'-trifluoromethyl-1,4-dihydro-[3,4']bipyridinyl-5-carboxylic acid methylamide

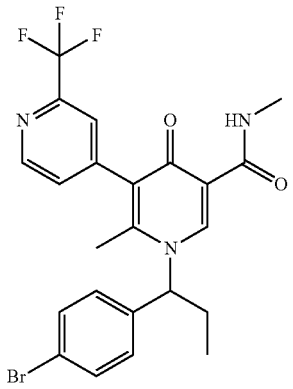

Preparation 36b is prepared as described for example 2.1, substituting benzyl bromide with 1-bromo-4-(1-bromopropyl)benzene and substituting preparation 5 with preparation 36a. ESI mass spectrum: $[M+H]^+$=508 (bromine pattern); Retention time HPLC: 1.08 min (Z018_S04).

Example 36

1-[1-(4-Cyano-phenyl)-propyl]-2-methyl-4-oxo-2'-trifluoromethyl-1,4-dihydro-[3,4']bipyridinyl-5-carboxylic acid methylamide

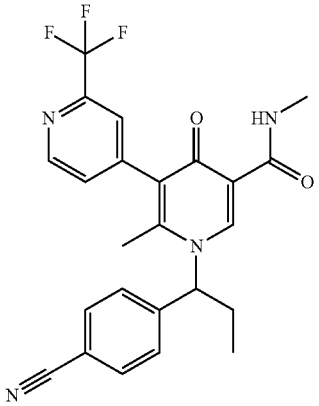

Example 36 is prepared as described for Example 15, substituting preparation 15b with preparation 36b. ESI mass spectrum: $[M+H]^+$=455; Retention time HPLC: 0.85 min (Z011_S03).

Example 37

1-(5-Cyano-indan-1-yl)-6-methyl-4-oxo-5-(3-trifluoromethyl-phenyl)-1,4-dihydro-pyridine-3-carboxylic acid methylamide

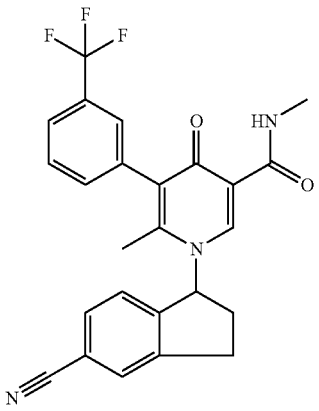

37a 1-(5-Bromo-indan-1-yl)-6-methyl-4-oxo-1,4-dihydro-pyridine-3-carboxylic acid

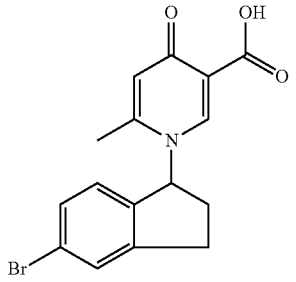

Preparation 37a is prepared as described for preparation 1b, substituting 4-cyanobenzylamine hydrochloride with 5-bromo-2,3-dihydro-1H-inden-1-amine. ESI mass spectrum: $[M+H]^+$=348 (bromine pattern); Retention time HPLC: 0.93 min (Z018_S04).

37b 1-(5-Cyano-indan-1-yl)-6-methyl-4-oxo-1,4-dihydro-pyridine-3-carboxylic acid

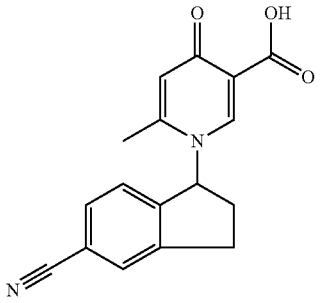

Preparation 37b is prepared as described for Example 15, substituting preparation 15b with preparation 37a. ESI mass spectrum: $[M+H]^+$=295; Retention time HPLC: 0.34 min (Z011_S03).

37c 5-Bromo-1-(5-cyano-indan-1-yl)-6-methyl-4-oxo-1,4-dihydro-pyridine-3-carboxylic acid

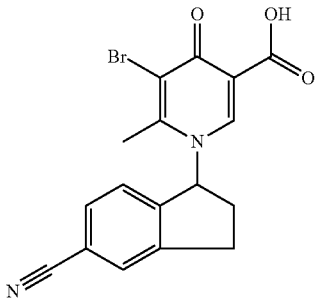

Preparation 37c is prepared as described for preparation 1c, substituting preparation 1b with preparation 37b. ESI mass spectrum: $[M+H]^+$=373; Retention time HPLC: 0.91 min (Z018_S04).

37d 1-(5-Cyano-indan-1-yl)-6-methyl-4-oxo-5-(3-trifluoromethyl-phenyl)-1,4-dihydro -pyridine-3-carboxylic acid

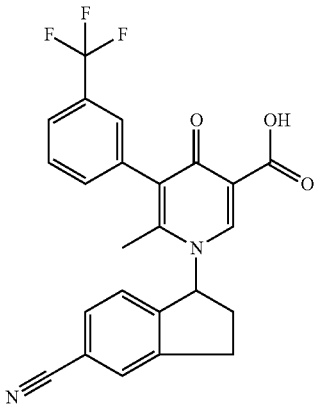

Preparation 37d is prepared as described for preparation 5b, substituting preparation 5a with preparation 37c. ESI mass spectrum: $[M+H]^+$=439; Retention time HPLC: 1.05 min (Z018_S04).

Example 37

1-(5-Cyano-indan-1-yl)-6-methyl-4-oxo-5-(3-trifluoromethyl-phenyl)-1,4-dihydro-pyridine-3-carboxylic acid methylamide

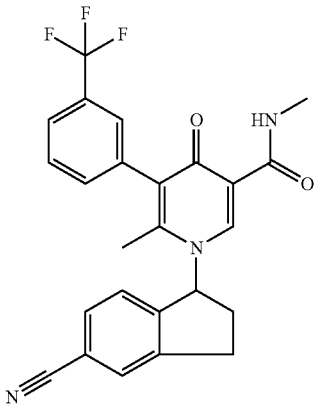

Example 37 is prepared as described for example 1.17, substituting 3-amino-1,2-propanediol with methylamine. ESI mass spectrum: $[M+H]^+$=452; Retention time HPLC: 0.90 min (Z011_S03).

Example 38

1-[1-(4-Cyano-phenyl)-ethyl]-2'-difluoromethyl-2-methyl-4-oxo-1,4-dihydro-[3,4']bipyridinyl-5-carboxylic acid ethylamide

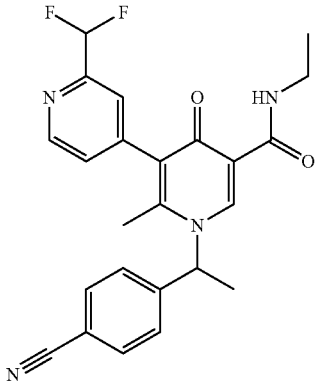

38a 2-(Difluoromethyl)pyridine-4-boronic acid

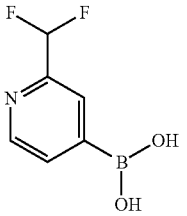

A mixture of 4-bromo-2-(difluoromethyl)pyridine (2.50 g, 12.0 mmol), bis-(pinakolato)-diboron (3.80 g, 15.0 mmol), (1,1'-Bis-(diphenylphosphino)-ferrocen)-dichlorpalladium (II) (26 mg, 36 μmol) and potassium acetate (2.90 g, 30.0 mmol) in dioxane is stirred for 48 h at 80° C. The volatiles are removed under reduced pressure. After addition of water, the mixture is extracted with dichloromethane. The combined organic layer is dried over $Na_2SO_4$ and evaporated under reduced pressure. The remaining residue is purified by preparative reversed phase HPLC (Sunfire, gradient of acetonitrile in water, 0.1% HCOOH). Yield: 599 mg of the desired boronic acid (60% pure, 17% of theory).

Example 38

1-[1-(4-Cyano-phenyl)-ethyl]-2'-difluoromethyl-2-methyl-4-oxo-1,4-dihydro-[3,4']bipyridinyl-5-carboxylic acid ethylamide

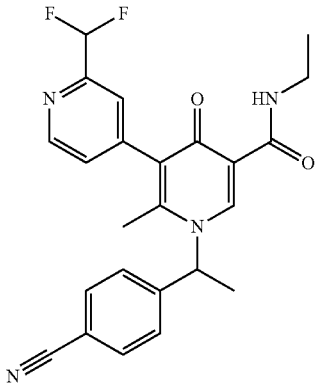

Example 38 is prepared as described for example 10, substituting 3-trifluoromethyl-phenylboronic acid with preparation 38a. ESI mass spectrum: $[M+H]^+$=437; Retention time HPLC: 0.77 min (Z011_S03).

Example 39

1-(4-Cyano-3-fluoro-benzyl)-5-(3-difluoromethyl-phenyl)-6-methyl-4-oxo-1,4-dihydro-pyridine-3-carboxylic acid 4-methanesulfonyl-benzylamide

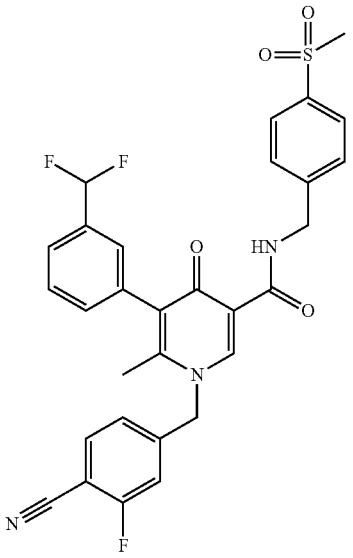

39a 5-(3-Difluoromethyl-phenyl)-6-methyl-4-oxo-1,4-dihydro-pyridine-3-carboxylic acid 4-methanesulfonyl-benzylamide

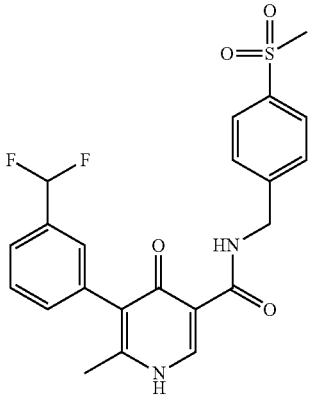

Preparation 39a is prepared as described for preparation 5c, substituting preparation 5b with preparation 16a. ESI mass spectrum: $[M+H]^+$=447; Retention time HPLC: 0.66 min (Z011_S03).

Example 39

1-(4-Cyano-3-fluoro-benzyl)-5-(3-difluoromethyl-phenyl)-6-methyl-4-oxo-1,4-dihydro-pyridine-3-carboxylic acid 4-methanesulfonyl-benzylamide

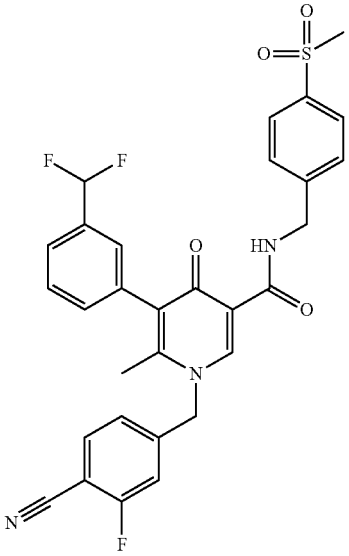

Example 39 is prepared as described for example 2.1, substituting benzyl bromide with 4-bromomethyl-2-fluorobenzonitrile and substituting preparation 5 with preparation 39a. ESI mass spectrum: $[M+H]^+$=580; Retention time HPLC: 1.03 min (Z018_S04).

Example 40

1-(5-Cyano-pyridin-2-ylmethyl)-5-(3-difluoromethyl-phenyl)-6-methyl-4-oxo-1,4-dihydro-pyridine-3-carboxylic acid 4-methanesulfonyl-benzylamide

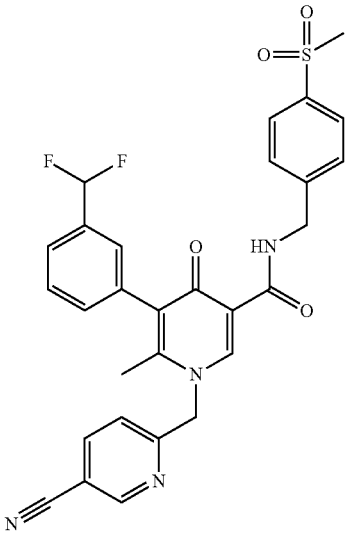

Example 40 is prepared as described for example 2.1, substituting benzyl bromide with 6-bromomethyl-nicotinonitrile and substituting preparation 5 with preparation 39a. ESI mass spectrum: $[M+H]^+$=563; Retention time HPLC: 0.99 min (Z018_S04).

Example 41

1-(4-Cyano-2-fluoro-benzyl)-5-(3-difluoromethyl-phenyl)-6-methyl-4-oxo-1,4-dihydro-pyridine-3-carboxylic acid 4-methanesulfonyl-benzylamide

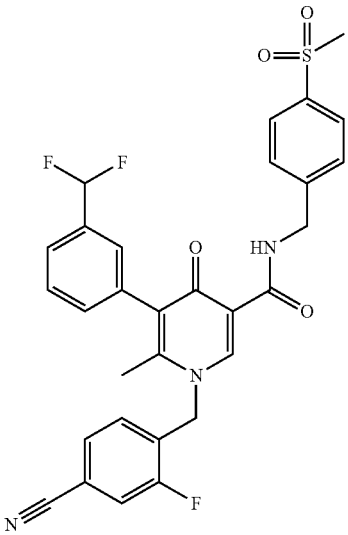

Example 41 is prepared as described for example 2.1, substituting benzyl bromide with 4-bromomethyl-3-fluorobenzonitrile and substituting preparation 5 with preparation 39a. ESI mass spectrum: $[M+H]^+$=580; Retention time HPLC: 1.02 min (Z018_S04).

Example 42

1-(4-Cyano-2-fluoro-benzyl)-2-methyl-4-oxo-2'-trifluoromethyl-1,4-dihydro-[3,4']bipyridinyl-5-carboxylic acid methylamide

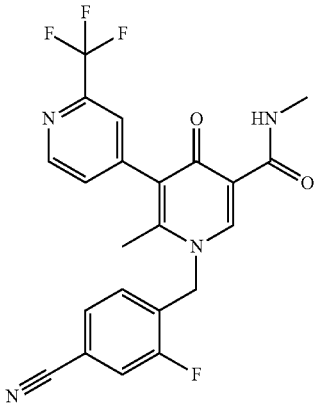

Example 42 is prepared as described for example 2.1, substituting benzyl bromide with 4-s bromomethyl-3-fluorobenzonitrile and substituting preparation 5 with preparation 36a. ESI mass spectrum: $[M+H]^+$=445; Retention time HPLC: 0.96 min (Z018_S04).

Example 43

1-(4-Cyano-3-fluoro-benzyl)-2-methyl-4-oxo-2'-trifluoromethyl-1,4-dihydro-[3,4']bipyridinyl-5-carboxylic acid methylamide

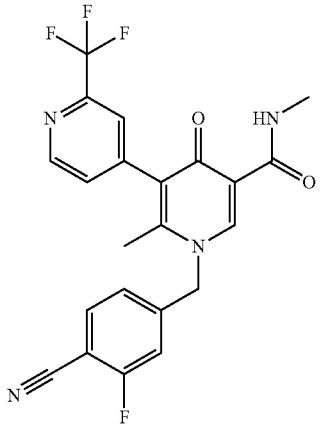

Example 43 is prepared as described for example 2.1, substituting benzyl bromide with 4-bromomethyl-2-fluorobenzonitrile and substituting preparation 5 with preparation 36a. ESI mass spectrum: $[M+H]^+$=445; Retention time HPLC: 0.97 min (Z018_S04).

Example 44

1-(5-Cyano-pyridin-2-ylmethyl)-2-methyl-4-oxo-2'-trifluoromethyl-1,4-dihydro-[3,4']bipyridinyl-5-carboxylic acid methylamide

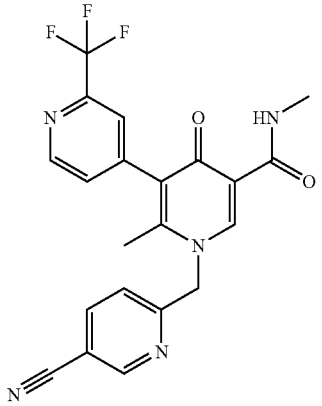

Example 44 is prepared as described for example 2.1, substituting benzyl bromide with 6-bromomethyl-nicotinonitrile and substituting preparation 5 with preparation 36a. ESI mass spectrum: $[M+H]^+$=428; Retention time HPLC: 0.99 min (Z018_S04).

Example 45

1-[1-(4-Cyano-phenyl)-cyclopropyl]-6-methyl-4-oxo-5-(3-trifluoromethyl-phenyl)-1,4-dihydro-pyridine-3-carboxylic acid 4-methanesulfonyl-benzyl-amide

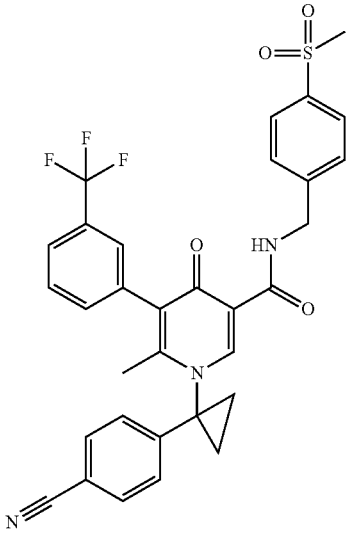

45a 1-[1-(4-Cyano-phenyl)-cyclopropyl]-6-methyl-4-oxo-1,4-dihydro-pyridine-3-carboxylic acid

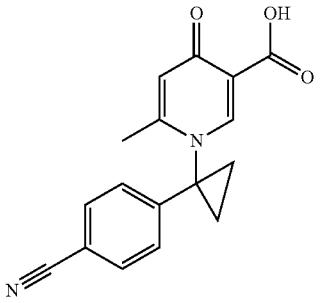

Preparation 45a is prepared as described for preparation 1b, substituting 4-cyanobenzylamine hydrochloride with 4-(1-aminocyclopropyl)-benzonitril hydrochloride. ESI mass spectrum: $[M+H]^+$=295; Retention time HPLC: 0.95 min (Z002_005).

45b 1-[1-(4-Cyano-phenyl)-cyclopropyl]-6-methyl-4-oxo-1,4-dihydro-pyridine-3-carboxylic acid 4-methanesulfonyl-benzylamide

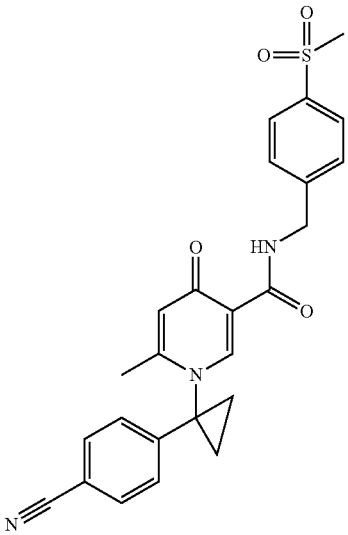

Preparation 45b is prepared as described for Example 9, substituting preparation 2b with preparation 45a and methylamine with 4-(methylsulfonyl)benzylamine. ESI mass spectrum: $[M+H]^+$=462; Retention time HPLC: 0.89 min (Z018_S04).

45c 5-Bromo-1-[1-(4-cyano-phenyl)-cyclopropyl]-6-methyl-4-oxo-1,4-dihydro-pyridine-3-carboxylic acid 4-methanesulfonyl-benzylamide

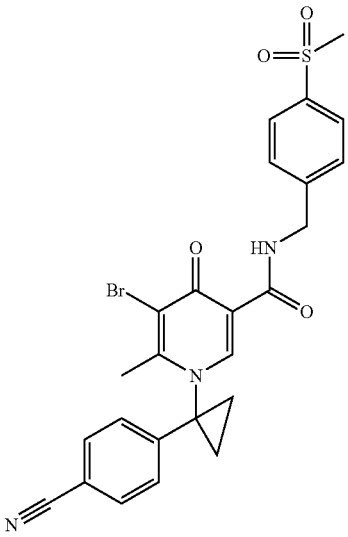

Preparation 45c is prepared by bromination of preparation 45b with N-bromosuccinimide in dichloromethane (1 h, room temperature) and subsequent purification by reversed-phase HPLC (Sunfire, gradient of methanol in water, 0.1% TFA, 60° C.). ESI mass spectrum: $[M+H]^+$=540 (bromine pattern); Retention time HPLC: 0.96 min (Z018_S04).

Example 45

1-[1-(4-Cyano-phenyl)-cyclopropyl]-6-methyl-4-oxo-5-(3-trifluoromethyl-phenyl)-1,4-dihydro-pyridine-3-carboxylic acid 4-methanesulfonyl-benzyl-amide

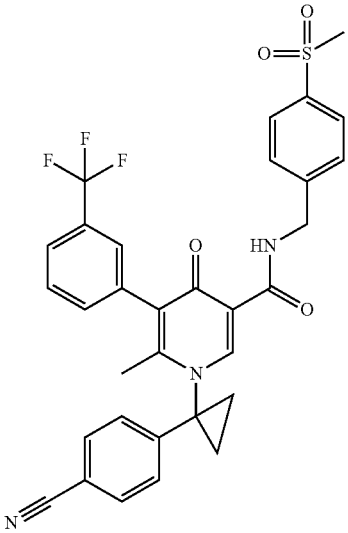

Example 45 is prepared as described for example 6.1, substituting phenylboronic acid with 3-(trifluoromethyl) phenylboronic acid. ESI mass spectrum: $[M+H]^+$=606; Retention time HPLC: 1.09 min (Z018_S04).

Example 46

1-(4-Cyano-benzyl)-6-methyl-4-oxo-5-(3-trifluoromethyl-phenyl)-1,4-dihydro-pyridine-3-carboxylic acid cyanomethyl-amide

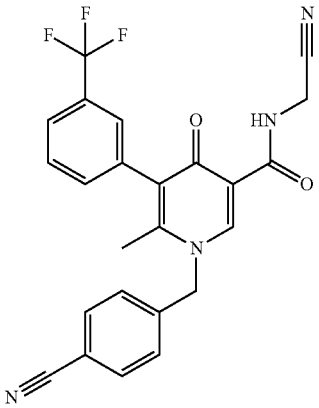

To a solution of 1-(4-cyano-benzyl)-6-methyl-4-oxo-5-(3-trifluoromethyl-phenyl)-1,4-dihydro-pyridine-3-carboxylic acid (preparation 1, 60 mg, 90% purity, 0.131 mmol), aminoacetonitrile (15 mg, 0.262 mmol) and N-methylmorpholine (66 mg, 0.66 mmol) in dichloromethane (2 mL) is added at 0° C. 1-propanephosphonic acid cyclic anhydride in ethyl acetate (250 mg, 50%, 0.39 mmol). The reaction mixture is stirred for 3 h at room temperature. The volatiles are evaporated under reduced pressure and the remaining residue is purified by preparative reversed-phase HPLC (Sunfire, gradient of acetonitrile in water, 0.1% TFA, 60° C.). Yield: 5 mg (9% of theory); ESI mass spectrum: $[M+H]^+$=451; Retention time HPLC: 0.87 min (Z011_S03).

Examples 47.1-47.20 are prepared in two steps: (1) Amide coupling as described for preparation 9.13 (Procedure A), substituting preparation 4 with preparation 5b and substituting aminoacetonitrile with the appropriate amines, respectively; (2) Alkylation as described for example 2.1, substituting benzyl bromide with preparation 15c, substituting preparation 5 with the intermediates from step 1, and substituting DMF with NMP.

Intermediates from Step 1 (Amide Coupling)

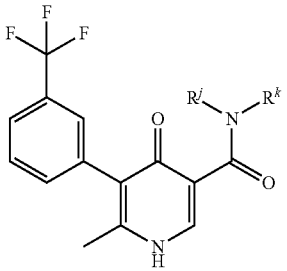

| Intermediate for Example . . . | $R^jR^kN$— | MS $[M + H]^+$ | Retention time HPLC/ Method |
|---|---|---|---|
| 47.1 | 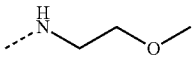 | 355 | 0.68 min Z011_S03 |
| 47.2 | 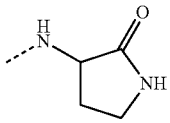 | 380 | 0.61 min Z011_S03 |
| 47.3 | 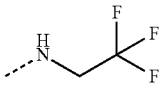 | 379 | 1.01 min Z018_S043 |
| 47.4 | 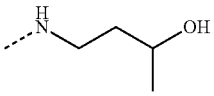 | 369 | 0.88 min Z012_S04 |
| 47.5 | 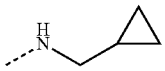 | 351 | 0.75 min Z011_S03 |
| 47.6 | 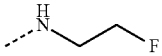 | 343 | 0.66 min Z011_S03 |
| 47.7 | 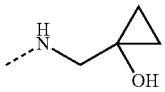 | 367 | 0.64 min Z011_S03 |
| 47.8 | 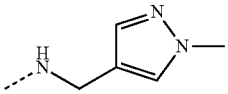 | 391 | 0.66 min Z011_S03 |

-continued

| Intermediate for Example . . . | $R^jR^kN$— | MS $[M + H]^+$ | Retention time HPLC/ Method |
|---|---|---|---|
| 47.9 | 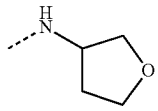 | 367 | 0.65 min Z011_S03 |
| 47.10 | 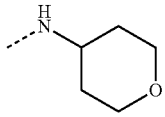 | 381 | 0.67 min Z011_S03 |
| 47.11 | 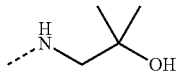 | 369 | 0.65 min Z011_S03 |
| 47.12 | 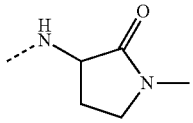 | 394 | 0.63 min Z011_S03 |
| 47.13 | 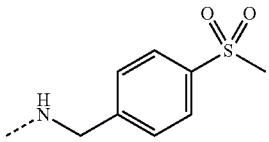 | 465 | 0.71 min Z011_S03 |
| 47.14 | 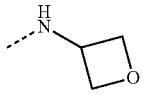 | 353 | 0.65 min Z011_S03 |
| 47.15 | 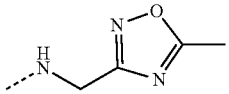 | 393 | 0.69 min Z011_S03 |
| 47.16 | 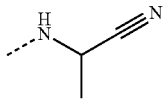 | 350 | 0.66 min Z011_S03 |
| 47.17 | 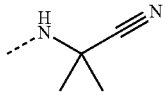 | 364 | 0.68 min Z011_S03 |
| 47.18 | 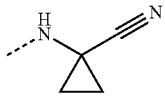 | 362 | 0.65 min Z011_S03 |
| 47.19 | 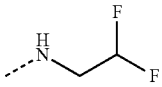 | 361 | 0.96 min Z018_S04 |
| 47.20 | 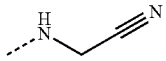 | 336 | 0.92 min Z018_S04 |

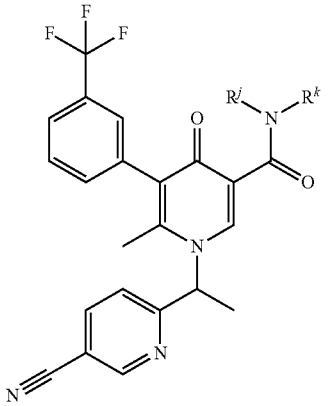

| Example | $R^jR^kN$— | MS $[M + H]^+$ | Retention time HPLC/Method |
|---|---|---|---|
| 47.1 | 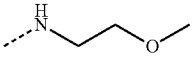 | 485 | 1.02 min Z018_S04 |
| 47.2 | 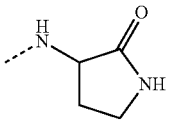 | 510 | 0.94 min Z018_S04 |
| 47.3 | 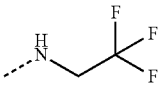 | 509 | 1.10 min Z018_S04 |
| 47.4 | 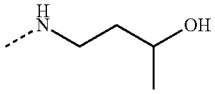 | 499 | 0.99 min Z018_S04 |
| 47.5 | 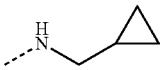 | 481 | 1.09 min Z018_S04 |
| 47.6 | 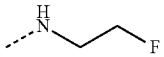 | 473 | 1.01 min Z017_S04 |
| 47.7 | 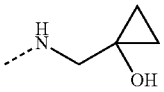 | 497 | 1.00 min Z018_S04 |
| 47.8 | 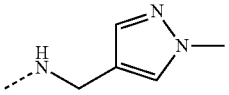 | 521 | 0.99 min Z018_S04 |
| 47.9 | 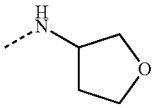 | 497 | 0.99 min Z017_S04 |
| 47.10 | 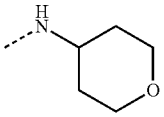 | 511 | 1.02 min Z018_S04 |

-continued

| Example | $R^jR^kN$— | MS $[M + H]^+$ | Retention time HPLC/Method |
|---|---|---|---|
| 47.11 | 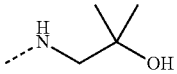 | 499 | 0.99 min Z018_S04 |
| 47.12 | 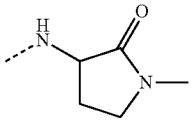 | 524 | 0.97 min Z018_S04 |
| 47.13 | 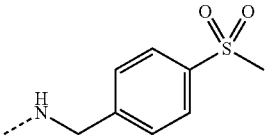 | 595 | 1.04 min Z018_S04 |
| 47.14 | 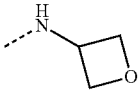 | 483 | 0.99 min Z018_S04 |
| 47.15 | 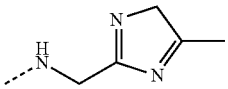 | 523 | 1.03 min Z018_S04 |
| 47.16 | 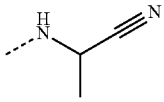 | 480 | 1.06 min Z018_S04 |
| 47.17 | 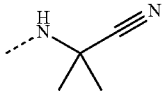 | 494 | 1.08 min Z018_S04 |
| 47.18 | 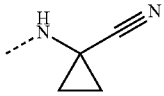 | 492 | 1.05 min Z018_S04 |
| 47.19 | 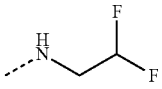 | 491 | 1.06 min Z018_S04 |
| 47.20 | 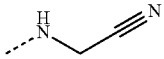 | 466 | 1.01 min Z018_S04 |

EXAMPLES

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: I-1270). All other materials were of the highest grade commercially available.

The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 μL of these compound dilutions were mixed with 10 μl Neutrophil elastase (9 ng/ml in assay buffer) in a black 384 well OptiPlate (Perkin Elmer, Cat No.: 6007270) and incubated for 15 min at room temperature. Subsequently 10 μL substrate solution in assay buffer were added (250 μM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). 1050 values were estimated using a sigmoidal concentration response curve with variable slope. Means of low values were taken as 0%, means of high values as 100%. 1050 values of selected compound in the Neutrophil Elastase assay:

| Example | IC50 [nM] |
|---|---|
| 1.1 | 15.2 |
| 1.2 | 48.3 |
| 1.3 | 13.0 |
| 1.4 | 27.6 |
| 1.5 | 10.4 |
| 1.6 | 30.5 |
| 1.7 | 15.8 |
| 1.8 | 83.0 |
| 1.9 | 8.4 |
| 1.10 | 1.1 |
| 1.11 | 14.4 |
| 1.12 | 12.1 |
| 1.13 | 6.6 |
| 1.14 | 1.8 |
| 1.15 | 7.9 |
| 1.16 | 7.4 |
| 1.17 | 21.0 |
| 1.18 | 23.8 |
| 1.19 | 48.1 |
| 1.20 | 10.6 |
| 1.21 | 14.4 |
| 1.22 | 44.6 |
| 1.23 | 19.0 |
| 1.24 | 10.0 |
| 1.25 | 10.9 |
| 1.26 | 13.2 |
| 1.27 | 46.4 |
| 1.28 | 21.8 |
| 1.29 | 31.6 |
| 1.30 | 17.1 |
| 1.31 | 13.7 |
| 1.32 | 23.0 |
| 1.33 | 3.7 |
| 1.34 | 8.9 |
| 1.35 | 31.4 |
| 1.36 | 47.1 |
| 1.37 | 95.7 |
| 1.38 | 36.9 |
| 1.39 | 6.2 |
| 1.40 | 2.1 |
| 1.41 | 3.2 |
| 1.42 | 5.2 |
| 1.43 | 8.9 |
| 1.44 | 7.9 |
| 1.45 | 7.6 |
| 1.46 | 5.9 |
| 1.47 | 22.0 |
| 1.48 | 4.1 |
| 1.49 | 10.4 |
| 1.50 | 1.4 |
| 1.51 | 10.7 |
| 1.52 | 9.6 |
| 1.53 | 9.0 |
| 1.54 | 41.5 |
| 1.55 | 4.9 |
| 1.56 | 4.6 |
| 1.57 | 6.8 |
| 1.58 | 8.1 |

-continued

| Example | IC50 [nM] |
|---|---|
| 1.59 | 10.5 |
| 1.60 | 13.3 |
| 1.61 | 11.4 |
| 1.62 | 10.4 |
| 1.63 | 22.5 |
| 1.64 | 17.2 |
| 1.65 | 38.5 |
| 1.66 | 6.2 |
| 1.67 | 6.5 |
| 2.1 | 55.3 |
| 2.2 | 1.9 |
| 2.3 | <1 |
| 2.4 | 1.4 |
| 2.5 | <1 |
| 2.6 | 1.6 |
| 2.7 | 6.9 |
| 2.8 | <1 |
| 2.9 | <1 |
| 2.10 | 83.8 |
| 2.11 | 38.9 |
| 2.12 | <1 |
| 2.5A | <1 |
| 2.5B | 20.1 |
| 3.1 | 2.9 |
| 3.2 | 53.7 |
| 3.3 | 51.0 |
| 3.4 | 29.1 |
| 3.5 | 19.3 |
| 3.6 | 20.3 |
| 3.7 | 26.4 |
| 3.8 | 14.0 |
| 3.9 | 25.7 |
| 3.1A | <1 |
| 3.1B | 225.5 |
| 4.1 | <1 |
| 4.2 | 2.1 |
| 4.3 | 58.0 |
| 4.4 | 63.8 |
| 4.5 | 1.0 |
| 4.6 | 1.5 |
| 4.7 | <1 |
| 4.8 | 1.4 |
| 4.9 | <1 |
| 4.10 | <1 |
| 5.1 | 2.8 |
| 5.2 | 1.2 |
| 5.3 | 1.4 |
| 6.1 | 44.5 |
| 6.2 | 1.5 |
| 6.3 | 9.1 |
| 6.4 | 19.3 |
| 6.5 | 9.6 |
| 6.6 | 38.6 |
| 6.7 | 75.3 |
| 6.8 | <1 |
| 6.9 | 3.8 |
| 6.10 | <1 |
| 6.11 | <1 |
| 6.12 | 3.8 |
| 6.13 | 2.5 |
| 7.1 | 4.1 |
| 7.2 | 2.5 |
| 7.3 | 1.3 |
| 7.4 | 1.8 |
| 7.5 | 1.4 |
| 7.6 | 1.2 |
| 7.7 | 2.4 |
| 7.8 | 1.3 |
| 7.9 | 2.3 |
| 7.10 | 2.0 |
| 7.11 | 4.4 |
| 7.12 | 1.5 |
| 7.13 | 4.0 |
| 7.14 | 4.7 |
| 7.15 | 10.3 |
| 7.16 | 17.9 |
| 7.17 | 18.5 |

-continued

| Example | IC50 [nM] |
|---|---|
| 7.18 | <1 |
| 7.19 | 4.1 |
| 7.20 | 3.6 |
| 8A | 1.2 |
| 8B | 522.0 |
| 8.1 | 4.1 |
| 8.2 | 1.9 |
| 8.3 | 1.3 |
| 8.4 | 1.8 |
| 8.5 | 1.2 |
| 8.6 | 1.2 |
| 8.7 | 1.7 |
| 8.8 | 1.1 |
| 8.9 | 1.9 |
| 8.10 | 1.6 |
| 8.11 | 4.3 |
| 8.12 | 1.4 |
| 8.13 | 3.2 |
| 8.14 | 3.6 |
| 8.15 | 4.4 |
| 8.16 | 2.4 |
| 8.17 | 3.1 |
| 8.18 | 2.4 |
| 8.19 | 1.7 |
| 8.20 | 1.0 |
| 8.21 | 3.0 |
| 8.22 | 21.6 |
| 8.23 | 3.4 |
| 8.24 | 1.7 |
| 8.25 | 1.8 |
| 8.26 | 1.8 |
| 8.27 | 3.0 |
| 8.28 | 3.3 |
| 9A | 3.7 |
| 9B | 1505.0 |
| 9.1 | 4.5 |
| 9.2 | 3.3 |
| 9.3 | 3.9 |
| 9.4 | 4.1 |
| 9.5 | 5.7 |
| 9.5A | 2.8 |
| 9.5B | 878.5 |
| 9.6 | 3.2 |
| 9.7 | 7.0 |
| 9.8 | 4.2 |
| 9.9 | 7.6 |
| 9.10 | 12.4 |
| 9.11 | 18.3 |
| 9.12 | 4.6 |
| 9.13 | 1.7 |
| 9.14 | 7.0 |
| 9.15 | 5.7 |
| 9.16 | 6.7 |
| 9.17 | 10.1 |
| 9.18 | 7.5 |
| 9.19 | 8.9 |
| 9.20 | 10.9 |
| 9.21 | 9.5 |
| 9.22 | 7.3 |
| 9.23 | 14.4 |
| 9.24 | 9.8 |
| 9.25 | 11.4 |
| 9.26 | 12.1 |
| 9.27 | 13.7 |
| 9.28 | 12.8 |
| 9.29 | 22.3 |
| 9.30 | 16.3 |
| 9.31 | 18.7 |
| 9.32 | 19.4 |
| 9.33 | 23.1 |
| 9.34 | 23.5 |
| 9.35 | 26.2 |
| 9.36 | 33.9 |
| 9.37 | 32.9 |
| 9.38 | 33.3 |
| 9.39 | 58.3 |
| 9.40 | 69.4 |

-continued

| Example | IC50 [nM] |
|---|---|
| 9.41 | 100.0 |
| 9.42 | 29.9 |
| 9.43 | 11.5 |
| 9.44 | 9.8 |
| 9.45 | 5.3 |
| 9.46 | 94 |
| 9.47 | 14.9 |
| 9.48 | 17.3 |
| 9.49 | 150 |
| 9.50 | 4.6 |
| 9.51 | 6.0 |
| 9.52 | 420 |
| 9.53 | 23 |
| 9.54 | 4.1 |
| 9.55 | 5.1 |
| 9.56 | 6.1 |
| 9.56A | 2.3 |
| 9.56B | 1299.3 |
| 9.57 | 5.2 |
| 9.58 | 5.4 |
| 9.59 | 7.5 |
| 9.60 | 5.7 |
| 9.61 | 8.6 |
| 9.62 | 12.0 |
| 9.63 | 37.5 |
| 10A | <1 |
| 10B | 289.5 |
| 11A | <1 |
| 11B | 19.5 |
| 12.1 | 35.9 |
| 12.2 | 49.5 |
| 12.3 | 59.7 |
| 12.4 | 14.4 |
| 13.1 | 6.6 |
| 13.2 | 5.2 |
| 14 | <1 |
| 15 | 10.5 |
| 15A | 3.8 |
| 15B | 67.8 |
| 16 | 9.9 |
| 16A | 4.2 |
| 16B | 371.5 |
| 17 | 4.5 |
| 18 | 5.4 |
| 19 | 22.2 |
| 20 | 8.6 |
| 21 | 4.6 |
| 22 | 2.8 |
| 23 | 4.4 |
| 24 | 4.8 |
| 25 | 14.0 |
| 26 | 10.8 |
| 27 | 8.1 |
| 28 | 13.3 |
| 29 | 14.4 |
| 30 | 5.3 |
| 31 | 7.8 |
| 31A | 1885.0 |
| 31B | 4.2 |
| 32 | 11.8 |
| 33 | 14.0 |
| 34 | 31.2 |
| 35 | 7.8 |
| 36 | 18.4 |
| 37 | 13.7 |
| 38 | 11.0 |
| 39 | <1 |
| 40 | <1 |
| 41 | <1 |
| 42 | 46.0 |
| 43 | 48.4 |
| 44 | 94.6 |
| 45 | 4.6 |
| 46 | 2.3 |
| 47.1 | 12.9 |
| 47.2 | 7.3 |
| 47.3 | 10.7 |

-continued

| Example | IC50 [nM] |
|---|---|
| 47.4 | 12.2 |
| 47.5 | 16.7 |
| 47.6 | 12.0 |
| 47.7 | 30.1 |
| 47.8 | 13.1 |
| 47.9 | 67.2 |
| 47.10 | 19.2 |
| 47.11 | 63.5 |
| 47.12 | 7.3 |
| 47.13 | <1 |
| 47.14 | 26.4 |
| 47.15 | 13.4 |
| 47.16 | 6.2 |
| 47.17 | 139 |
| 47.18 | 6.4 |
| 47.19 | 10.3 |
| 47.20 | 2.5 |

Surprisingly, it was found that for compounds with a single methyl group attached to the methylene group connecting the 4-pyridone nitrogen with the 4-cyano-phenyl or 4-cyano-pyridyl moiety, typically there is a strong discrimination in neutrophil elastase inhibitory potency observed for the two enantiomers.

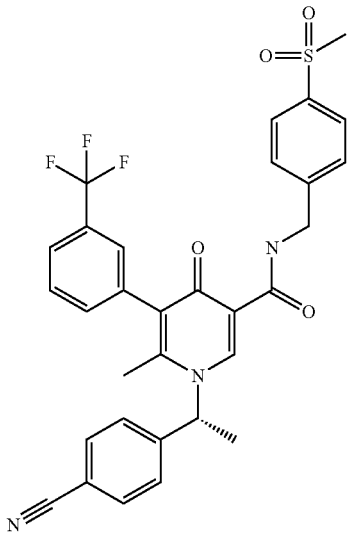

For instance, in the case of example 2.5, the enantiomer example 2.5A (eutomer) is much more active than enantiomer example 2.5B (distomer); wherein the absolute configuration of compound 2.5A can be determined to be (R) by x-ray analysis.

Similar observations were made for the following examples: example 3.1, example 8, example 9, example 10, example 11, example 9.5, example 9.56, example 15, example 16, example 31, thus from the above mentioned examples the more active enantiomers (eutomers) are preferred; furthermore based on the x-ray analysis of eutomers the (R) configuration is preferred for the benzylic carbon atom.

Combinations

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors Non-steroidale anti-inflammatory agents (NSAIDs), Cathepsin C (or DPPI/Dipeptidyl-aminopeptidase I) inhibitors, CRTH2 antagonists, DP1-receptor modulators, Thromboxane receptor antagonists, CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, CXCR3 antagonists, CXCR4 antagonists, CXCR2 antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, i.e.:

- Betamimetics with corticosteroids, PDE4-inhibitors, CRTH2-inhibitors or LTD4-antagonists,
- Anticholinergics with betamimetics, corticosteroids, PDE4-inhibitors, CRTH2-inhibitors or LTD4-antagonists,
- Corticosteroids with PDE4-inhibitors, CRTH2-inhibitors or LTD4-antagonists
- PDE4-inhibitors with CRTH2-inhibitors or LTD4-antagonists
- CRTH2-inhibitors with LTD4-antagonists.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury (ALI); acute respiratory distress syndrome (ARDS).

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, Candida, aspergillus, cryptococcal meningitis, Pneumocystis carnii, cryptosporidiosis, histoplasmosis, toxoplasmosis, trypanosome infection and leishmaniasis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:

[1. A compound of formula 1

1

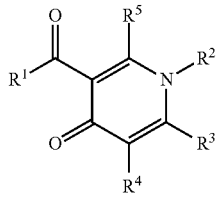

wherein $R^1$ is $H_2N$—, $R^{1.1}HN$—, $R^{1.2}HN$—, $H(O(CH_2)_2)_2$—HN—, $H(O(CH_2)_2)_3$—HN—, or $H(O(CH_2)_2)_4HN$—;

$R^{1.1}$ is $C_{3-6}$-cycloalkly or a four-, five- or six-membered, non-aromatic heteroring, wherein one, two or three elements are replaced by an element selected independent from each other from the group consisting of N, O, S, (O)S and $(O)_2S$;

wherein each element of one of the above mentioned rings is optionally substituted with a residue selected from the group consisting of HO—, O═, $C_{1-4}$-alkyl-, $C_{1-4}$-cycloalkyl-, $C_{1-4}$-haloalkyl-, halogen, NC—; and if the rings contains nitrogen, it is optionally substituted with $C_{1-4}$-alkyl-, $C_{3-6}$- cycloalkyl-, $C_{1-4}$-haloalkyl-, $C_{1-4}$-alkyl-(O)C—, $C_{1-4}$-haloalkyl-(O)C—, $C_{3-6}$-cycloalkyl-(O)C—, $C_{1-4}$-alkyl-O(O)C—, $C_{1-4}$-alkyl-HN(O)C—, $(C_{1-4}\text{-alkyl})_2N(O)C$—, $C_{1-4}$-alkyl-$(O)_2S$—;

$R^{1.2}$ is a branched or unbranched $C_{1-6}$-alkyl-, $C_{2-6}$-alkenyl or $C_{2-6}$-alkynyl, optionally substituted independently from each other with one, two or three residues selected from the group consisting of HO—, O═, HO—, halogen, NC—, $C_{1-4}$-alkyl-O—, $H_2N$—, ($C_{1-4}$-alkyl)-HN—, $(C_{1-4}\text{-alkyl})_2N$—, $C_{1-4}$-alkyl-O(O)C—, HO(O)C—, $H_2N$—(O)C—, ($C_{1-4}$-alkyl)-HN—(O)C—, $(C_{1-4}\text{-alkyl})_2N(O)C$—, ($C_{1-4}$-alkyl)-(O)C—HN—, ($C_{1-4}$-alkyl)-(O)C—($C_{1-4}$-alkyl)N—, ($C_{1-4}$-alkyl)-O(O)C—HN—, ($C_{1-4}$-alkyl)-O(O)C—($C_{1-4}$-alkyl)N—, $H_2N$—(O) C—NH—, ($C_{1-4}$-alkyl)-NH—(O)C—NH—, $(C_{1-4}\text{-alkyl})_2N$—(O)C—HN—, $H_2N$—(O) C—($C_{is}$-alkyl)N—, ($C_{1-4}$-alkyl)-HN—(O)C—($C_{1-4}$-alkyl)N—, $(C_{1-4}\text{-alkyl})_2N$—(O)C—($C_{1-4}$-alkyl) N—, $C_{1-4}$-alkyl-(O)S—, $C_{1-4}$-alkyl-$(O)_2S$—, $C_{1-4}$-alkyl-(HN)(O)S—, $C_{1-4}$-alkyl-($C_{1-4}$-alkyl-N)(O) S—, $C_{1-4}$ alkyl (NC—N)(O) S—, $C_{1-4}$-alkyl-$(O)_2S$—HN—, $C_{1-4}$-alkyl-$(O)_2S$—($C_{1-4}$-alkyl) N—;

Azetidinyl-(O)C—, Pyrrolidinyl-(O)C—, Piperidinyl-(O)C—, Morpholinyl-(O)C—;

Azetidinyl-(O)C—HN—, Pyrrolidinyl-(O)C—HN—, Piperidinyl-(O)C—HN—, Morpholinyl-(O)C—HN—;

Azetidinyl-(O)C—($C_{1-4}$-alkyl)N—, Pyrrolidinyl-(O)C—($C_{1-4}$-alkyl)N—, Piperidinyl-(O)C—($C_{1-4}$-alkyl)N—, Morpholinyl-(O)C—($C_{1-4}$-alkyl)N—;

a ring selected from $C_{1-6}$-cycloalkly, phenyl, a five- or six-membered, aromatic or non-aromatic heteroring, wherein one, two or three elements of the ring are replaced by an element selected independent from each other from the group consisting of N, $(O^-)$—$N^+$, O, S, (O)S and $(O)_2S$; or a ring system of two fused aromatic or non-aromatic heterorings, wherein one or two elements of the rings are replaced by an element selected independent from each other from the group consisting of N, O, S, (O)S and $(O)_2S$; wherein each element of one of the above mentioned rings and fused rings is optionally substituted with a residue selected from the group consisting of O═, $C_{1-4}$-alkyl-, $C_{1-4}$-alkyl-(O)C—, $C_{1-4}$-alkyl-O(O)C—, $C_{1-4}$-haloalkyl-, $C_{3-6}$cycloalkyl-, HO—, $C_{1-4}$-alkyl-O—, NC—, halogen, $C_{1-4}$alkyl-S—, $C_{1-4}$-alkyl-(O)S—, $C_{1-4}$-alkyl-$(O)_2S$—, $Me_2N$—$CH_2$—(O)C—;

$R^2$ is $R^{2.1}R^{2.2}R^{2.3}C$—;

$R^{2.1}$ is phenyl or a five- or six-membered, aromatic heteroring, wherein one, two or three elements are replaced by an element selected independent from each other from the group consisting of N, O and S; wherein each element of one of the above mentioned rings is optionally substituted with a residue selected from the group consisting of O═, $C_{1-4}$-alkyl-, $C_{3-6}$-cycloalkyl-, $C_{1-4}$-haloalkyl-, halogen, NC—, $C_{1-4}$-alkyl-O—, $C_{1-4}$-alkyl-$(O)_2S$—, $C_{3-6}$cycloalkyl-$(O)_2S$—, $C_{1-4}$-alkyl-(HN)(O)S—, $C_{1-4}$-alkyl-($C_{1-4}$-alkyl-N)(O)S—, $C_{1-4}$-alkyl-(NC—N)(O)S—;

$R^{2.2}$ is H or $C_{1-4}$-alkyl-;

$R^{2.3}$ is H, $C_{1-4}$-alkyl-, $C_{1-4}$-haloalkyl or $C_{3-6}$-cycloalkyl-;

or $R^{2.2}$ and $R^{2.3}$ are forming together a $C_{2-5}$-alkylene;

or $R^{2.1}$ is phenyl, optionally substituted with NC—, and $R^{2.2}$ is $C_{2-3}$-alkylene forming together with the ortho position of the phenyl ring a fused ring system, wherein optionally one element is replaced by an element selected independent from each other from the group consisting of 0 and $(O)_2S$;

$R^3$ is of $C_{1-4}$-alkyl-;

$R^4$ is phenyl or a five- or six-membered, aromatic heteroring, wherein one or two elements are replaced by an element selected independent from each other from the group consisting of N, O and S; wherein each element of one of the above mentioned rings is optionally substituted with a residue selected from the group consisting of O═, $C_{1-4}$-alkyl-, $C_{1-4}$-alkyl-O—, $C_{1-4}$-haloalkyl-, halogen;

$R^5$ is selected from the group consisting of H, $C_{1-4}$-alkyl-, $C_{1-4}$-haloalkyl- or halogen;

or a salt thereof.]

[2. A compound of formula 1, according to claim 1, wherein $R^1$ is $H_2N$—, $R^{1.1}HN$—, $R^{1.2}HN$—, $H(O(CH_2)_2)_3$—HN—;

$R^{1.1}$ is $C_{3-6}$-cycloalkly or a four-, five- or six-membered, non-aromatic heteroring, wherein one or two elements are replaced by an element selected independent from each other from the group consisting of N, O, S, (O)S and $(O)_2S$; wherein each element of one of the above mentioned rings is optionally substituted with a residue selected from the group consisting of HO—, O═, $C_{1-4}$-alkyl-, $C_{1-4}$-cycloalkyl-, NC—;

$R^{1.2}$ is a branched or unbranched $C_{1-4}$-alkyl-, optionally substituted independently from each other with one, two or three residues selected from the group consisting of —HO—, F, NC—, $C_{1-4}$-alkyl-O—, $(C_{1-4}\text{-alkyl})_2$-N—, $C_{1-4}$-alkyl-O(O)C—, HO(O)C—, $(C_{1-4}\text{-alkyl})_2$-N(O)C—, ($C_{1-4}$-alkyl)-(O)S—, ($C_{1-4}$-alkyl)-$(O)_2S$—;

a ring selected from $C_{3-6}$-cycloalkly, phenyl, a five- or six-membered, aromatic or non-aromatic heteroring, wherein one, two or three elements are replaced by an element selected independent from each other from the group consisting of N, $(O^-)$—$N^+$ and O; wherein each element of one of the above mentioned rings is optionally substituted with a residue selected from the group consisting of O═, halogen, $C_{1-4}$-alkyl-, $C_{1-4}$-haloalkyl-, $C_{3-6}$-cycloalkyl-, HO—, $C_{1-4}$-alkyl-O—, NC—, $C_{1-4}$-alkyl-S—, $C_{1-4}$-alkyl-(O)S—, $C_{1-4}$-alkyl-$(O)_2S$—, $Me_2N$—$CH_2$—(O)C—;

$R^2$ is $R^{2.1}R^{2.2}R^{2.3}C$—;

$R^{2.1}$ is phenyl or a five- or six-membered, aromatic heteroring, wherein one or two elements are replaced by an element selected independent from each other from the group consisting of N, O and S; wherein one or two elements of one of the above mentioned rings are optionally substituted with a residue selected from the group consisting of halogen, NC—, $C_{1-4}$-alkyl-, $C_{1-4}$-haloalkyl-, $C_{1-4}$-alkyl-O—, $C_{1-4}$-alkyl-$(O)_2S$—, $C_{3-6}$cycloalkyl-$(O)_2S$—;

$R^{2.2}$ is H or $C_{1-4}$-alkyl-;

$R^{2.3}$ is H or $C_{1-4}$-alkyl-;

$R^3$ is $C_{1-4}$-alkyl-;

$R^4$ is phenyl or a six-membered, aromatic heteroring, wherein one or two elements are replaced by N; wherein one or two elements of one of the above mentioned rings are substituted with a residue selected from the group consisting of $C_{1-4}$-alkyl-, $C_{1-4}$-haloalkyl-, halogen;

$R^5$ is H;

or a salt thereof.]

[3. A compound of formula 1, according to claim 1, wherein $R^1$ is $H_2N$ , $R^{1.1}HN$—, $R^{1.2}HN$—, $H(O(CH_2)_2)_3$—HN—;

$R^{1.1}$ is cyclopropyl, cyclohexyl, oxetanyl, tetrahydrofuranyl, tetrahydropyranyl, pyrrolidin-2-onyl, piperidin-2-onyl, tetrahydrothiophen-1,1-dioxidyl, each optionally substituted with methyl, HO— or NC—;

$R^{1.2}$ is a branched or unbranched $C_{1-4}$-alkyl-, optionally substituted independently from each other with one, two or three residues selected from the group consisting of HO—, F, NC—, $C_{1-4}$-alkyl-O—, $(C_{1-4}\text{-alkyl})_2$-N—, $C_{1-4}$-alkyl-O(O)C—, HO(O)C—, $(C_{1-4}\text{-alkyl})_2$-N(O)C—, $C_{1-4}$-alkyl-(O)S—, $C_{1-4}$-alkyl-$(O)_2S$—;

a ring selected from $C_{3-6}$-cycloalkly, phenyl, a five- or six-membered, aromatic or non-aromatic heteroring, wherein one, two or three elements are replaced by an element selected independent from each other from the group consisting of N, $(O^-)$—$N^+$ and O; wherein each element of one of the above mentioned rings is optionally substituted with a residue selected from the group consisting of O═, halogen, $C_{1-4}$-alkyl-, $C_{1-4}$-haloalkyl-, $C_{3-6}$-cycloalkyl-, HO—, $C_{1-4}$-alkyl-O—, NC—, $C_{1-4}$-alkyl-S—, $C_{1-4}$-alkyl-(O)S—, $C_{1-4}$-alkyl-$(O)_2S$—, $Me_2N$—$CH_2$—(O)C—;

$R^2$ is $R^{2.1}R^{2.2}R^{2.3}C$—;

$R^{2.1}$ is phenyl, a five- or six-membered, aromatic heteroring, wherein one or two elements are replaced by an element selected independent from each other from the group consisting of N, O and S; wherein one or two elements of one of the above mentioned rings are substituted with a residue selected from the group consisting of halogen, NC—, $C_{1-4}$-alkyl-, $C_{1-4}$-haloalkyl-, $C_{1-4}$-alkyl-(O)—, $C_{1-4}$-alkyl-$(O)_2S$—, $C_{3-6}$-cycloalkyl-$(O)_2S$—;

$R^{2.2}$ is H or $C_{1-4}$-alkyl-;

$R^{2.3}$ is H or $C_{1-4}$-alkyl-;

$R^3$ is $C_{1-4}$-alkyl-;

$R^4$ is phenyl or pyridinyl, substituted with $C_{1-4}$-haloalkyl-;

$R^5$ is H;

or a salt thereof.]

[4. A compound of formula 1, according to claim 1, wherein $R^1$ is $H_2N$—, $R^{1.1}HN$—, $R^{1.2}HN$—, $H(O(CH_2)_2)_3$—HN—;

$R^{1.1}$ is cyclopropyl, cyclohexyl, oxetanyl, tetrahydrofuranyl, tetrahydropyranyl, pyrrolidin-2-onyl, piperidin-2-onyl, tetrahydrothiophen-1,1-dioxidyl, each optionally substituted with methyl, HO— or NC—;

$R^{1.2}$ is a branched or unbranched $C_{1-4}$-alkyl-, optionally substituted independently from each other with one or two residues selected from the group consisting of HO—, MeO—, EtO—, $Me_2N$—, MeO(O)C—, $Me_2N$(O)C—, Me(O)S—, $Me(O)_2S$—;

oxetanyl, tetrahydropyranyl, tetrahydrofuranyl, dioxanyl, morpholinyl, imidazolidin-2-onyl, pyrrolidin-2-onyl, pyridin-2-onyl;

azetidinyl, pyrrolidinyl, piperidinyl, optionally substituted with methyl, $Me_2N$—$CH_2$—(O)C—;

phenyl, thiophenyl, pyridinyl, pyridazinyl, pyrid-2-onyl pyridin-1-oxidyl, each optionally substituted with methyl, MeO—, $H_3C(O)S$—, $H_3C(O)_2S$—;

imidazolyl, pyrazolyl, oxadiazolyl, isoxazolyl each optionally substituted with methyl;

$R^2$ is $R^{2.1}R^{2.2}R^{2.3}C$—;

$R^{2.1}$ is phenyl, pyridinyl, each optionally substituted with one residue selected from the group consisting of NC—, F—, Cl— in para-position and optionally another residue selected from the group consisting of Cl—, F—, MeO—, $Me(O)_2S$—;

$R^{2.2}$ is H;

$R^{2.3}$ is H or methyl;

$R^3$ is methyl;

$R^4$ is phenyl or pyridinyl, each substituted with a residue selected from the group consisting of Me, Cl—, $F_2HC$—, $F_3C$—;

$R^5$ is H;

or a salt thereof.]

[5. A compound of formula 1, according to claim 1, wherein $R^1$ is $R^{1.1}HN$—, $R^{1.2}HN$—;

$R^{1.1}$ is cyclopropyl or oxetanyl; wherein each element of one of the above mentioned rings is optionally substituted with NC—;

$R^{1.2}$ is methyl or ethyl, optionally substituted independently from each other with one or two residues selected from the group consisting of halogen, NC or oxadiazolyl, substituted with methyl;

$R^2$ is $R^{2.1}R^{2.2}R^{2.3}C$—;

$R^{2.1}$ is phenyl or pyridinyl; wherein each element of one of the above mentioned rings is optionally substituted with a residue selected from the group consisting of NC—;

$R^{2.2}$ is methyl;

$R^{2.3}$ is H;

$R^3$ is methyl;

$R^4$ is phenyl or pyridinyl; wherein each element of one of the above mentioned rings is optionally substituted with a residue selected from the group consisting of $FH_2C$—, $F_2HC$—, $F_3C$—;

$R^5$ is H;

or a salt thereof.]

[6. A pharmaceutical composition comprising a compound of formula 1 according to claim 1 or a pharmaceutically active salt thereof and a pharmaceutically acceptable carrier.]

*7. A compound according to claim 1, wherein the compound is Example 2.3 having the following structure:*

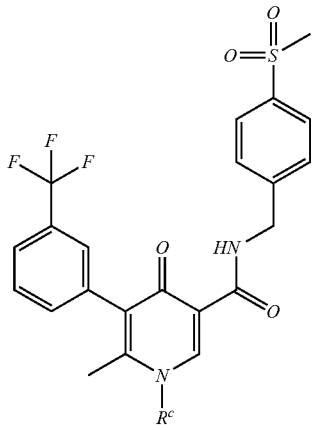

*wherein $R^c$ is:*

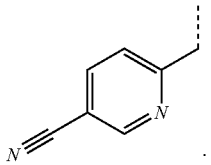

*8. A compound according to claim 1, wherein the compound is Example 2.5 having the following structure:*

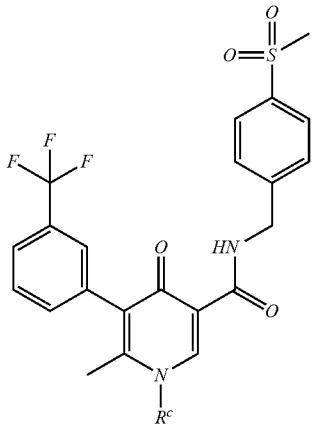

*wherein $R^c$ is:*

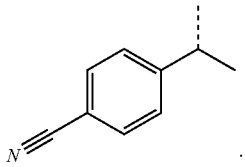

*9. A compound according to claim 1, wherein the compound is Example 2.8 having the following structure:*

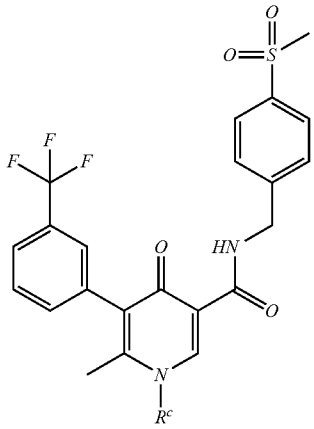

*wherein $R^c$ is:*

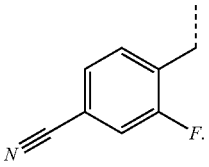

*10. A compound according to claim 1, wherein the compound is Example 2.9 having the following structure:*

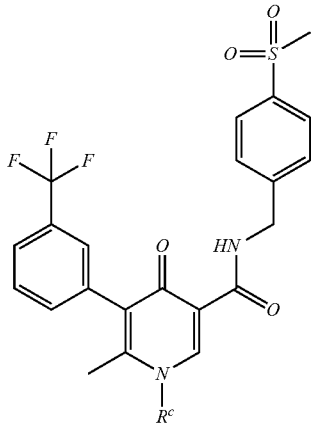

*wherein $R^c$ is:*

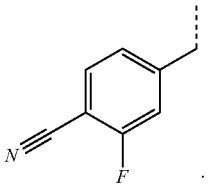

*11. A compound according to claim 1, wherein the compound is Example 2.12 having the following structure:*

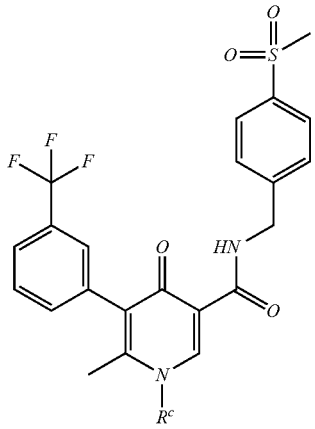

*wherein $R^c$ is:*

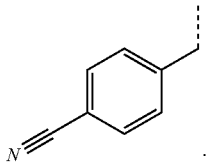

*12. A compound according to claim 1, wherein the compound is Example 4.1 having the following structure:*

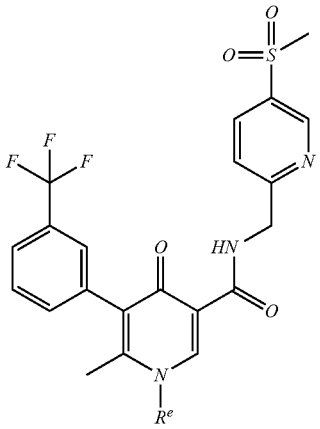

*wherein $R^e$ is:*

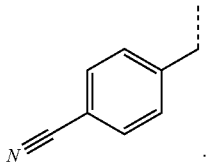

*13. A compound according to claim 1, wherein the compound is Example 4.7 having the following structure:*

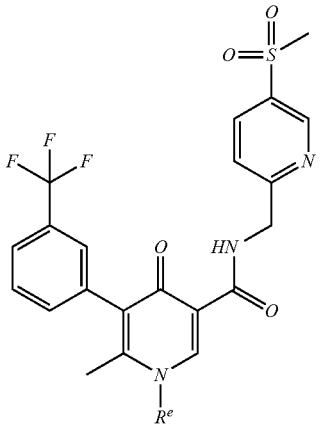

*wherein $R^e$ is:*

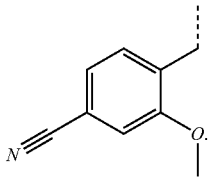

*14. A compound according to claim 1, wherein the compound is Example 4.9 having the following structure:*

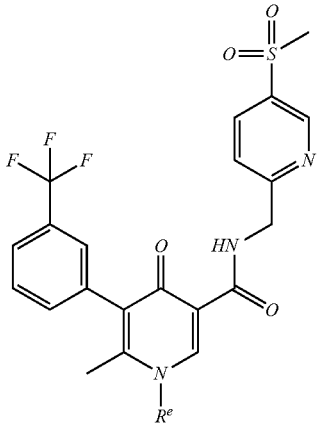

*wherein $R^e$ is:*

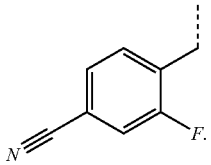

*15. A compound according to claim 1, wherein the compound is Example 4.10 having the following structure:*

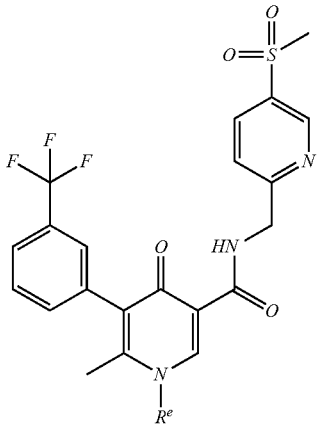

*wherein $R^e$ is:*

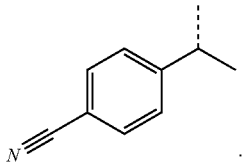

*16. A compound according to claim 1, wherein the compound is Example 6.8 having the following structure:*

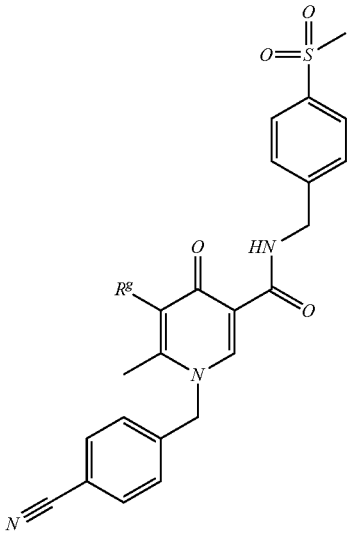

*wherein $R^g$ is:*

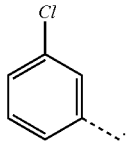

*17. A compound according to claim 1, wherein the compound is Example 6.10 having the following structure:*

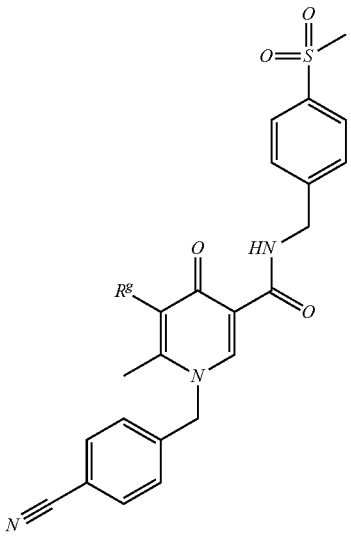

*wherein $R^g$ is:*

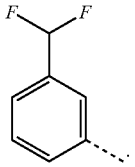

*18. A compound according to claim 1, wherein the compound is Example 6.11 having the following structure:*

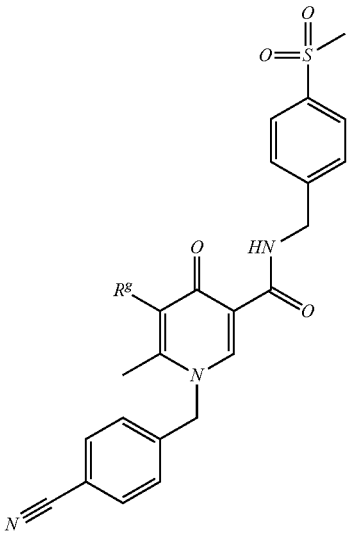

*wherein $R^g$ is:*

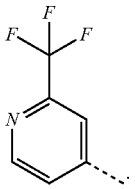

*19. A compound according to claim 1, wherein the compound is Example 7.18 having the following structure:*

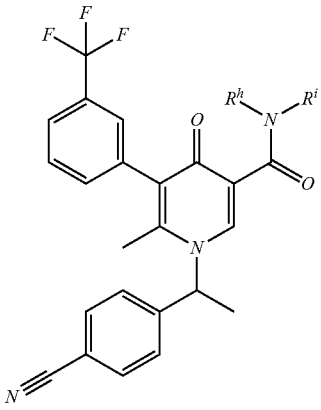

*wherein $R^hR^iN$-is:*

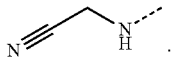

*20. A compound according to claim 1, wherein the compound is Example 11 having the following structure:*

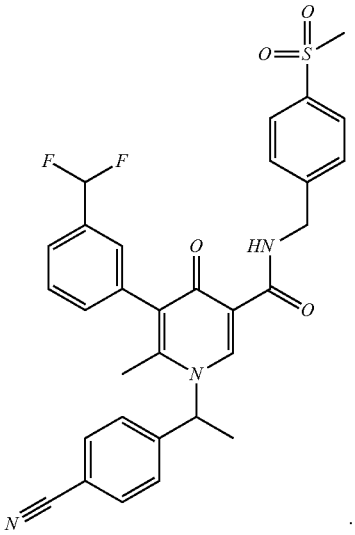

*21. A compound according to claim 1, wherein the compound is Example 14 having the following structure:*

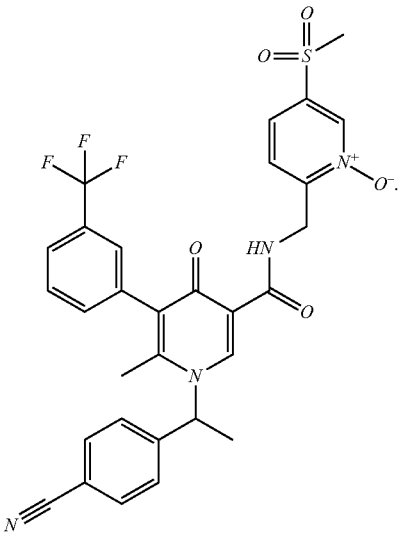

*22. A compound according to claim 1, wherein the compound is Example 39 having the following structure:*

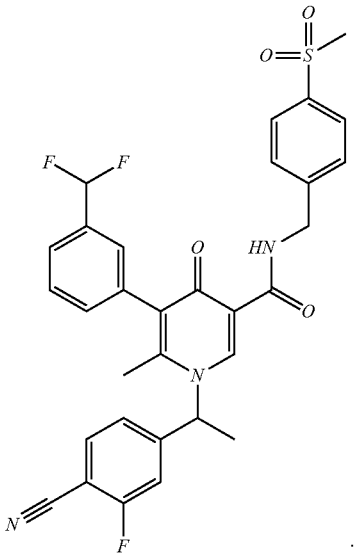

*23. A compound according to claim 1, wherein the compound is Example 40 having the following structure:*

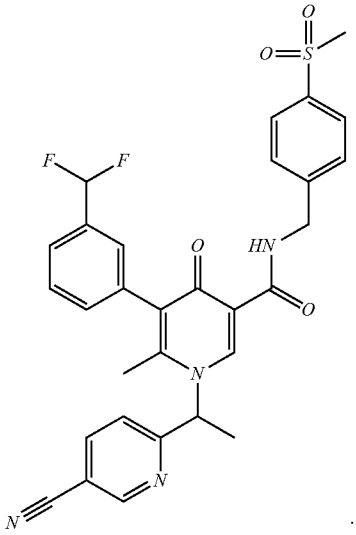

*24. A compound according to claim 1, wherein the compound is Example 41 having the following structure:*

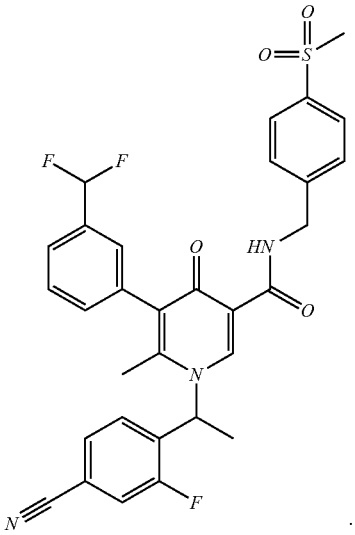
O
O
S
F
F
O
HN
O
N
F
N
* * * * *